(12) United States Patent
Chakraborty et al.

(10) Patent No.: US 10,392,443 B2
(45) Date of Patent: Aug. 27, 2019

(54) DIAGNOSTIC AND THERAPEUTIC TOOL FOR CANCER

(71) Applicant: Agency for Science, Technology and Research, Singapore (SG)

(72) Inventors: Sayan Chakraborty, Singapore (SG); Wanjin Hong, Singapore (SG)

(73) Assignee: Agency for Science, Technology and Research (SG)

( * ) Notice: Subject to any disclaimer, the term of this patent is extended or adjusted under 35 U.S.C. 154(b) by 75 days.

(21) Appl. No.: 15/315,597

(22) PCT Filed: Jun. 2, 2015

(86) PCT No.: PCT/SG2015/050134
§ 371 (c)(1),
(2) Date: Dec. 1, 2016

(87) PCT Pub. No.: WO2015/187095
PCT Pub. Date: Dec. 10, 2015

(65) Prior Publication Data
US 2017/0198055 A1    Jul. 13, 2017

(30) Foreign Application Priority Data
Jun. 2, 2014 (SG) .......................... 10201402829Q

(51) Int. Cl.
| | | |
|---|---|---|
| *A61K 39/395* | (2006.01) | |
| *C07K 16/30* | (2006.01) | |
| *C07K 16/18* | (2006.01) | |
| *A61K 31/7105* | (2006.01) | |
| *A61K 31/713* | (2006.01) | |
| *G01N 33/574* | (2006.01) | |
| *C07K 16/32* | (2006.01) | |
| *C12N 15/113* | (2010.01) | |

(52) U.S. Cl.
CPC .......... *C07K 16/303* (2013.01); *A61K 31/713* (2013.01); *A61K 31/7105* (2013.01); *C07K 16/18* (2013.01); *C07K 16/3015* (2013.01); *C07K 16/32* (2013.01); *C12N 15/1135* (2013.01); *C12N 15/1138* (2013.01); *G01N 33/57415* (2013.01); *G01N 33/57438* (2013.01); *C07K 2317/24* (2013.01); *C07K 2317/34* (2013.01); *C07K 2317/76* (2013.01); *C07K 2317/77* (2013.01); *C12N 2310/14* (2013.01); *C12N 2310/531* (2013.01); *G01N 2333/4722* (2013.01)

(58) Field of Classification Search
None
See application file for complete search history.

(56) References Cited

FOREIGN PATENT DOCUMENTS

| | | | |
|---|---|---|---|
| EP | 2463658 | A1 | 6/2012 |
| EP | 2484695 | A1 | 8/2012 |
| WO | WO 2014/078232 | * | 5/2014 |
| WO | WO-2015/136472 | A1 | 9/2015 |

OTHER PUBLICATIONS

Zhang et al (Plos One, Mar. 2014, 9:e91816, internet pp. 1-6).*
Tatrai et al (Laboratory Investigation, 2006, 86:1149-1160) in IDS.*
Batmunkh et al (Human Pathology, 2007, 38:1508-1515) in IDS.*
Batmunkh, E. et al., Comparison of the expression of agrin, a basement membrane heparan sulfate proteoglycan, in cholangiocarcinoma and hepatocellular carcinoma, Human Pathology, 38(10):1508-1515 (2007).
Batmunkh, E. et al., High expression of Argin in hepatocellular and cholangiocellular carcinoma, Journal of Hepatology, 42(2):88, Abstract 228 (2005).
Bezakova, G. and Ruegg, M.A., New insights into the roles of Agrin, Nat Rev Mol Cell Biol, 4(4):295-308 (2003).
Bhattacharya, et al., Recruitment of vimentin to the cell surface by beta3 integrin and plectin mediates adhesion strength, Journal of Cell Science, 122(9):1390-1400 (2009).
Boersema, P.J. et al., Quantification of the N-glycosylated Secretome by Super-SILAC During Breast Cancer Progression and in Human Blood Samples, Mol Cell Proteomics, 12(1):158-171 (2013).
Burden, S.J. et al., Agrin/MuSK signaling: willing and Abl, Nature Neuroscience, 6(7):653-654 (2003).
Burgess, R.W. et al., Agrin Isoforms with Distinct Amino Termini: Differential Expression, Localization, and Function, The Journal of Cell Biology, 151(1):41-52 (2000).
Casaletto, J.B. and McClatchey, A.I., Spatial regulation of receptor tyrosine kinases in development and cancer, Nature Reviews Cancer, 12(6):387-400 (2012).
Chaffer, C.L. and Weinberg, R.A., A Perspective on Cancer Cell Metastasis, Science, 331(6024):1559-1564 (2011).
Chakraborty, S. et al., An oncogenic role of Agrin in regulating focal adhesion integrity in hepatocellular carcinoma, Nature Communications, 6:6184 (2015).
Chakraborty, S. et al., c-Cbl-Mediated Selective Virus-Receptor Translocations into Lipid Rafts Regulate Productive Kaposi's Sarcoma-Associated Herpesvirus Infection in Endothelial Cells, Journal of Virology, 85(23):12410-12430 (2011).
Chan, K.F. et al., FAK alters invadopodia and focal adhesion composition and dynamics to regulate breast cancer invasion, J. Cell Biol., 185(2):357-370 (2009).
Chan, S.W. et al., A Role of TAZ Migration, Invasion, and Tumorigenesis of Breast Cancer Cells, Cancer Res, 68(8):2592-2598 (2008).
Cheng, N. et al., Argonaute2 Promotes Tumor Metastasis by Way of Up-regulating Focal Adhesion Kinase Expression in Hepatocellular Carcninoma, Hepatology, 57(5):1906-1918 (2013).

(Continued)

*Primary Examiner* — Laura B Goddard
(74) *Attorney, Agent, or Firm* — Choate, Hall & Stewart LLP

(57) ABSTRACT

Disclosed is a method for determining the likelihood of the presence or progression of a hepatocellular carcinoma in a subject, comprising determining the level of extracellular form of Agrin in an extracellular fluid obtained from the subject. Also disclosed are the use of anti Agrin agent for therapy, a pharmaceutical composition comprising anti-Agrin agent, a method of treating cancer comprising an anti-Agrin agent, a use of anti-Agrin agent and a kit thereof.

8 Claims, 31 Drawing Sheets
Specification includes a Sequence Listing.

(56) References Cited

OTHER PUBLICATIONS

Denzer, A.J. et al., Agrin Binds to the Nerve-Muscle Basal Lamina via Laminin, The Journal of Cell Biology, 137(3):671-683 (1997).
Denzer, A.J. et al., Synaptic differentiation: the role of agrin in the formation and maintenance of the neuromuscular junction, Cell Tissue Res, 290(2):357-365 (1997).
Eckert, M.A. et al., Twist1-induced invadopodia formation promotes tumoor metastasis, Cancer Cell, 19(3):372-386 (2011).
Eustace, B.K. et al., Functional proteomic screens reveal an essential extracellular role for hsp90alpha in cancer cell invasiveness, Nature Cell Biology, 6(6):507-514 (2004).
Feng, M. et al., Therapeutically targeting glypican-3 via a conformation-specific single-domain antibody in hepatocellular carcinoma, Proc Natl Acad Sci U S A, 110(12):E1083-E1091 (2013).
Frisch, et al., Control of Adhesion-dependent Cell survival by Focl Adhesion Kinase, The Journal of Cell Biology, 134:793-799 (1996).
Gursan, N. et al., Value of Glypican 3, Hep Par and alpha fetoprotein in diagnosis of hepatocellular carcinoma, Virchows Arch, 461(Suppl 1): S1-S332, Abstract PS-14-015 (2012).
Harsha, H.E. et al., Quantitative proteomics using stable isotope labeling with amino acids in cell culture, Nature Protocols, 3(3):505-516 (2008).
Hui, K.M., Human hepatocellular carcinoma: Expression profiles-based molecular interpretations and clinical applications, Cancer Letters, 286(1):96-102 (2009).
Huynh, H. et al., Targeting Receptor Tyrosine Kinase Pathways in Hepatocellular Carcinoma, Anit-Cancer Agents in Medicinal Chemistry, 11(6):560-575 (2011).
International Search Report for PCT/SG2015/050134, 5 pages (dated Aug. 13, 2015).
Kalluri, R. and Weinberg, R.A., The basics of epithelial-mesenchymal transition, 119(6):1420-1428 (2009).
Kischel, P. et al., Cell Membrane Proteomic Analysis Identifies Proteins Differentially Expressed in Osteotropic Human Breast Cancer Cells, Neoplasia, 10(9):1014-1020 (2008).
Koneczny, I. et al., MuSK Myasthenia Gravis IgG4 Disrupts the Interaction of LRP4 with MuSK but Both IgG4 and IgG1-3 Can Disperse Preformed Agrin-Independent AChR Clusters, PLoS One, 8(11):e80695 (2013).
Kuo, J.C. et al., Analysis of the myosin-II-responsive focal adhesion proteome reveals a role for beta-Pix in negative regulation of focal adhesion maturation, Nature Cell Biology, 13(4):383-393 (2011).
Lin, L. et al., Induction of Filopodia-like Protusions by Transmembrane Agrin: Role of Agrin Glycosaminoglycan Chains and Rho-Family GTPases, 316(14):2260-2277 (2010).
Linder, S., The matrix corroded: podosomes and invadopodia in extracellular matrix degradation, TRENDS in Cell Biology, 17(3):107-117 (2007).
Neuhuber, B. and Daniels, M.P., Targeting of recombinant agrin to axonal growth cones, Molecular and Cellular Neuroscience, 24(4):1180-1196 (2003).
Neumann, F.R. et al., An Alternative Amino-Terminus Expressed in the Central Nervous System Converts Agrin to a Type II Transmembrane Protein, Molecular and Cellular Neuroscience, 17(1):208-225 (2001).
O'Connor, L.T. et al., Localization and Alternative Splicing of Agrin mRNA in Adult Rat Brain: Transcripts Encoding Isoforms that Aggregate Acetylcholine Receptors Are Not Restricted to Cholinergic Regions, The Journal of Neuroscience, 14(3):1141-1152 (1994).
Parkin, D.M. et al., Global Cancer Statistics, 2002, CA Cancer J Clin, 55(2):74-108 (2005).
Quail, D.F. and Joyce, J.A., Microenvironmental regulation of tumor progression and metastasis, Nat Med, 19(11):1423-1437 (2013).
Roessler, S. et al., A Unique Metastasis Gene Signature Enables Prediction of Tumor Relapse in Early Stage Hepatocellular Carcinoma Patients, Cancer Res, 70(24):10202-10212 (2010).
Shibue, T. and Weinberg, R.A., Integrin beta1-focal adhesion kinase signaling directs the proliferation of metastatic cancer cells disseminated in the lungs, Proc Natl Acad Sci U S A, 106(25):10290-10295 (2009).
Shintani, Y. et al., Collagen I Promotes Metastasis in Pancreatic Cancer by Activating c-Jun NH2-Terminal Kinase 1 and Up-regulating N-Cadherin Expression, Cancer Res, 66(24):11745-11753 (2006).
Somoracz, A. et al., Agrin immunohystochemistry facilitates the determination of primary versus metastatic origin of liver carcinomas, Human Pathology, 41:1310-1319 (2010).
Swa, H.L. et al., Quantitative Proteomics Profiling of Murine Mammary Gland Cells Unravels Impact of Annexin-1 on DNA Damage Response, Cell Adhesion, and Migration, Mol Cell Proteomics, 11(8):381-393 (2012).
Tarone, G. et al., Rous Sarcoma Virus-Transformed Fibroblasts Adhere Primarily at Discrete Protrusions of the Ventral Membrane Called Prodosomes, Experimental Cell Research, 159(1):141-157 (1985).
Tatrai, P. et al., Agrin, a novel basement membrane component in human and rat liver, accumulates in cirrhossi and hepatocellular carcinoma, Laboratory Investigation, 86(11):1149-1160 (2006).
Uhm, C.S. et al., Synapse-Forming Axons and Recombinant Agrin Induce Microprocess Formation on Myotubes, The Journal of Neuroscience, 21(24):9678-9689 (2001).
Whittaker, S. et al., The role of signaling pathways in the development and treatment of hepatocellular carcinoma, Oncogene, 29(36):4989-5005 (2010).
Written Opinion for for PCT/SG2015/050134, 8 pages (dated Aug. 13, 2015).
Wu, C. et al., Arp2/3 complex is critical for lamellipodia and organization of cell-matrix adhesion but dispensable for fibroblast chemotaxis, Cell, 148(5):973-987 (2012).
Wurmbach, E. et al., Genome-Wide Molecular Profiles if HCV-Induced Dysplasia and Hepatocellular Carcinoma, Hepatology, 45(4):938-947 (2007).
Xu, M.A. et al., AXL receptor kinase is a mediator of YAP-dependent oncogenic functions in hepatocellular carcinoma, Oncogene, 30(10):1229-1240 (2011).
Zhang, B. et al., LRP4 Serves as a Coreceptor of Agrin, Neuron, 60(2):285-297 (2008).
Jury, E.C. et al., Agrin Signalling Contributes to Cell Activation and Is Overexpressed in T Lymphocytes from Lupus Patients, Journal of Immunilogy, 179(11): 7975-7983 (2007).
Kawahara, R. et al. Agrin and Perlecan Mediate Tumorigenic Processes in Oral Squamous Cell Carcinoma, PLOS One, 9(12): e115004 (2014).

* cited by examiner h i j

SEQUENCE LISTING

```
<160> NUMBER OF SEQ ID NOS: 5

<210> SEQ ID NO 1
<211> LENGTH: 218
<212> TYPE: PRT
<213> ORGANISM: Homo sapiens

<400> SEQUENCE: 1
```

Gly Phe Ser Gly Pro His Cys Glu Lys Gly Leu Val Glu Lys Ser Ala
1               5                   10                  15

Gly Asp Val Asp Thr Leu Ala Phe Asp Gly Arg Thr Phe Val Glu Tyr
            20                  25                  30

Leu Asn Ala Val Thr Glu Ser Glu Leu Ala Asn Glu Ile Pro Val Pro
            35                  40                  45

Glu Thr Leu Asp Ser Gly Ala Leu His Glu Lys Ala Leu Gln Ser Asn
50                  55                  60

His Phe Glu Leu Ser Leu Arg Thr Glu Ala Thr Gln Gly Leu Val Leu
65                  70                  75                  80

Trp Ser Gly Lys Ala Thr Glu Arg Ala Asp Tyr Val Ala Leu Ala Ile
                85                  90                  95

Val Asp Gly His Leu Gln Leu Ser Tyr Asn Leu Gly Ser Gln Pro Val
            100                 105                 110

Val Leu Arg Ser Thr Val Pro Val Asn Thr Asn Arg Trp Leu Arg Val
            115                 120                 125

Val Ala His Arg Glu Gln Arg Glu Gly Ser Leu Gln Val Gly Asn Glu
            130                 135                 140

Ala Pro Val Thr Gly Ser Ser Pro Leu Gly Ala Thr Gln Leu Asp Thr
145                 150                 155                 160

Asp Gly Ala Leu Trp Leu Gly Leu Pro Glu Leu Pro Val Gly Pro
                165                 170                 175

Ala Leu Pro Lys Ala Tyr Gly Thr Gly Phe Val Gly Cys Leu Arg Asp
                180                 185                 190

Val Val Val Gly Arg His Pro Leu His Leu Leu Glu Asp Ala Val Thr
            195                 200                 205

Lys Pro Glu Leu Arg Pro Cys Pro Thr Pro
210                 215

<210> SEQ ID NO 2
<211> LENGTH: 219
<212> TYPE: PRT
<213> ORGANISM: Rattus rattus

<400> SEQUENCE: 2

Gly Phe Ser Gly Leu His Cys Glu Lys Gly Leu Val Glu Lys Ser Val
1               5                   10                  15

Gly Asp Leu Glu Thr Leu Ala Phe Asp Gly Arg Thr Tyr Ile Glu Tyr
            20                  25                  30

Leu Asn Ala Val Ile Glu Ser Glu Leu Thr Asn Glu Ile Pro Ala Pro
            35                  40                  45

Glu Thr Leu Asp Ser Arg Ala Leu Phe Ser Glu Lys Ala Leu Gln Ser
50                  55                  60

Asn His Phe Glu Leu Ser Leu Arg Thr Glu Ala Thr Gln Gly Leu Val
65                  70                  75                  80

Leu Trp Ile Gly Lys Ala Ala Glu Arg Ala Asp Tyr Met Ala Leu Ala
                85                  90                  95

Ile Val Asp Gly His Leu Gln Leu Ser Tyr Asp Leu Gly Ser Gln Pro
            100                 105                 110

Val Val Leu Arg Ser Thr Val Lys Val Asn Thr Asn Arg Trp Leu Arg
            115                 120                 125

Ile Arg Ala His Arg Glu His Arg Glu Gly Ser Leu Gln Val Gly Asn
            130                 135                 140

Glu Ala Pro Val Thr Gly Ser Ser Pro Leu Gly Ala Thr Gln Leu Asp

```
                145                 150                 155                 160
        Thr Asp Gly Ala Leu Trp Leu Gly Leu Gln Lys Leu Pro Val Gly
                        165                 170                 175

Gln Ala Leu Pro Lys Ala Tyr Gly Thr Gly Phe Val Gly Cys Leu Arg
                        180                 185                 190

Asp Val Val Gly His Arg Gln Leu His Leu Leu Glu Asp Ala Val
                        195                 200                 205

Thr Lys Pro Glu Leu Arg Pro Cys Pro Thr Pro
                        210                 215

<210> SEQ ID NO 3
<211> LENGTH: 129
<212> TYPE: PRT
<213> ORGANISM: Rattus rattus

<400> SEQUENCE: 3

Glu Ile Pro Ala Pro Glu Thr Leu Asp Ser Arg Ala Leu Phe Ser Glu
1               5                   10                  15

Lys Ala Leu Gln Ser Asn His Phe Glu Leu Ser Leu Arg Thr Glu Ala
                20                  25                  30

Thr Gln Gly Leu Val Leu Trp Ile Gly Lys Ala Ala Glu Arg Ala Asp
                35                  40                  45

Tyr Met Ala Leu Ala Ile Val Asp Gly His Leu Gln Leu Ser Tyr Asp
        50                  55                  60

Leu Gly Ser Gln Pro Val Val Leu Arg Ser Thr Val Lys Val Asn Thr
65                  70                  75                  80

Asn Arg Trp Leu Arg Ile Arg Ala His Arg Glu His Arg Glu Gly Ser
                85                  90                  95

Leu Gln Val Gly Asn Glu Ala Pro Val Thr Gly Ser Ser Pro Leu Gly
                100                 105                 110

Ala Thr Gln Leu Asp Thr Asp Gly Ala Leu Trp Leu Gly Gly Leu Gln
                115                 120                 125

Lys

<210> SEQ ID NO 4
<211> LENGTH: 14
<212> TYPE: PRT
<213> ORGANISM: Rattus rattus

<400> SEQUENCE: 4

Leu Leu Glu Asp Ala Val Thr Lys Pro Glu Leu Arg Pro Cys
1               5                   10

<210> SEQ ID NO 5
<211> LENGTH: 30
<212> TYPE: PRT
<213> ORGANISM: Rattus rattus

<400> SEQUENCE: 5

Leu Pro Val Gly Gln Ala Leu Pro Lys Ala Tyr Gly Thr Gly Phe Val
1               5                   10                  15

Gly Cys Leu Arg Asp Val Val Gly His Arg Gln Leu His
                20                  25                  30
```

DIAGNOSTIC AND THERAPEUTIC TOOL FOR CANCER

CROSS-REFERENCE TO RELATED APPLICATIONS

This patent application is a National Stage Entry of International Patent Application No. PCT/SG2015/050134, filed on Jun. 2, 2015, which claims the benefit of priority of Singapore patent application No. 10201402829Q, filed 2 Jun. 2014, the contents of each of which are hereby incorporated by reference in their entirety for all purposes herein.

TECHNICAL FIELD

The present invention relates to biochemistry in particular biomarkers. In particular, the present invention relates to a biomarker associated with cancer and methods of using the biomarker to determine the likelihood that a patient suffers from or progressing in cancer.

BACKGROUND ART

Cancer is a disease caused by the unregulated proliferation of cells due to loss and normal cellular controls. Cancer can develop in any tissue or organ at any age. The most common causes of cancer death are cancers of lung, liver, stomach, colorectal, breast, and oesophageal cancer. In patients with cancer, abnormal cells rapidly grow beyond their usual boundaries and can invade adjoining parts of the body and metastasized. Metastases are the major cause of death from cancer.

According to the World Health Organisation (WHO), cancer is one of the leading causes of death in the world and with the increase in population growth and aging, the number of new cases is expected to rise by about 70% over the next two years. In fact, it is expected that annual cancer cases will increase from significantly within the next two decades.

Cell surface molecules defining various signalling pathways are crucial for many cancer progressions. Certain markers or biomarkers for determining the likelihood of a patient suffering from or progressing in cancer is known in the art. It is an object of the present invention to provide further biomarkers, methods and uses thereof suitable for use in cancer.

SUMMARY OF INVENTION

In one aspect, there is provided a method for determining the likelihood of the presence or progression of a hepatocellular carcinoma in a subject. The method comprises determining the level of extracellular form of Agrin in an extracellular fluid obtained from the subject, wherein an increased level of the extracellular form of Agrin in the extracellular fluid is indicative of the presence or progression of the cancer, wherein an increased level is determined by comparison of the level of extracellular form of Agrin in the subject with the extracellular form of Agrin in a non-diseased subject.

In another aspect, there is provided a method of determining the presence of a breast cancer in a subject comprising determining the presence of membrane-bound Agrin in a tissue sample obtained from the subject, wherein the presence of membrane-bound Agrin in the tissue sample is indicative of the cancer.

In another aspect, there is provided an anti-Agrin agent for use in therapy.

In another aspect, there is provided a pharmaceutical composition comprising the anti-Agrin agent as described herein and a pharmaceutically-acceptable carrier or diluent.

In another aspect, there is provided a method of treating a cancer in a subject in need thereof, comprising administering a composition comprising an anti-Agrin agent as defined herein.

In another aspect, there is provided a use of an anti-Agrin agent in the manufacture of a medicament for treating cancer.

In another aspect, there is provided a kit for carrying out the method as defined herein or for the method as defined herein.

BRIEF DESCRIPTION OF DRAWINGS

The invention will be better understood with reference to the detailed description when considered in conjunction with the non-limiting examples and the accompanying drawings, in which:

FIG. 1 shows expression of Agrin in hepatocellular carcinoma cells.

FIG. 2 shows the internalisation of Agrin in HCC cell lines.

FIG. 3 shows loss-of-functional Agrin reduced cell proliferation and induce apoptosis in HCC cell lines.

FIG. 4 shows Agrin is needed for the oncogenesis of liver cancer cells.

FIG. 5 shows the observation of anti-mesenchynmal characteristics upon Agrin depletion.

FIG. 10 shows Agrin expression is independent on EGFR.

FIG. 12 shows loss-of-functional Agrin reduced cell proliferation and induced apoptosis in HCC cell lines.

FIG. 13 shows anti-mesenchymal characteristics upon Agrin depletion.

FIG. 16 shows representative images of HCC tissue array slides (US Biomax, cat #BC03116) containing normal liver and various HCC stage-wise sections, which were subjected to immunofluorescence analysis using anti-Agrin monoclonal antibody. DNA was counter-stained with DAPI. Scale bar: 10 µm.

DESCRIPTION OF EMBODIMENTS

As known in the art, an accurate cancer diagnosis is essential for adequate and effective treatment. This is particularly important because every cancer type requires a specific treatment regimen which includes, but not limited to, surgery, and/or radiotherapy, and/or chemotherapy, and/or hormone therapy, and/or immunotherapy, and/or complementary/alternative therapies.

Some cancers can be detected at an early stage when treatment is likely to be more effective. Tests have been developed that can detect these cancers well before any symptoms are present. However, for other cancer types, no screening test is routinely used. For such cancers where no routine test is known, the discovery of cancer is through symptoms that can be assessed by a clinician. Accordingly, there is a need to provide an alternative biomarker for detecting cancer in a patient.

Hepatocellular carcinoma (HCC) is the sixth most common malignancy and the third leading cancer having a high mortality rate. Although cell surface molecules defining various signalling pathways are crucial for many cancer progressions, knowledge on such molecules are not well characterized for hepatocellular carcinoma. Moreover, current hepatocellular carcinoma therapies are largely restricted to targeting cell surface receptor tyrosine kinases.

Although cell surface biotinylation followed by proteomic analysis of enriched proteins offers a useful strategy to screen differentially expressed targets in many cancers, a thorough investigation of these are lacking in hepatocellular carcinoma. In the present disclosure, the role of Agrin is discussed further.

Figure 8:
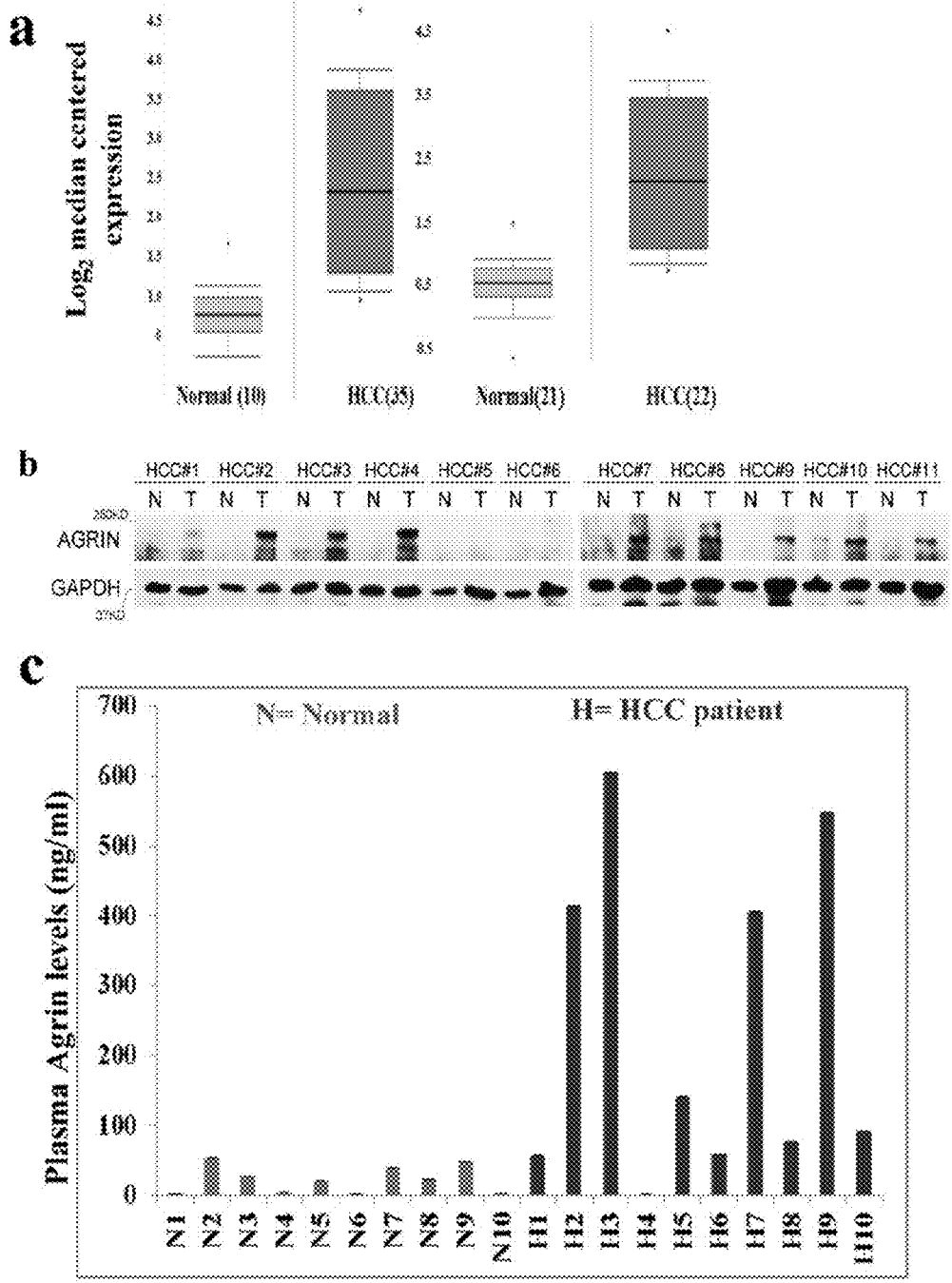
FIG. 8 shows Agrin is frequently overexpressed in hepatocellular carcinoma. In particular, (a) shows gene expression analysis of Agrin using microarray (Oncomine) on normal liver and HCC patient datasets. Pre-processed expression levels are Log 2 normalized and median-centred; (b) shows Western blot analysis for Agrin in a cohort of liver cancer patients in Singapore. GAPDH was used as loading control; (c) shows detection of circulating Agrin in plasma of healthy normal individuals and HCC patients by Agrin ELISA; (d) shows a model describing the role of Agrin in HCC. Overexpression of secreted and membrane associated Agrin triggers binding to its receptor Muscle specific tyrosine kinase (MuSK) that activates focal adhesions and Arp2/3 to generate invadopodia. ECM sensor activity of Agrin is critical for FA activation, invasiveness, and subsequent mesenchymal marker recruitment to cell membrane and thereby EMT program in HCC. Moreover, Agrin is actively internalized through lipid raft domains necessary for intracellular signaling. Cumulatively, these cell surface events triggered by Agrin favours survival related signaling, breaching of cancer cells through ECM to enhance liver tumourigenesis; (e) shows a summary of patient characteristics (disease information and hepatocellular carcinoma stages). The hepatocellular carcinoma patient stages alongside their respective circulatory Agrin levels are shown. High Agrin levels are observed across different stages of hepatocellular carcinoma. It was determined that Agrin expression across different stages of hepatocellular carcinoma is statistically significant compared to its expression in normal livers (***p<0.0003 obtained from student's 't' test). The number of patient samples screened for each stage is indicated in parenthesis. Liver cirrhosis patients were used as positive controls where Agrin is known to be overexpressed. The tissue array consisting of HCC patients were purchased from US Biomax, catalogue numbers: BC03116 and BN03011, respectively).
Figure 8:
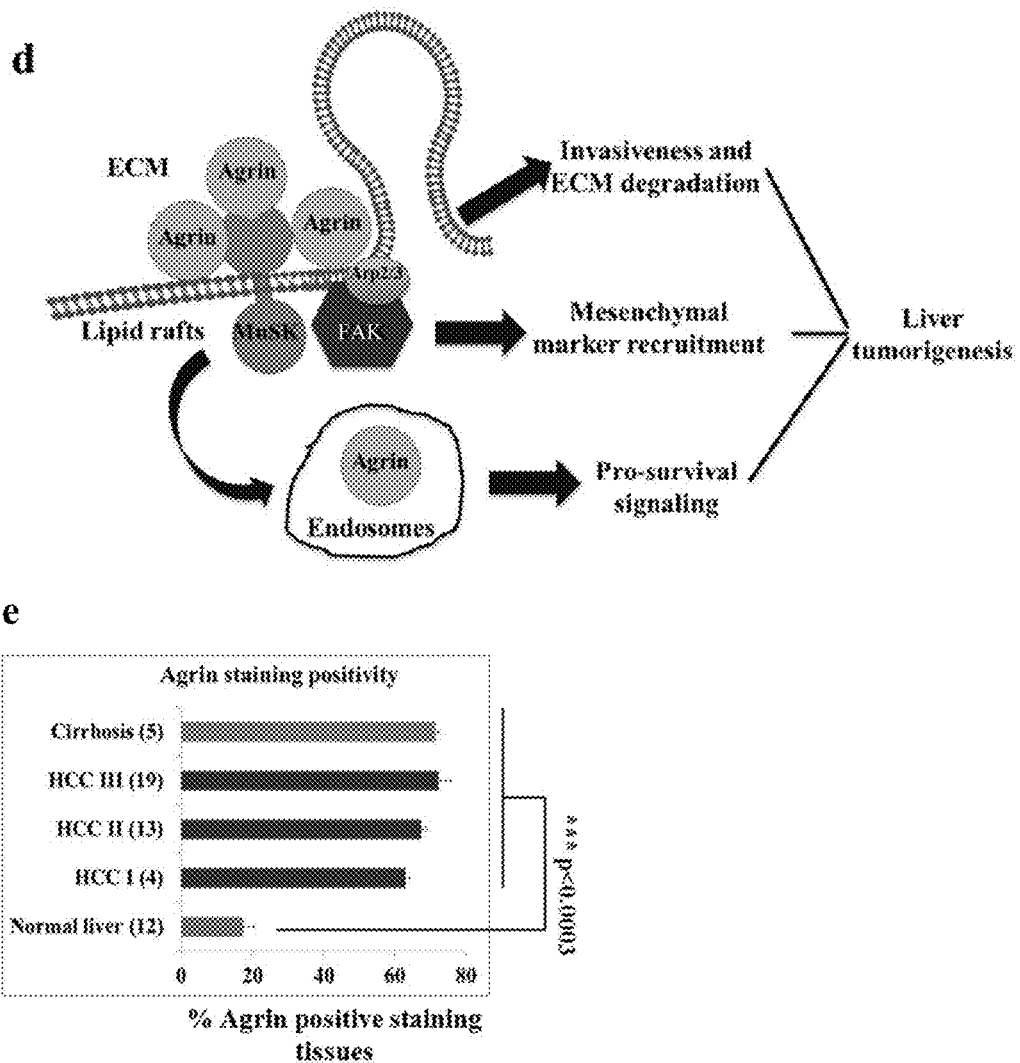

The present disclosure noted that whilst it is known in the art that Agrin immunohistochemistry can facilitate the differentiation between hepatocellular carcinoma and benign tumours, a detailed description and role of secreted or transmembrane Agrin distribution in the art in the liver carcinoma was clearly lacking. The art has simply distinguished hepatocellular carcinoma with benign tumours based on immunohistochemical analysis of Agrin expression. The inventors of the present disclosure have undertaken an unbiased approach of quantitative screen to identify Agrin's detailed role of secreted and transmembrane, substantiated by thorough biochemical evidences about the presence and role of Agrin during different stages of liver carcinoma. This is also validated in HCC tissues and plasma samples, which was demonstrated for the first time. The levels of circulatory and liver tissue specific Agrin were specifically higher compared to normal healthy individuals (FIGS. 8b and c, FIG. 16).

Figure 16:
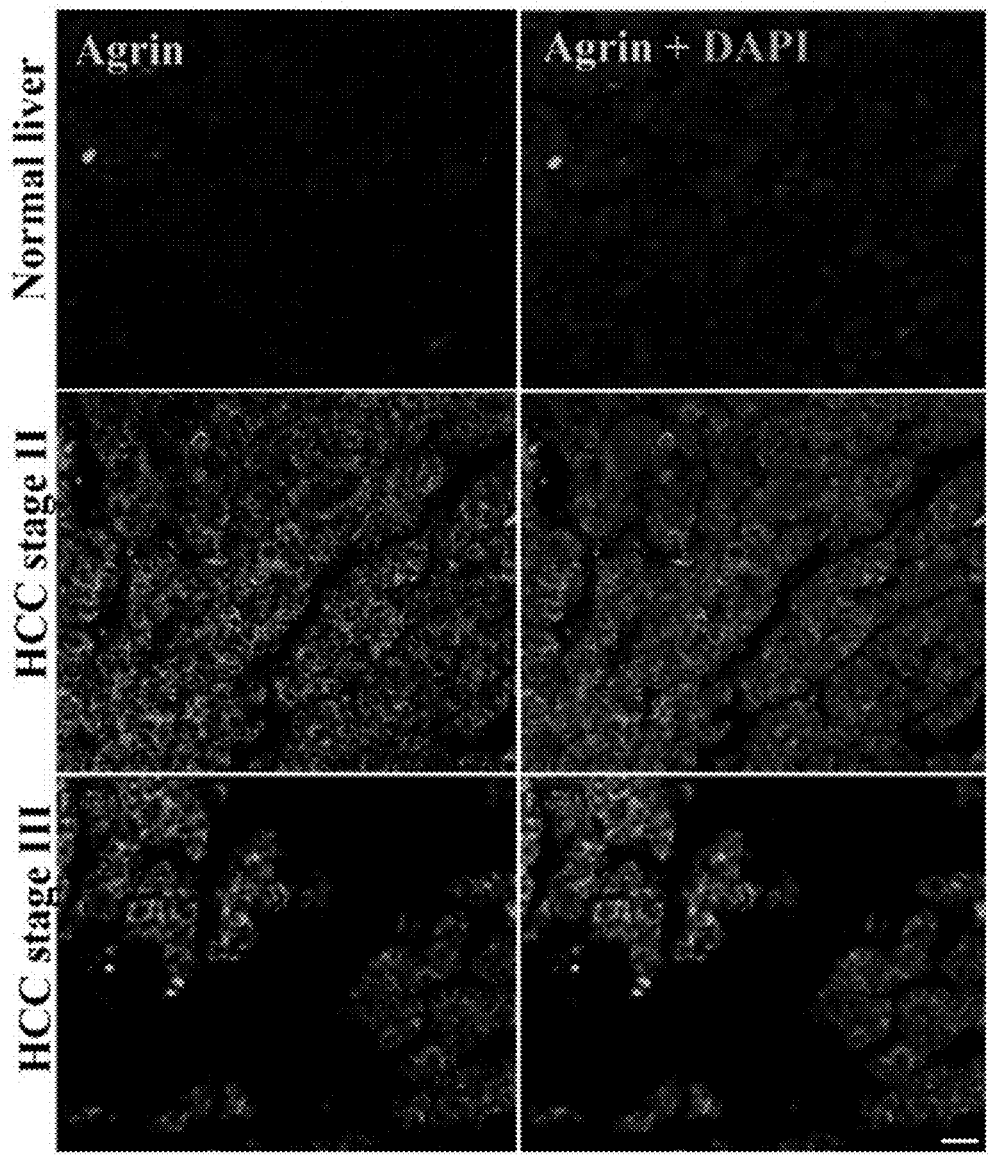
FIG. 16 shows expression of Agrin in normal liver and HCC tissues. In particular.

Based on FIG. 16, the level of Agrin expression was quantified across different stages of HCC. This analysis revealed the presence of the proteoglycan across all stages of HCC (see FIG. 8e). As illustrated in the Examples sections, for example FIGS. 8b, c and e, and FIG. 16, the mere presence of Agrin in the extracellular fluid does not directly indicate the presence of HCC. However, the inventors of the present inventors surprisingly found Agrin is preferentially enriched or increased in level in the circulation of HCC patients. Hence, in one aspect, there is provided a method for determining the likelihood of the presence or progression of a hepatocellular carcinoma in a subject. The method may comprise determining the level of extracellular form of Agrin in an extracellular fluid obtained from the subject. The present disclosure notes that the mere presence of Agrin in the extracellular fluid does not directly indicate the presence of hepatocellular carcinoma. Evidences as disclosed herein, in particular in the Example section, indicates that Agrin is preferentially enriched in the circulation of hepatocellular carcinoma patients. Thus, in the method of the present disclosure, an increased level of the extracellular form of Agrin in the extracellular fluid is indicative of the presence or progression of the cancer. In one example, an increased level may be determined by comparing the level of extracellular form of Agrin in the subject with the extracellular form of Agrin in a non-diseased subject.

Thus, in one example, there is provided a method for determining the likelihood of the presence or progression of a hepatocellular carcinoma in a subject comprising determining the level of extracellular form of Agrin in an extracellular fluid obtained from the subject, wherein an increased level of the extracellular form of Agrin in the extracellular fluid is indicative of the presence or progression of the cancer, wherein an increased level is determined by comparison of the level of extracellular form of Agrin in the subject with the extracellular form of Agrin in a non-diseased subject.

As used herein, the term "Agrin" refers to the approximately 210 kDa proteoglycan (Accession no. AB191264.1), which are glycosylated proteins that have covalently attached highly anionic glycosaminoglycans. In one example, splice variants of Agrin may be expressed either as membrane protein or secreted in extracellular matrix (ECM). In another example, neural Agrin clusters acetylcholine receptors at synaptic clefts and maintains functional neuromuscular junctions. Agrin may be expressed in several tissues including muscles and neurons but to a lesser extent in normal livers. In another example, secreted Agrin binds to Lipoprotein related receptor 4 (Lrp4) and then muscle specific receptor tyrosine kinase (MuSK) forming a signalling complex at neuromuscular junctions. In another example, neural and muscle Agrins also bind laminin in the ECM, which are involved in cytoskeletal rearrangements and neuronal outgrowths with mechanisms remaining unclear.

As used herein, the term "extracellular" refers to proteins, antigens, or epitopes located on the external portion of a cell membrane or are in the fluids of the circulatory structure. In one example, as used herein the phrase "extracellular form of Agrin" refers to Agrin that is located on the external portion of a cell membrane or is in circulation in the extracellular fluid of a subject. In one example, the extracellular Agrin is a splice variant of Agrin that is secreted in extracellular matrix. In one example, the Agrin may comprise or consist of the C-terminal fragment portion (C20) 20 KDa protein fragment. The sequence of the C-terminal fragment portion (C20) 20 kDa fragment is as follows:

```
sp|O00468|AGRIN_HUMAN    GFSGPHCEKGLVEKSAGDVDTLAFDGRTFVEYLNAVTESELANEIPVPET    1899
sp|P25304|AGRIN_RAT      GFSGLHCEKGLVEKSVGDLETLAFDGRTYIEYLNAVIESELTNEIPAPET    1790
                         ** ****::.:*****::** ::* sp|O00468|AGRIN_HUMAN    LDSGALH-EKALQSNHFELSLRTEATQGLVLWSGKATERADYVALAIVDG    1948
sp|P25304|AGRIN_RAT      LDSRALFSEKALQSNHFELSLRTEATQGLVLWIGKAAERADYMALAIVDG    1840
                         *** **  *************************.***:*****:
                         ******* sp|O00468|AGRIN_HUMAN    HLQLSYNLGSQPVVLRSTVPVNTNRWLRVVAHREQREGSLQVGNEAPVTG    1998
sp|P25304|AGRIN_RAT      HLQLSYDLGSQPVVLRSTVKVNTNRWLRIRAHREHREGSLQVGNEAPVTG    1890
                         ****:*******  ****: :*********** sp|O00468|AGRIN_HUMAN    SSPLGATQLDTDGALWLGGLPELPVGPALPKAYGTGFVGCLRDVVVGRHP    2048
sp|P25304|AGRIN_RAT      SSPLGATQLDTDGALWLGGLQKLPVGQALPKAYGTGFVGCLRDVVVGHRQ    1940
                         ******************** :**** ******************:*::

sp|O00468|AGRIN_HUMAN    LHLLEDAVTKPELRPCPTP                                 2067 SEQ ID NO: 1
sp|P25304|AGRIN_RAT      LHLLEDAVTKPELRPCPTP                                 1959 SEQ ID NO: 2
```

As used herein, the term "increased level" refers to an elevated or increased amount of Agrin as compared to the level detected in a non-diseased subject. In one example, the increased level refers to the level of Agrin in extracellular fluid, which is increased or elevated by at least about 100% as compared to the level detected in a non-diseased subject, for example an increase by at least about 200%, or at least about 300%, or at least about 400%, or at least about 500%, or at least about 600%, or at least about 700%, or at least about 800%, or at least about 900% or up to and including a 1000% increase (e.g. significantly higher than the normal level), or any increase between 100-1000% as compared to a normal level. In one example, the increased level refers to the level of Agrin in extracellular fluid, which is increased or elevated by at least about 2 fold as compared to the level detected in a non-diseased subject, for example an increase by at least about 3 fold, or at least about 4 fold, or at least about 5 fold, or at least about 6 fold, or at least about 7 fold, or at least about 8 fold, or at least about 9 fold, or at least about 10 fold or up to and including a 11 fold increase (e.g. significantly higher than the normal level), or any increase between 2-11 fold as compared to a normal level. In one example, the increased level refers to the level of Agrin in extracellular fluid, which is increased or elevated by at least 6 folds as compared to the level detected in a non-diseased subject. In one example, the increased level refers to the level of Agrin in extracellular fluid, which is significantly higher than the normal level. In one example, significantly higher means that the level is higher than that the difference to the normal level is statistically relevant (for example, $p<0.05$, or $p<0.01$). In one example, the term "normal level", which is in contrast with the "increased level", refers to the range of the level of Agrin in an extracellular fluid sample of a non-diseased subject.

As used herein, the term "extracellular fluid" refers to fluid or liquid fraction of total body that is extracellular. Usually, the extracellular fluid comprises about one third of the total body water, which is about three quarter of the extracellular fluid exists in the interstitial space and connective tissues surrounding cells and about one quarter is intravascular. Extracellular fluid is comprised of characteristic concentrations of ions such as sodium, potassium, magnesium, as well as secreted proteins such as cytokines, antibodies, Agrin and the like. In one example, the extracellular fluid may be bodily fluid, such as bodily liquid. The "bodily fluid" as used herein refers to any biological fluid, which is substantially cell free, which can be assayed for protein such as Agrin, including, but is not limited to whole blood, tears, sweat, vaginal secretion, saliva, urine and amniotic fluid. As used herein, whole blood may include, but is not limited to blood cells, plasma and serum. In one example, the extracellular fluid, bodily fluid or bodily liquid may include, but is not limited to whole blood. In one example, the extracellular fluid may be plasma.

As used herein, the term "determining" refers to performing an assay or using a method to ascertain the state of someone or something, for example, the presence, absence, level, or degree of a certain condition, biomarker, disease state, or physiological condition. Thus, in one example, the phrase "determining the level of extracellular form of Agrin" refers to the act of performing an assay or using a method known in the art to ascertain the level or amount of Agrin in a sample obtained in the sample obtained from the subject. In one example, the "determining the level of extracellular form of Agrin" is performed in the plasma of the subject. In one example, the "determining the level of extracellular form of Agrin" may be performed or measured by Enzyme-Linked Immunosorbent Assay (ELISA), mass spectrometry or Western Blot. In one example, the Agrin plasma levels may be measured by Enzyme-Linked Immunosorbent Assay (ELISA), mass spectrometry or Western Blot.

According to the World Health Organisation, breast cancer is the most common cancer in women in both the developed and the developing world. With increasing life expectancy, increased urbanisation and adoption of western lifestyles, incidence of breast cancer has been observed to be increasing in the developing world. It is known that early detection is essential in improving breast cancer outcome and survival. Currently, the most effective breast cancer screening method is mammography screening. Thus, it is another object of the present disclosure to provide an alternative method of determining the presence of a breast cancer in a subject.

Figure 1:
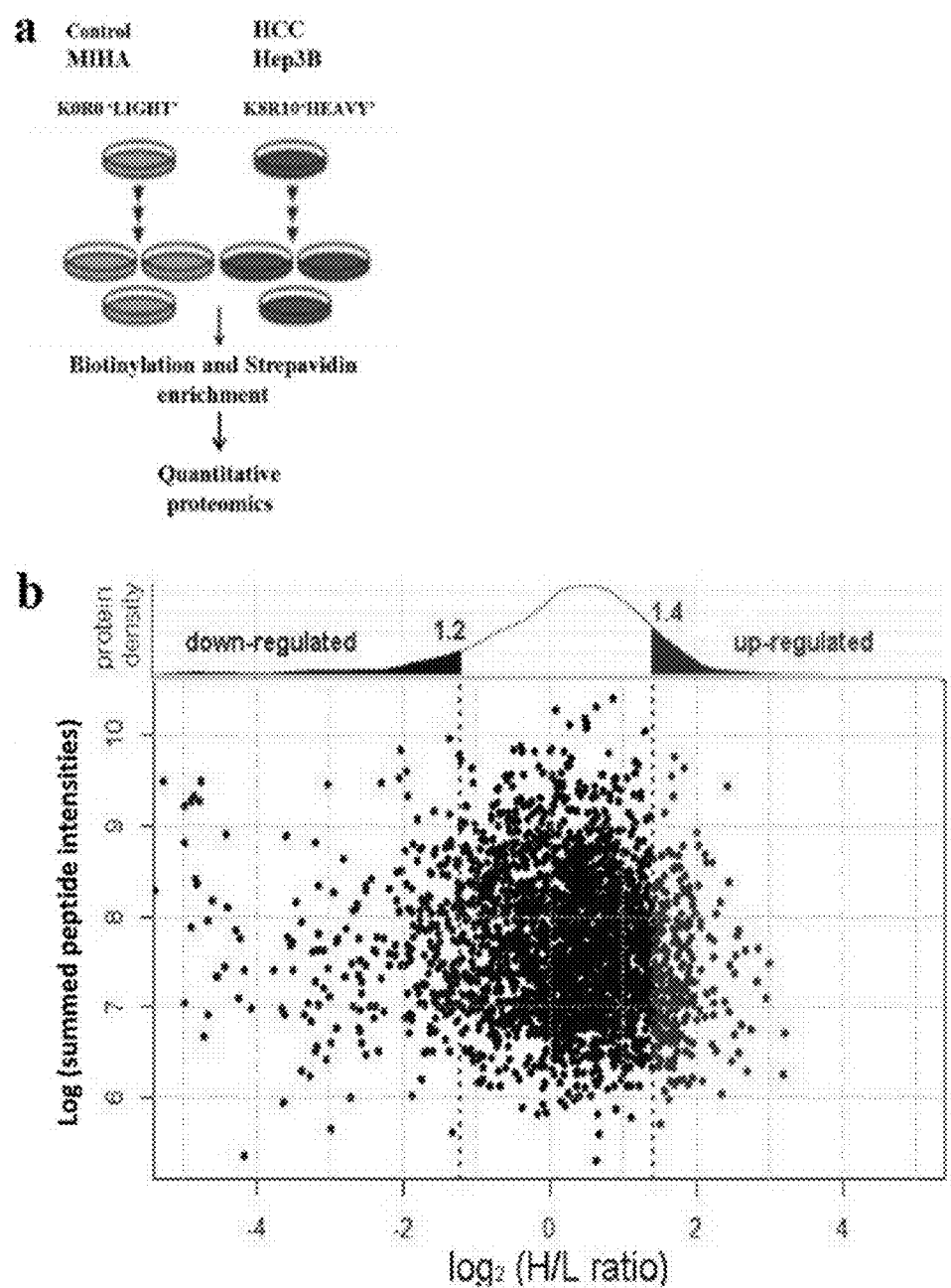
FIG. 1 shows the process of identifying Agrin as an overexpressed cell surface protein in hepatocellular carcinoma cell lines. In particular, (a) shows a schematic workflow of SILAC (Stable isotope labelling by amino acids in cell culture) mass spectrometry based analysis of cell surface proteins where cells of the cell lines MIHA and Hep3B are labelled with 'heavy' and 'light' amino acids and vice-versa; (b) shows the ratio intensity plot representing protein fold change (SILAC ratio vs corresponding summed peptide intensity distribution) and protein density plot (upper panel). Right, left and centre cluster indicates up-, down- and un-regulated proteins; (c) shows gene ontology Cellular Component analysis (GO) of up-regulated proteins in Hep3B cells. The scale bar (Y-axis right hand side) indicates the P-values, while the numbers on top of each bar denotes the abundance of identified proteins in the particular cellular component; (d) shows Western blot analysis of biotinylated cell surface proteins and total cell lysates from the indicated cell lines; (e) shows Western blot evaluation of Agrin expression in non-tumourigenic, hepatocellular (HCC) and selected breast carcinoma cell lines. β-actin is used as loading control; (f) shows Western blot analysis of supernatants from serum starved (12 h) cell lines, which were concentrated and precipitated with Tri-chloroacetic acid (TCA). Total cell lysates from the same cell lines were also probed for Agrin and β-actin as loading control; and (g) shows levels of Agrin in mouse xenografts of indicated cell lines analysed by Western blot using an Agrin specific monoclonal antibody. β-actin served as loading control.
Figure 1:
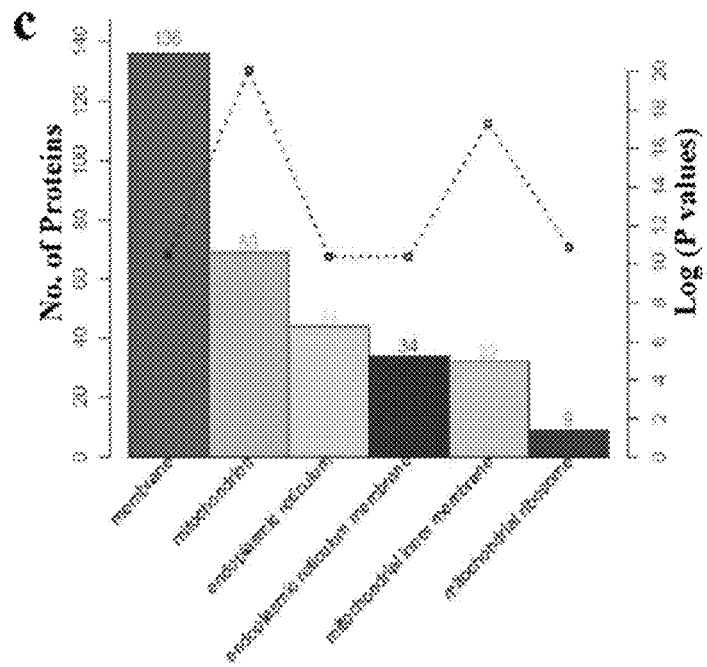
Figure 1:
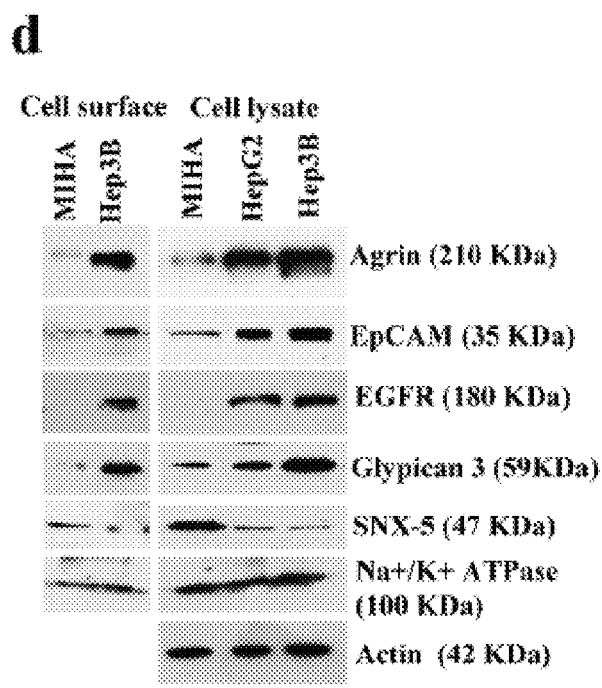
Figure 1:
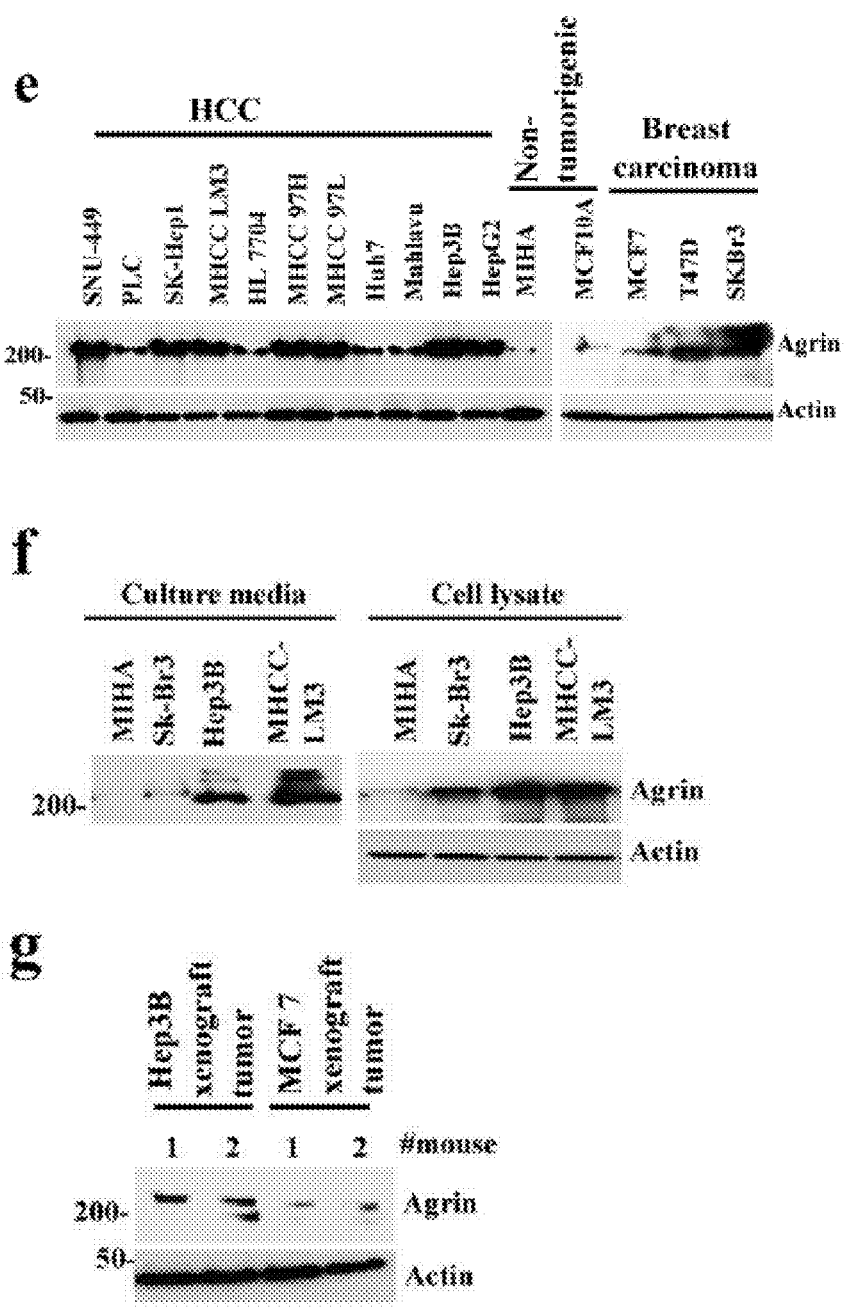

Thus, in another aspect, there is provided a method of determining the presence of a breast cancer in a subject. In one example, the method may comprise determining the presence of membrane-bound Agrin in a tissue sample obtained from the subject, wherein the presence of membrane-bound Agrin in the tissue sample is indicative of the cancer. The Example section, in particular FIG. 1e, shows Agrin is highly expressed in breast cancer cell lines.

As used herein, the term "membrane-bound" refers to a protein, antigen or epitope that is bound to the membrane of a cell. In one example, the term "membrane-bound Agrin" refers to Agrin which is bound to the cellular membrane of a breast tissue or is expressed on an immune cell, such as antigen-presenting cells, in a lymphoid tissue. Thus, in one example, the term "tissue sample", when used in relation with breast cancer, includes, but is not limited to, breast tissue and lymph node.

As used herein, the term "subject" may be used interchangeably with "patient" and refers to an animal, including mammals, such as human, bovine, porcine, equine, canine, lupine, feline, murine and the like.

As used herein, the term "a non-diseased subject" refers to a clinically relevant comparative subject, including, for example, a healthy subject not afflicted with cancer, a healthy normal individual, a subject having a disease other than cancer (a cancer-free subject who may have other disease(s)), and the like. In one example, the non-diseased subject is a cohort of non-diseased individuals. For example, in Examples section below, the level of circulating Agrin in plasma in HCC patients is compared to the level of circulating Agrin in plasma of healthy normal individuals (see FIGS. 8c and 16).

In one example, the method as described herein may further comprise one or more diagnostic means including, but is not limited to an imaging test and tissue biopsy. In one example, the imaging test could be a Magnetic Resonance Imaging (MRI) or mammographic screening. In one example, the term "tissue biopsy", when used in relation with hepatocellular carcinoma, includes, but is not limited to, liver tissue and lymph node.

At the same time, it is known that cytoskeletal rearrangements, membrane protrusions and degradation of ECM are essential for invasion, epithelial-mesenchymal transition (EMT) and metastasis in cancers. The roles of integrin associated focal adhesion proteins including focal adhesion kinases (FAK) are also very well characterized in cancer invasion and mesenchymal characteristics. However except for collagen, very few ECM proteins are known to regulate integrin-focal adhesion dependant cellular invasiveness. Furthermore, histo-pathological analyses have indicated an accumulation of Agrin proteoglycan in liver cirrhosis and basement membranes of induced HCC and cholangiocarcinomas in rat livers with undefined role in HCC. Additionally, whether Agrin regulates integrin and focal adhesion dependant cancer cell migration, invasion and tumour progression is also unknown.

The Examples section of the present disclosure shows that Agrin is over-expressed and secreted in HCC cell lines and patient samples. Suppressing Agrin function via knockdown or antibodies inhibited proliferation and activated apoptosis in HCC cell lines, while overexpressing Agrin in non-tumourigenic liver cells increased proliferation. Importantly, Agrin depletion inhibited cell migration, clonogenecity and Arp2/3 dependant invadopodia formation. Agrin binds to MuSK receptor and acts as an ECM sensor regulating focal adhesion dynamics and EMT marker recruitment. Disrupted focal adhesion and reduced mesenchymal properties in Agrin depleted cells can be reversed by restoring the function of either Agrin or Focal adhesion kinase (FAK). In vivo, Agrin depletion by shRNA or function blocking antibodies suppressed oncogenic signaling and tumour development. Thus, the present disclosure shows that targeting Agrin can have therapeutically benefits.

In another aspect, there is provided a method of treating a cancer in a subject in need thereof. The method comprises administering a composition comprising an anti-Agrin agent.

The terms "treat," "treatment," "treating", and grammatical variants thereof, refer to both therapeutic treatment and prophylactic or preventative measures, wherein the object is to prevent or slow down (lessen) an undesired physiological condition, disorder or disease or obtain beneficial or desired clinical results. Such beneficial or desired clinical results include, but are not limited to, alleviation of symptoms; diminishment of extent of condition, disorder or disease; stabilized (i.e. not worsening) state of condition, disorder or disease; delay or slowing of condition, disorder or disease progression; amelioration of the condition, disorder or disease state, remission (whether partial or total), whether detectable or undetectable; or enhancement or improvement of condition, disorder or disease. Treatment includes eliciting a cellular response that is clinically significant, without excessive levels of side effects. Treatment also includes prolonging survival as compared to expected survival if not receiving treatment.

Figure 7:
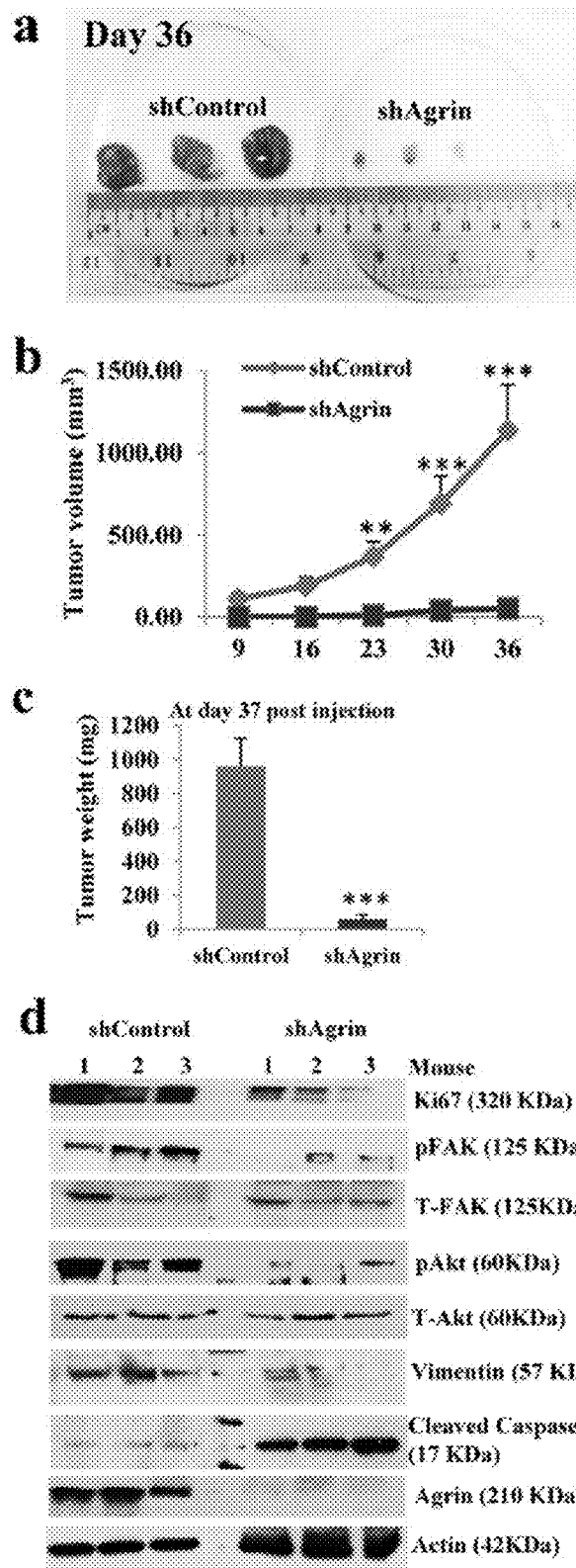
FIG. 7 shows targeting Agrin by shRNAs or monoclonal antibodies suppress oncogenic signaling and tumour growth. In particular, (a) shows representative images of xenograft tumours at day 36 post s.c. injection of control or Agrin shRNA expressing MHCC-LM3 cells ($10^7$ cells/ml), which were injected subcutaneously in athymic nude mice to establish tumours; (b and c) show graphs of tumour sizes measured and depicted as tumour volume (b) or tumour weight (c) (P value=0.005, 0.0005 and 0.0005, respectively indicated by asterisks); (d) shows Western blot analysis in mouse xenografts from (a) showing the expression of indicated proteins; (e) shows representative bright field images of MHCC-LM3 cells, which were pre-treated with Agrin antibodies for 12 h and had a wound scratch assay performed in presence of respective antibodies. Representative bright field images are shown at indicated time-points post-scratching. Results are quantitated using ImageJ software; (f) shows Western blot analysis of MHCC-LM3 cells, which were pre-treated with Agrin antibodies for 12 h and lysates were analysed for the indicated proteins; (g and h) show the results of a study where athymic nude mice were injected s.c. with MHCC-LM3 cells ($10^7$ cells/ml) to develop tumours. After the tumours reached a size of 100-200 mm3, MAb5204 antibody against Agrin (n=3) or PBS control (n=6) were injected at a dose of 10 mg/kg for 2 weeks at an interval of 4 days. Tumour sizes shown after mice were sacrificed at day 30. Mean tumour volume is represented in (h). Error bar represents standard error of mean (+/−SEM); (i) shows a bar graph depicting the results of tumour growth inhibition assay with respect to PBS control on the days with subsequent antibody injection; (j) shows immunohistochemical analyses of antibody treated or PBS treated tumours stained for proliferation marker (Ki67) and apoptosis marker (cleaved caspase-3). Representative bright field images are shown (n=3). Boxed areas are represented as enlarged panels. Scale bar: 100 µm. Thus, FIG. 7 strongly support conclusions reached from in vitro studies.
Figure 7:
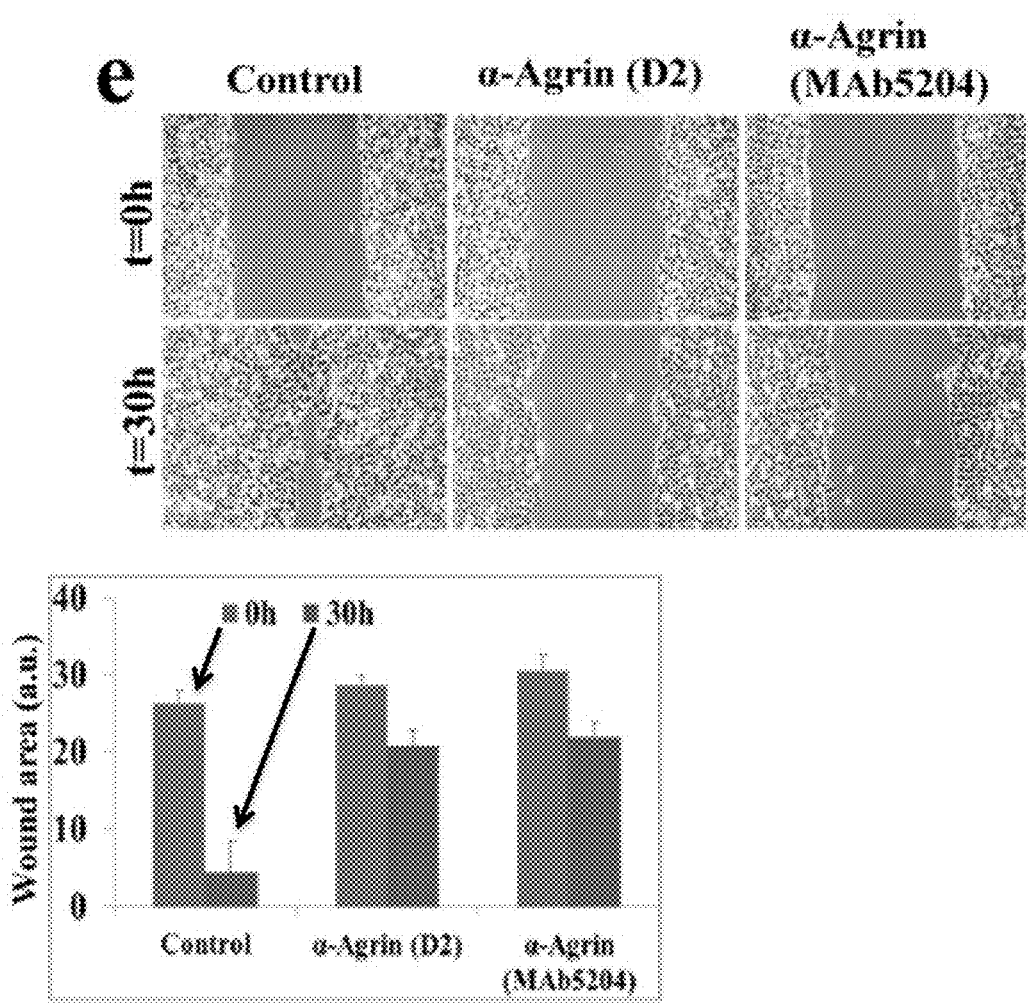
Figure 7:
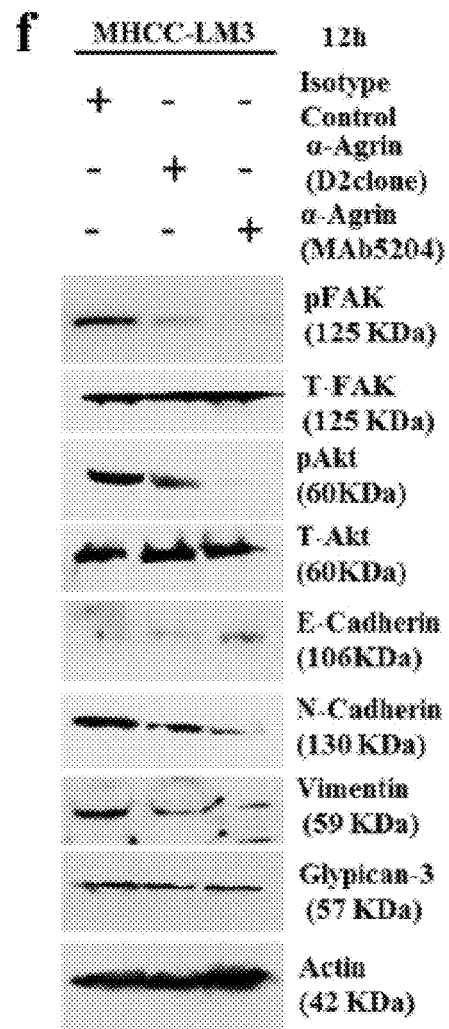
Figure 7:
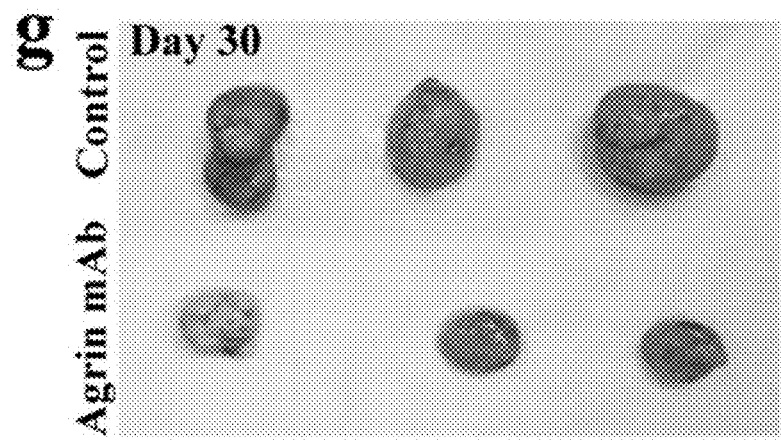
Figure 7:
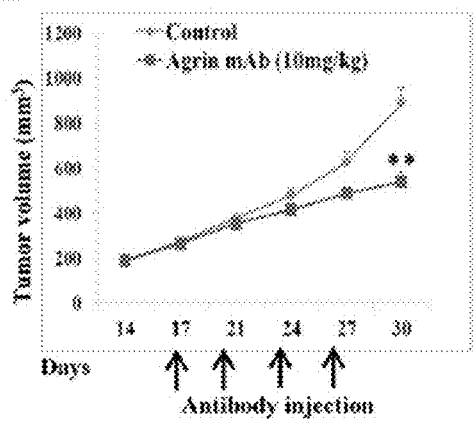
Figure 7:
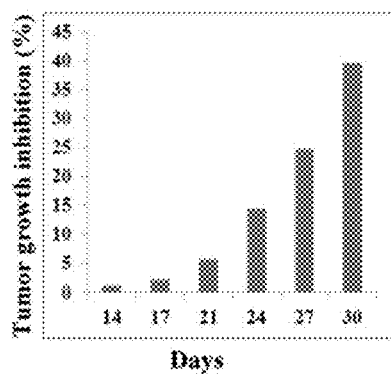
Figure 7:
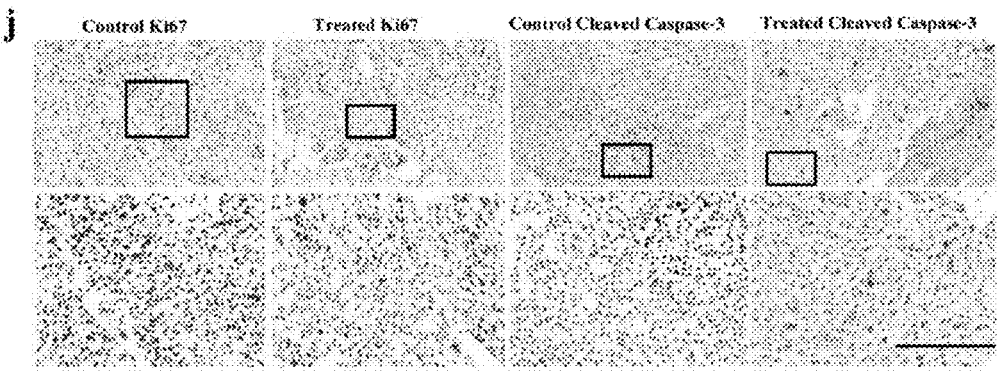

The term "anti-Agrin agent" as used herein, refers to an agent such as a compound, small molecules, proteins, RNAs that can inhibit the biological activity of Agrin in a cell or in a subject. For example, the anti-Agrin agent may be an anti-Agrin antibody. In one example, the anti-Agrin antibody may prevent the uptake of Agrin into a cancer cells. In one example, the anti-Agrin agent may be an inhibitory nucleic acid that specifically inhibits the translation of Agrin in a cancer cell. As used herein, the term "inhibit" refers to the suppression or decrease in the biological activity of Agrin in a subject. For example, the inhibition may cause a suppression or decrease in the amount of Agrin as compared to the level detected before the administration of the anti-Agrin agent. In one example, the inhibited or decreased level refers to the level of Agrin in extracellular fluid, which is decreased or reduced by at least 10% as compared to the level detected in the subject before treatment with anti-Agrin, for example an decreased by at least about 20%, or at least about 30%, or at least about 40%, or at least about 50%, or at least about 60%, or at least about 70%, or at least about 80%, or at least about 90% or up to and including a 100% reduction (e.g. significantly lower than the normal level), or any decrease between 10-100% as compared to the level in a subject before treatment with anti-Agrin. As illustrated in FIGS. 7g, 7h and 7i, administration of anti-Agrin agent, such as anti-Agrin antibody significantly reduced the size of tumour in mice. Accordingly, in one example, the inhibition may cause a reduction in the size of tumour in a subject as compared to the size detected in the subject before the treatment with anti-Agrin agent. In one example, the inhibition or reduction in the size of the tumour may refer to a decrease or reduction by at least 10% as compared to the size of the tumour detected in the subject before treatment with anti-Agrin. In another example, the inhibition or reduction in size of the tumour may refer to a decrease by at least about 20%, or at least about 30%, or at least about 40%, or at least about 50%, or at least about 60%, or at least about 70%, or at least about 80%, or at least about 90% or up to and including a 100% reduction (e.g. substantially complete elimination of tumour), or any decrease between 10-100% as compared to the size of the tumour in the subject before treatment with anti-Agrin. In one example, the inhibitory nucleic acid may include, but is not limited to, antisense RNA, a ribozyme, a short inhibitory RNA (siRNA), and a microRNA (mRNA).

As used herein the term "cancer", or "tumour", are well known in the art and refer to the presence of cells possessing characteristics typical of cancer-causing cells, such as uncontrolled proliferation, immortality, metastatic potential, rapid growth and proliferation rate, decreased cell death/apoptosis, and certain characteristic morphological features. For example, cancer cells are often in the form of a solid tumour. In another example, cancer may also include non-solid tumours such as blood tumours, for example leukaemia, where the cells are derived from bone marrow. In one example, the term "cancer" may include pre-malignant cancers. In another example, the term "cancer" may include malignant cancer. In yet another example, the term "cancer" may include both pre-malignant cancer and malignant cancer. In one example, the term cancer may include, but is not limited to, hepatocellular carcinoma, a breast cancer carcinoma and a cholangiocarcinoma.

As used herein, the term "subject" may be used interchangeably with "patient" and refers to an animal, including mammals, such as human, bovine, porcine, equine, canine, lupine, feline, murine and the like. In one example, the "subject" is a human.

In one example, the anti-Agrin agent is an antibody. As used herein, the term "antibody" refers to all types of antibodies that specifically bind to Agrin. In one example, the antibody may be an antibody that functionally blocks the c-terminally active signalling component of membrane bound Agrin. In one example, the targeting of C terminal fragment of Agrin (secreted Agrin) may contain the C-terminal fragment portion (C20) 20 kDa protein fragment. The sequence of the 20 kDa fragment bearing the epitopes for the function blocking antibodies is as follows:

Human and rat Agrin (C20 fragment) sequence showing the epitopes for Agrin monoclonal antibodies D2 (bold) and MAb5204 (underlined) is as follows:

```
sp|O00468|AGRIN_HUMAN    GFSGPHCEKGLVEKSAGDVDTLAFDGRTFVEYLNAVTESELANEIPVPET    1899
sp|P25304|AGRIN_RAT      GFSGLHCEKGLVEKSVGDLETLAFDGRTYIEYLNAVIESELTNEIPAPET    1790
                         **  ******   ******  **:*****:* sp|O00468|AGRIN_HUMAN    LDSGALH-EKALQSNHFELSLRTEATQGLVLWSGKATERADYVALAIVDG    1948
sp|P25304|AGRIN_RAT      LDSRALFSEKALQSNHFELSLRTEATQGLVLWIGKAAERADYMALAIVDG    1840
                         *** **  **************************  ***:*****:
                         ******* sp|O00468|AGRIN_HUMAN    HLQLSYNLGSQPVVLRSTVPVNTNRWLRVVAHREQREGSLQVGNEAPVTG    1998
sp|P25304|AGRIN_RAT      HLQLSYDLGSQPVVLRSTVKVNTNRWLRIRAHREHREGSLQVGNEAPVTG    1890
                         ****:******** ****: :************* sp|O00468|AGRIN_HUMAN    SSPLGATQLDTDGALWLGGLPELPVGPALPKAYGTGFVGCLRDVVVGRHP    2048
sp|P25304|AGRIN_RAT      SSPLGATQLDTDGALWLGGLQKLPVGQALPKAYGTGFVGCLRDVVVGHRQ    1940
                         ********************  :**** ******************::

sp|O00468|AGRIN_HUMAN    LHLLEDAVTKPELRPCPTP                                  2067    SEQ ID NO: 1
sp|P25304|AGRIN_RAT      LHLLEDAVTKPELRPCPTP                                  1959    SEQ ID NO: 2
```

In one example, the antibody may include, but is not limited to, MAb5204 antibody and D2 antibody. Fragments recognized by MAb5204 antibody is as follows:

(SEQ ID NO: 3)
EIPAPETLDSRALFSEKALQSNHFELSLRTEATQGLVLWIGKAAERADY
MALAIVDGHLQLSYDLGSQPVVLRSTVKVNTNRWLRIRAHREHREGSLQ
VGNEAPVTGSSPLGATQLDTDGALWLGGLQK (SEQ ID NO: 4)
LLEDAVTKPELRPC

Fragment recognized by D2 antibody is as follows:

(SEQ ID NO: 5)
LPVGQALPKAYGTGFVGCLRDVVVGHRQLH

Thus, in one example, the antibody as described herein may bind to or recognise an antigen of or epitope having a sequence selected from the group consisting of SEQ ID NO: 1, SEQ ID NO: 2, SEQ ID NO: 3, SEQ ID NO: 4, and/or SEQ ID NO: 5.

The term "epitope" or "antigen" is used interchangeably in the present disclosure to refer to the portion of a substance or target that an antibody or targeting moiety binds. An antigen is characterised by its ability to be "bound" by the antibody or targeting moiety. Antigen can also mean the substance used to elicit the production of targeting moieties, such as the production of antigen specific antibodies through immunising with the antigen.

In one example, the antibody may functionally block the binding of Agrin to Lrp4-muscle specific receptor tyrosine kinases (MuSK). In another example, the antibody may functionally block the binding of Agrin to Lipoprotein related receptor 4 (Lrp4) and muscle specific receptor tyrosine kinases (MuSK) complex and reduce MuSK tyrosine phosphorylation activity In one example, the antibody may be a monoclonal antibody, a polyclonal antibody, a single chain antibody, a chimeric antibody or any fragment or derivative of such antibodies being still capable of binding the Agrin. As used herein, the phrase "fragments and derivatives" may include, but is not limited to a bispecific antibody, a synthetic antibody, an Fab, F(ab)2 Fv or scFv fragment, or a chemically modified derivative of any of these antibodies. In one example, chemical modifications may include, but is not limited to, those which aim to couple the antibody to a detectable marker or an anti-cytotoxic agent such as anti-cancer agents. In one example, the antibody may be provided as a humanised antibody.

In another aspect, there is provided a pharmaceutical composition comprising the anti-Agrin agent as described herein and a pharmaceutically-acceptable carrier or diluent. In one example, the pharmaceutically-acceptable carrier may include, but is not limited to, a colloidal dispersion system, macromolecular complex, nanocapsule, microsphere, bead, oil-in-water emulsion, micelle, mixed micelle, and liposome. In one example, the pharmaceutically-acceptable carrier or diluent may include, but is not limited to, saline.

In one example, the route of administration may be selected from the group consisting of systemic administration, oral administration, intravenous administration and parenteral administration (such as intraperitoneal administration).

Compositions and formulations for oral administration include powders or granules, suspensions or solutions in water or non-aqueous media, capsules, sachets or tablets. Thickeners, flavouring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Compositions as described herein include, but are not limited to, solutions, pastes, ointment, creams, hydrogels, emulsions, liposome-containing formulations, and coatings. These compositions may be generated from a variety of components that include, but are not limited to, preformed liquids, self-emulsifying solids and self-emulsifying semi-solids.

The formulations as described herein, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions as described herein may be formulated into any of many possible dosage forms including, but not limited to intravenous fluids, tablets, capsules, liquid syrups, soft gels, suppositories, and enemas. The compositions as described herein may also be formulated as suspensions in aqueous, non-aqueous or mixed media. Aqueous suspensions may further contain substances that increase the viscosity of the suspension including, for example, saline, sodium carboxymethylcellulose, sorbitol and/or dextran. The suspension may also contain stabilizers.

The compositions as described herein may additionally contain other adjunct components conventionally found in pharmaceutical compositions. Thus, for example, the compositions may contain additional, compatible, pharmaceutically-active materials such as, for example, antipruritic, astringents, local anaesthetics or anti-inflammatory agents, or may contain additional materials useful in physically formulating various dosage forms of the compositions of the present invention, such as dyes, flavouring agents, preservatives, antioxidants, opacifiers, thickening agents and stabilizers. However, such materials, when added, should not unduly interfere with the biological activities of the components of the compositions of the present disclosure. The formulations can be sterilized and, if desired, mixed with auxiliary agents, e.g., lubricants, preservatives, stabilizers, wetting agents, emulsifiers, salts for influencing osmotic pressure, buffers, colourings, flavourings and/or aromatic substances and the like which do not deleteriously interact with the anti-Agrin agent.

In another aspect, there is provided an anti-Agrin agent for use in therapy.

In one example, the anti-Agrin agent may be administered by parenteral administration, oral, transdermal, sustained release, controlled release, delayed release, suppository, catheter, or sublingual administration. In one example, the parenteral administration may be intravenous, subcutaneous, intraperitoneal, or intramuscular.

In one example, the composition comprising the anti-Agrin agent may be administered in an amount of between any one of about 0.01 µg, 0.05 µg, 0.1 µg, 0.5 µg, 1 µg, 5 µg, 10 µg, 20 µg, 30 µg, 40 µg, 50 µg, 60 µg, 70 µg, 80 µg, 90 µg, 100 µg, 110 µg, 120 µg, 130 µg, 140 µg, 150 µg, 160 µg, 170 µg, 180 µg, 190 µg, 200 µg, 210 µg, 220 µg, 230 µg, 240 µg, 250 µg, 260 µg, 270 µg, 280 µg, 290 µg, 500 µg, 1 mg, 1.5 mg, 2 mg, 2.5 mg, 3 mg, 3.5 mg, 4 mg, 5 mg, 10 mg, 15 mg, 20 mg, 25 mg, 30 mg, 35 mg, 40 mg, 45 mg, 50 mg, 75 mg, 100 mg, 125 mg, 150 mg, 175 mg, 200 mg, 225 mg, 250 mg to any one of about 0.01 µg, 0.05 µg, 0.1 µg, 0.5 µg, 1 µg, 5 µg, 10 µg, 20 µg, 30 µg, 40 µg, 50 µg, 60 µg, 70 µg, 80 µg, 90 µg, 100 µg, 110 µg, 120 µg, 130 µg, 140 µg, 150 µg, 160 µg, 170 µg, 180 µg, 190 µg, 200 µg, 210 µg, 220 µg, 230 µg, 240 µg, 250 µg, 260 µg, 270 µg, 280 µg, 290 µg, 500 µg, 1 mg, 1.5 mg, 2 mg, 2.5 mg, 3 mg, 3.5 mg, 4 mg, 5 mg, 10 mg, 15 mg, 20 mg, 25 mg, 30 mg, 35 mg, 40 mg, 45 mg, 50 mg, 75 mg, 100 mg, 125 mg, 150 mg, 175 mg, 200 mg, 225 mg, 250 mg, 300 mg/kg of body weight of the patient.

In one example, the concentration of the administered composition comprising the anti-Agrin agent may be about 1 to about 100 mg/Kg of body weight of the patient, about 5 to about 100 mg/Kg of body weight of the patient, about 10 to about 100 mg/Kg of body weight of the patient, about 20 to about 100 mg/Kg of body weight of the patient, about 30 to about 100 mg/Kg of body weight of the patient, about 1 to about 50 mg/Kg of body weight of the patient, about 5 to about 50 mg/Kg of body weight of the patient and about 10 to about 50 mg/Kg of body weight of the patient.

As used herein, the term "about", in the context of amounts or concentrations of components of the formulations, typically means+/−5% of the stated value, more typically +/−4% of the stated value, more typically +/−3% of the stated value, more typically, +/−2% of the stated value, even more typically +/−1% of the stated value, and even more typically +/−0.5% of the stated value.

In another aspect, there is provided the use of an anti-Agrin agent in the manufacture of a medicament for treating cancer.

In another aspect, there is provided a kit for carrying the methods as described herein. In one example, the kit may be provided with substances needed to carry out the methods as described herein.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

Examples

Methods and Materials

Cell Lines

The human HCC cell lines Hep3B, HepG2 and Huh-7 cells were purchased from American type cell culture (ATCC, Manassas, Va.) and cultured in recommended media. The immortalized non-tumourigenic human hepatocyte cell line MIHA was kindly gifted by Dr. J. M. Luk (Xu, M. Z. et al. AXL receptor kinase is a mediator of YAP-dependent oncogenic functions in hepatocellular carcinoma. Oncogene 30, 1229-1240, doi:10.1038/onc.2010.504 (2011)). All other cell HCC lines were obtained from Dr. Kam-Man Hui (National Cancer Center, Singapore). Cells were cultured as per standard conditions described previously (Hui, K. M. Human hepatocellular carcinoma: expression profiles-based molecular interpretations and clinical applications. Cancer Lett 286, 96-102, doi:10.1016/j.canlet.2008.11.005 (2009)). MCF10A, MCF7, T47D and Sk-Br3 cells were cultured as described previously (Chan, S. W. et al. A role for TAZ in migration, invasion, and tumourigenesis of breast cancer cells. Cancer Res 68, 2592-2598, doi:10.1158/0008-5472.CAN-07-2696 (2008)).

Patient Data Analysis

Human HCC and matched non-tumour patient samples were obtained from National Cancer Center, Singapore.

Normal liver and HCC tissue array slides were obtained from US Biomax, Inc., (catalogue #BC03116). Plasma of normal individuals and HCC patients were obtained from National Cancer Center, Singapore (NCCS). The internal ethics review boards at the NCCS approved all patient samples collection and analysis.

Antibodies and Reagents

Agrin mouse monoclonal (D2) and anti-GFP antibodies was purchased from Santa Cruz Biotechnology Inc., Santa-Cruz, Calif.), pEGFR, Na+/K+ ATPase, Rab5, Integrin β1, cleaved caspase-3, total FAK, pSrc, Total Src, p-PI3-K, total PI3-K, pAkt, total Akt, pERK1/2, total ERK1/2 obtained from Cell Signaling Technology. EGFR, caveolin-1, Ki67, E-cadherin, Ncadherin and Vimentin antibodies were from BD Biosciences, San Jose, Calif. Glypican-3, Flotillin-1, Arp2/3, pFAK (pY397), Snail-1 and MuSK antibodies were from Abcam. Phospho-tyrosine monoclonal antibody 4G10, Agrin function blocking monoclonal antibody MAb5204, GFP and EGFP antibodies were obtained from Millipore, Billerica, Mass. Agrin polyclonal rabbit antibody, CD-71 hybridoma producing OKT-9 cells and fibronectin were obtained from Sigma, St. Louis, Mo. Pure recombinant Agrin protein was obtained from MyBiosource, Inc, San Diego, Calif. Recombinant CTxB, Alexa 488 and 555 conjugated secondary antibodies were from Molecular Probes, Invitrogen, Carlsbad, Calif.

Tumourigenesis in Nude Mice

Four- to six-week-old female nude mice were inoculated subcutaneously (s.c.) in the left and right hind flanks with $10^7$ cells/ml suspended in matrigel (1:1). Tumour development was monitored over a period of 30-36 days before the mice were sacrificed for further analysis. Tumour volume ($mm^3$) is calculated by the formula $V=L*B2/2$, where V=volume of tumour, L=length of tumour and B=breadth of tumour measured in mm scale. A paired standard students 't-test' was performed for all statistical analysis. All animal care and handling were in compliance with Institutional Animal Care and Use Committee (IACUC) at Institute of Molecular and Cell Biology, A-STAR, Singapore.

Generation of Knockdown Cells, Plasmids and Transfections

A pool of lentiviruses encoding shAgrin and scramble control were purchased from Santa Cruz biotechnology Inc. Viral transduction was performed as per manufacturer's protocol. Briefly, 30 μl of viral particles was used to infect MHCC-LM3 cells along with 0.5 μg/ml polybrene in complete media overnight. Next day, medium was changed and cells were reinfected for 2 h and monitored for 2 more days before selection in media containing puromycin (2 μg/ml) for at-least 2 doubling times. After 3 days, knockdown was verified by a Western blot analysis using Agrin specific antibody.

For siRNA mediated knockdown, ONTARGET plus SMARTpool of siRNA against human Agrin catalogue #375790), EGFR (catalogue #1956) and scramble control were obtained from Dharmacon (Thermo Fischer Scientific). siRNA targeting MuSK were obtained from Ambion Life technologies. Hep3B or MHCC-LM3 cells seeded into 6 well dishes were transfected using RNA-iMAX Lipofectamine 2000 (Invitrogen). A Western blot verifying Agrin knockdown was performed after 72 h post transfection. Full length Agrin-GFP was kindly gifted by Dr. Matthew. P. Daniels, National Institutes of Health, Bethesda, Md., USA (Neuhuber, B. & Daniels, M. P. Targeting of recombinant Agrin to axonal growth cones. Mol Cell Neurosci 24, 1180-1196, doi:S1044743103002835 (2003)). EGFP-FAK and EGFP control vectors were obtained from Addgene.

Biotinylation and Cell Surface Protein Extraction

Cell surface proteins were biotinylated and extracted using the Pierce Cell Surface Protein Isolation kit (Pierce, Ill.) as per manufacturer's protocol. Briefly, indicated cell lines were labeled with 0.25 mg/ml cleavable biotinylation reagent (Sulfo-NHS-SS-Biotin) for 30 min at 4° C. Biotinylation was quenched by adding 2 ml of quenching solution. Post washing, cells were harvested in lysis buffer (Pierce), sonicated in ice for 30 min followed by centrifugation at 10,000 g for 2 min Biotin labeled proteins were affinity purified with streptavidin Agarose and eluted with SDS-PAGE sample buffer (62.5 mM Tris HCl, pH 6.8, 1% SDS, 10% glycerol, 50 mM DTT). Flow through fractions were also analysed for cytosolic proteins and lack of plasma membrane proteins.

Stable Isotope Labeling of Amino Acids in Culture (SILAC) Based Mass Spectrometry Analysis Hep3B and MIHA cells were cultured in DMEM for SILAC (Thermo Fischer) supplemented with 10% dialyzed FBS either containing normal isotopes of L-lysine-($^{12}C_6$ $^{14}N_2$) ($K^0$) and Larginine-($^{12}C_6$ $^{14}N_4$) ($R^0$) ($K^0R^0$-'light') or stable isotope L-lysine-($^{13}C_6$ $^{15}N_2$) ($K^8$) and Larginine-($^{13}C_6$ $^{15}N_4$) ($R^{10}$) ($R^{10}K^8$-'heavy') 'heavy') for at-least six doublings ensuring efficient incorporation of labeled amino acids. Cells were subsequently biotinylated and cell surface proteins were extracted as described above and equal amount of cell lysates from light ($K^0R^0$) and heavy ($R^{10}K^8$) were mixed and separated on a 10% SDS-PAGE. Extracted peptides were subjected to LC-Orbitrap MS analysis (FIG. 1a). Equal amounts of protein lysates from heavy and light biotin labelled cell lysates were mixed and 80 μg protein were separated on a one dimensional gradient (4-12%) Nu-Page Novex Bis-Tris gel (Invitrogen) and digested with trypsin described previously (Swa, H. L., Blackstock, W. P., Lim, L. H. & Gunaratne, J. Quantitative proteomics profiling of murine mammary gland cells unravels impact of annexin-1 on DNA damage response, cell adhesion, and migration. Mol Cell Proteomics 11, 381-393, doi:10.1074/mcp.M111.011205). The samples were analysed on an Orbitrap XL (Thermo Fischer) full scan mass spectra. Identification and quantification of peptides were performed using mascot version 2.2 (Matrix science, London, U.K.) as described previously (Swa, H. L., Blackstock, W. P., Lim, L. H. & Gunaratne, J. Quantitative proteomics profiling of murine mammary gland cells unravels impact of annexin-1 on DNA damage response, cell adhesion, and migration. Mol Cell Proteomics 11, 381-393, doi:10.1074/mcp.M111.011205).

Western Blot Analysis

Indicated cell lines were washed once with ice-cold PBS, lysed in cold lysis buffer (150 mM NaCl, 50 mM Tris-HCl pH 7.3, 0.25 mM EDTA pH 8.0, 1% sodium deoxycholate, 1% Triton X-100, 0.2% sodium fluoride and 0.1% sodium orthovanadate supplemented with protease inhibitor cocktail (Roche Applied Biosciences). Cell lysate was centrifuged at 13,000 rpm for 30 min, boiled in 2× sample buffer, separated on either 7.5%, 10% or 4-20% gradient SDSpolyacrylamide gels and blotted onto nitrocellulose membrane. The membrane was blocked in 5% skimmed milk in PBS containing 0.1% Tween-20, probed with primary antibody followed by appropriate secondary antibody conjugated with horseradish-peroxidase (Pierce) and immunoreactive bands were visualized by enhanced chemiluminescence super signal pico (Pierce).

Immunoprecipitation

Cells were lysed in lysis buffer (20 mM Tris-HCl, pH 7.5, 150 mM NaCl, 1% Triton X-100, and 1 mM PMSF with complete EDTA-free protease inhibitor mixture [Roche]). The lysate was incubated on ice for 30 min and cleared by centrifugation at 13,000 rpm for 30 min at 4° C. Immunoprecipitation was performed at 4° C. with 5 μg of antibody in the presence of either protein A or protein G-Sepharose 4 Fast Flow (GE Healthcare) for 4 h at 4° C. in a rocker. The Sepharose bound proteins was then washed three times with cell lysis buffer and three times with cold PBS. Bound proteins were eluted with 2× Laemmli sample buffer, resolved by SDS-PAGE for subsequent Western blotting.

Agrin ELISA

Secreted Agrin were determined in normal and HCC patient plasma using an Agrin ELISA kit (MyBiosource, Inc). Briefly, 50 μl of provided Agrin standard or diluted plasma were added to 96-well plates coated with Agrin antibodies. 100 μl of secondary antibody conjugated to HRP were then added to the wells and incubated for 1 h at 37° C. Post-washing, 100 μl substrate solution was added to each well followed by 50 μl stop solution. Absorbance was measured at 450 nm wavelength using a spectrophotometer. Agrin protein levels were calculated from a standard curve. Each patient samples were analysed in quadruplex. Error bar represents standard error of deviation for each sample.

Cytosolic Soluble and Membrane Fractionation

Cells were harvested in homogenization buffer (20 mM Tris-HCl, pH 7.5, 150 mM NaCl, and 1 mM PMSF with complete EDTA-free protease inhibitor mixture [from Roche]). The cell suspension homogenized through a 29G needle 10 times on ice. The cell lysate was briefly centrifuged at 2,000 rpm for 5 min at 4° C. The clarified lysate was then subjected to centrifugation at 80,000 rpm using the TLA120.1 rotor (Beckman Coulter) for 1 h at 4° C. Cytosol was collected and the membrane pellet was washed once with cytosol buffer and then centrifuged at 80,000 rpm for 30 min at 4° C. once more using the TLA120.1 rotor. The membrane pellet was dissolved in lysis buffer and centrifuged again at 80,000 rpm using the TLA120.1 rotor for 1 h at 4° C. for the third time. The solubilized membrane proteins were then collected. The proteins were resolved by SDS-PAGE subjected to Western blot analysis.

Lipid Raft/Caveolae Membrane Isolation

Lipid raft/caveolae extraction was performed as per the instructions of Lipid raft/Caveolae isolation kit (Sigma) and previously published protocols (Chakraborty, S., ValiyaVeettil, M., Sadagopan, S., Paudel, N. & Chandran, B. c-Cbl mediated selective virus-receptor translocations into lipid rafts regulate productive Kaposi's sarcoma-associated herpesvirus infection in endothelial cells. J Virol 85, 12410-12430, doi:10.1128/JVI.05953-11). Briefly, confluent indicated cell lines were lysed in 0.5M sodium bicarbonate lysis buffer (pH 11.0) containing protease inhibitor cocktail (Roche) for 15 min on rocker. Cell lysate were homogenised in a Dounce homogenizer (10 strokes), followed by sonication for 10 sec at 4° C. A discontinuous gradient (0-35%) of optiprep and lysis buffer was made and two ml of cell lysate and optiprep (35%) was placed at the bottom of a pre-cooled centrifuge tube, with each layer pre-ceding on top. The tubes were centrifuged at 40,000 rpm for 4 h using a Beckmann SWI-55 rotor. One ml fractions were collected from the top and analysed by Dot and Western blots.

Agrin Internalization Assay

Hep3B cells were seeded in 8 well chamber slides (Nalge Nunc., Inc.,). 70-80% confluent cells were treated with 3 μg/ml Agrin antibody (Santa Cruz Biotechnology, Inc.,) and 0.5 μg/ml Cholera toxin B subunit (CTxB) conjugated with Alexa 488 (green) in chilled complete medium for 1 h at 4° C. on ice. Subsequently, the antibody was washed away and cells were replenished with complete media for indicated time points at 37° C. Cells were fixed after indicated time points with 4% Paraformaldehyde (PFA) for 15 min at room temperature and processed for immunofluorescence analysis using appropriate secondary Alexa fluor-labeled antibodies (Molecular probes, Invitrogen).

Immunofluorescence Microscopy

Cells grown either on coverslips (Thermo Fisher Scientific) or 8 well chamber slides (Nalge Nunc, Inc.,) were washed two times with PBS supplemented with 1 mM $CaCl_2$ and 1 mM $MgCl_2$ (PBSCM). They were fixed with 4% paraformaldehyde in PBSCM for 15 min at room temperature. The fixed cells were washed five times at 5-min intervals using PBSCM and then permeabilized with 0.1% Triton X-100 in PBSCM for 5 min at room temperature. The cells were then immunostained with appropriate primary antibodies diluted in fluorescence dilution buffer (FDB; PBSCM with 5% FBS and 2% bovine serum albumin [BSA]) for 1 h at room temperature. The coverslips were then washed five times with 0.1% Triton X-100 PBSCM at 5-min intervals. Secondary antibodies conjugated to either Alexa 488 (green) or Alexa 595 (red) were diluted appropriately in FDB and incubated at room temperature for 1 h. The coverslips were washed again with 0.1% Triton X-100 PBSCM five times for 5-min each and then twice with PBSCM. The coverslips were mounted on microscopic slides with Vectashield mounting medium containing DAPI (Vector Laboratories). Confocal microscopy was performed with either an Axioplan II microscope (Carl Zeiss, Inc.) equipped with Zeiss confocal scanning optics or Olympus Fluoview 1000 confocal microscope (Olympus).

Immunohistochemistry

Paraffin embedded tissue sections were deparaffinised in Bond™ Dewax solution, rehydrated through 100% ethanol to 1× Bond Wash solution, antigenic epitope retrieval performed at pH 6.0 and blocked in 10% goat serum for 30 min Slides were then incubated with primary antibodies in Bond diluent solution for 45 min, washed three times in wash buffer, polymerized for 10 min and subsequently washed again for at-least four times. Nuclei were counterstained with haematoxylin for 5 min, rinsed in deionized water and mounted in mounting medium. Slides were visualized under a bright field microscope using Leica imaging software.

Live Cell Invadopodia Imaging

Control or Agrin shRNA transduced MHCC-LM3 cells were cultured in glass bottom petridishes (MatTek Corporation) for 12-16 h before imaging live at 37° C. using the Differential Interference Contrast (DIC) filter in a confocal microscope (Olympus). Data were analysed using the Fluoview software.

Wound-Healing Assay

Cell migration was assessed by wound-healing assays. Briefly, confluent MHCC-LM3 cells either transduced with control shRNA or Agrin shRNA plated on 6 well culture dishes were wounded by manual scratching with a 200 μl pipette tip. Subsequently, cells were washed with PBS and incubated at 37° C. in complete media. At the indicated time points, phase contrast images at specific wound sites were taken.

Anchorage-Independent Growth in Soft Agar 1.5 ml of 0.5% agar (electrograde ultra-pure; Invitrogen, Carlsbad, Calif.) supplemented with DMEM, 10% FBS, were plated in six-well culture dishes as bottom agar. Three thousand cells were mixed with 1.5 ml of 0.35% agar supplemented with DMEM, 10% FBS and plated on top of bottom agar. 1 ml media was added on top of solidified agar layers and colonies were allowed to grow in incubator at 37°

C. for a span of 12 days. Images of cell colonies were observed in an inverted microscope.

Matrigel Cell Invasion Assay (Transwell Assay)

Cell invasion was determined using the 24-well chambers with 8 µm pore polycarbonate membranes pre-coated with a thin layer of Matrigel Basement Membrane Matrix (BD Biosciences). The chambers were rehydrated in serum free medium as per the manufacturer's protocol. Complete medium with 10% FBS (700 µl) served as chemo-attractant in the bottom chamber and $1 \times 10^4$ cells/ml cells were incubated for 24 h at 37° C., 5% $CO_2$. At the end of incubation period, cells invading matrigel were washed and stained with 0.05% crystal violet solution and imaged in a bright field microscope.

Fibronectin Adhesion Assay

Briefly, culture plates were coated with 10 µg/ml fibronectin for 1 h at 37° C. Either control or Agrin knockdown cells ($2 \times 10^3$ cells/ml) were trypsinized and plated on coated dishes. Adhered cells were analysed either by live cell imaging for morphological changes at indicated time-points or lysates were collected and subjected to Western blot analysis.

Microarray Data Mining and Gene Expression Analysis

Hepatocellular carcinoma microarray datasets containing normal and HCC patient samples (Oncomine) (Roessler, S. et al. A unique metastasis gene signature enables prediction of tumour relapse in early-stage hepatocellular carcinoma patients. Cancer Res 70, 10202-10212, doi:10.1158/0008-5472.CAN-10-2607 (2010); Wurmbach, E. et al. Genome-wide molecular profiles of HCV-induced dysplasia and hepatocellular carcinoma. Hepatology 45, 938-947, doi: 10.1002/hep.21622 (2007)) were analysed. Since all of them were assayed on Affymetrics human-UG133 platform, the mean expression of Agrin using AGRN 212285_s_at as query was determined. Microarray data are pre-processed by Oncomine in a standardized way by log 2 transformation and scaling the median value per microarray to 0.

Statistical Analysis

All experiments were performed in triplicates. Histograms and bar charts represent mean values and error bar indicates standard error of deviation (+/−SD), unless stated otherwise. A paired two-tailed student's 't-test' was performed and data were considered statistically significant when $p<0.05$.

Results

Figure 9:
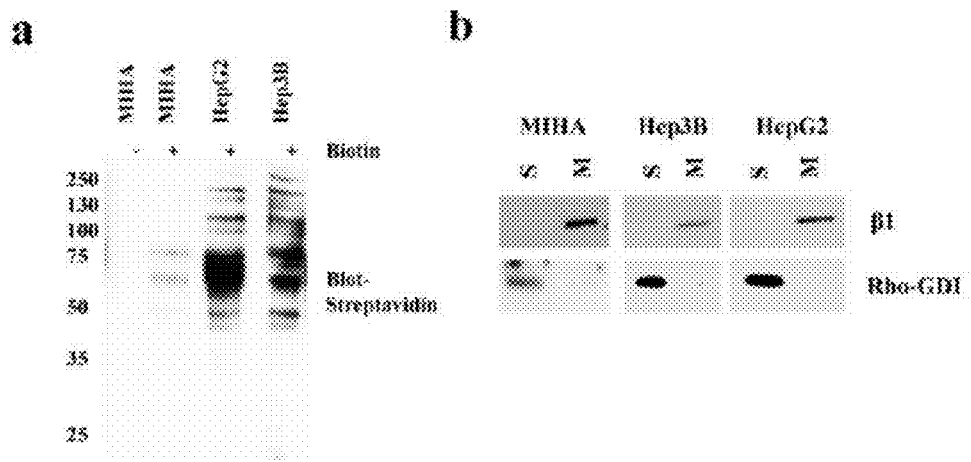
FIG. 9 shows characterization of cell surface biotinylation in non-tumourigenic and tumourigenic HCC cell lines. In particular, (a) shows Western blot analysis of indicated cell lines, which were either mock or surface biotinylated, cell membrane fractions enriched and affinity purified using streptavidin-A beads and analysed using a streptavidin antibody; (b) shows characterization of purity of cell membrane and cytosolic soluble purified fractions. Integrin (31 and Rho-GDI are markers for membrane and soluble fractions, respectively. Thus, FIG. 9 shows proteoglycan Agrin was also identified as an overexpressed surface protein in Hep3B cells.

Quantitative Identification of Differentially Expressed Surface Proteins in Hepatoma Cell Line Hep3B by SILAC Mass Spectrometry To identify potential diagnostic and/or therapeutic targets differentially expressed during hepatocellular carcinoma, biotinylated cell surface proteins enriched for plasma membrane fractions were affinity purified with streptavidin sepharose beads. Hep3B, HepG2 (HCC cell lines) and non-tumourigenic liver MIHA cells were used for the experiment. Compared to MIHA cells, significant numbers of surface biotinylated proteins enriched in both HCC cell lines (FIG. 9a) was observed. The enrichment of plasma membrane fractions were confirmed by examining the distribution of a membrane marker (integrin β1) and cytosolic marker (Rho-GDI) (FIG. 9b). For quantitative evaluation, biotinylation and extraction of cell surface proteins were combined and identified by employing Stable Isotope Labeling of Amino acids in Culture (SILAC) based quantitative mass spectrometry (See workflow in FIG. 1a). To increase the confidence of protein quantification, only the proteins with at least two ratio counts were considered for follow-up analysis. A protein density plot was generated using the ratios of those quantified proteins to determine the thresholds for clustering differentially expressed proteins. Using 10%, 90% and in between quantile-based thresholds the proteins were categorized as down-, up- and unregulated proteins, respectively (FIG. 1b). In this study, the study focussed on proteins that are overexpressed in Hep3B cells and can potentially be targeted in liver carcinoma (red cluster, FIG. 1b). As such, the up-regulated protein cluster (data not shown) was subjected to Gene Ontology Cellular Component analysis using GeneGO program. This analysis revealed that over 50% of up-regulated proteins are enriched as plasma-membrane proteins (FIG. 1c and data not shown). The overexpressed proteins including Epidermal growth factor receptor (EGFR), Glypicans and Epithelial cell adhesion molecule (EpCAM) have wide spread roles in numerous cancers, thereby displaying the authenticity of the SILAC screen as described herein. Proteoglycan Agrin was also identified in this screen as an overexpressed surface protein in Hep3B cells (data not shown).

Biochemical Validation of a Selected Set of Proteins Differentially Expressed in HCC Cell Lines To confirm the mass spectrometry findings as discussed above, biotinylated surface proteins in MIHA and Hep3B cells were affinity purified and the expression levels of selected candidate(s) were detected in Western blot analysis. Consistent with the SILAC observations discussed above, Agrin, EpCAM, EGFR and Glypican-3 showed increased cell surface expression in Hep3B compared to MIHA cells (FIG. 1d). Moreover, significant increases in expression of these proteins were also evident in the whole cell lysates of HCC cell lines (FIG. 1d). Conversely sorting nexin-5 (SNX5), a protein indicated to be down-regulated in Hep3B cell surface was also verified by Western blot analysis (FIG. 1d). The sodium/potassium pump (Na+/K+ ATPase), a plasma membrane protein and many other transporter proteins with unaffected SILAC ratios also did not show significant change between MIHA and Hep3B cells in Western blot analysis (FIG. 1d). β-actin indicates equal loading of whole cell lysates (FIG. 1d).

Agrin is Over-Expressed and Secreted in HCC Cell Lines

Among the identified molecules, the present disclosure considered Agrin as an attractive target in HCC due to its reported accumulation in rat liver cirrhosis and induced HCC but with little known role in HCC. Agrin was also well expressed in a panel of HCC cell lines with relatively higher levels in metastatic MHCC-97H, MHCC-LM3, Sk-HEP-1 and SNU-449 cells (FIG. 1e). Increased Agrin expression in selected breast carcinoma cell lines with elevated EGFR expression was also observed (FIG. 1e). Notably, Agrin expression in non-tumourigenic MIHA and MCF10A cells remained low when compared to the cancer cell lines (FIG. 1e).

Figure 10:
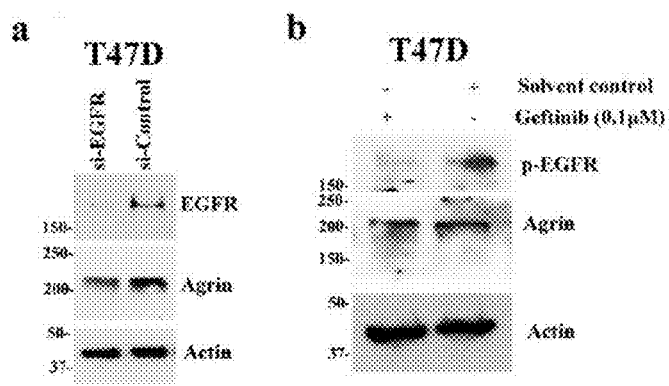
FIG. 10 shows the effect of Epidermal growth factor receptor (EGFR) inhibition on Agrin expression in breast cancer cell lines. In particular, (a and b) shows Western blot analysis of T47D cells, which were either transfected with control or EGFR siRNAs (a) or treated with DMSO control or 0.1 µM Geftinib for 12 h (b). 72 h post-transfection (a) or 12 h post inhibitor treatment (b), cells were lysed and Western blotted for the indicated proteins. Thus.

Over-expression of Agrin in EGFR enriched breast carcinoma cell lines, in the context that the SILAC data described herein indicates EGFR overexpression in Hep3B cell surfaces and the sheer presence of EGF binding motifs in Agrin10, prompted further examination on whether the expression of Agrin was dependant on EGFR. However, EGFR depletion in T47D cells (breast carcinoma cell line with high EGFR and Agrin expression) did not affect Agrin expression (FIG. 10a). Similarly, EGFR inhibitor Geftinib reduced EGFR phosphorylation (pY1045) without affecting Agrin expression in T47D cells (FIG. 10b). These observations clearly suggest that Agrin expression is independent on EGFR.

Since neural Agrin is secreted at nerve terminals to facilitate aggregation of Acetylcholine receptors (AchR) for efficient nerve impulse transmission, the present disclosure next examined whether it is also secreted in cancer cell lines and hence can act as an important bio-marker and therapeutic target. Accordingly, the supernatants of HCC cell lines (MHCCLM3 and Hep3B), a breast cancer cell line SkBr-3 and non-tumourigenic MIHA cells were tested for Agrin secretion. Indeed, Agrin secretion was high in HCC cell supernatants, low in SkBr-3 and not detected in MIHA cells (FIG. 1f).

In vivo, mouse xenografts also showed a higher expression of Agrin in the liver (Hep3B) tumours compared to MCF7 cell breast carcinoma (FIG. 1g). These results taken together suggest that Agrin is preferentially over-expressed in HCC cell lines and their xenografts.

Agrin is Enriched in Lipid Rafts and is Constitutively Internalized

Figure 2:
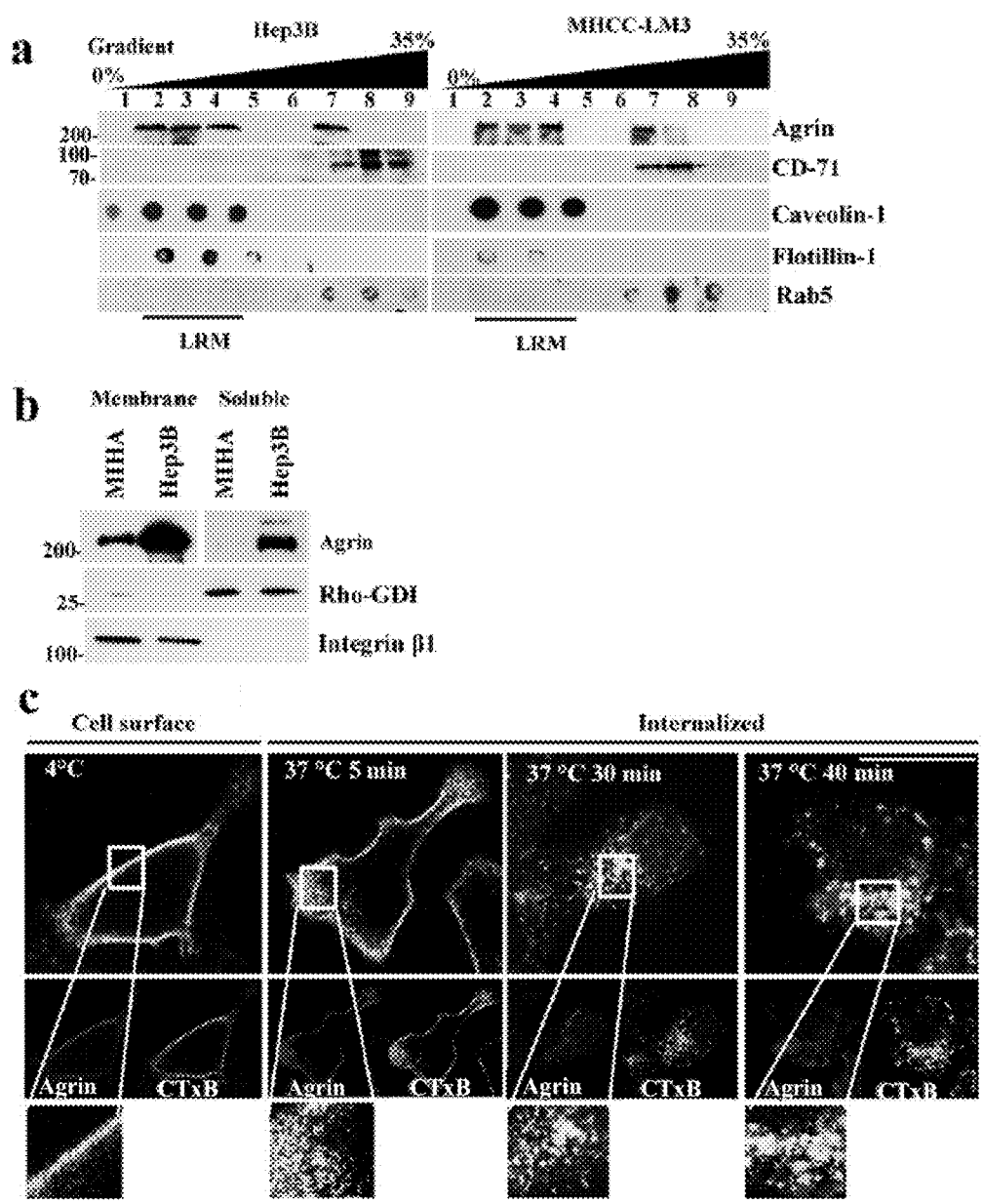
FIG. 2 shows localization and constitutive internalization of Agrin in hepatocellular carcinoma (HCC) cell lines. In particular, (a) shows the biochemical density gradient fractions from the indicated cell lines that were analysed by Western blot for Agrin. Caveolin-1 and Flotillin-1 are markers for lipid raft membrane (LRM) and caveolae rich domains, CD-71 marks high density non-lipid raft domains of plasma membranes and Rab-5 marks the early endosomal vesicles containing fractions; (b) shows Agrin expression as observed with Western blotting of membrane and soluble fractions from MIHA and Hep3B cells that were isolated as described in materials and methods. Rho-GDI and Integrin β1 served as markers for soluble and membrane fractions, respectively; (c) shows an immunofluorescence assay result of Hep3B cells, which were treated with Agrin antibody and recombinant Alexa 488 labelled cholera toxin B (CTxB) for 1 h at 4° C., and allowed to internalize at 37° C. for the indicated time-points, fixed and processed for immunofluorescence assay. Representative confocal images of internalization assay are shown. Boxed areas represent enlarged panels. Scale bar: 10 μm; (d) shows line scan signal intensity plots for the indicated cells at 4° C. (cell-surface) and 37° C. (internalized) are shown; (e) shows immunofluorescence assay result of Hep3B cells, which were incubated with Agrin antibody as in (c) and allowed to internalize for indicated time-points. 4% PFA fixed cells were immunostained with an anti-EEA-1 antibody for 1 h at room temperature (RT), followed by anti-mouse Alexa 594 and anti-rabbit Alexa 488 secondary antibodies. Representative confocal images are shown. Boxed areas are represented as enlarged panels. Scale bar: 10 μm; and (f) shows a bar graph of the quantification of internalized Agrin colocalized with EEA-1 at indicated time-points measured by the number of colocalizing cells per field. At least five fields containing at least 10 cells per field were chosen.
Figure 2:
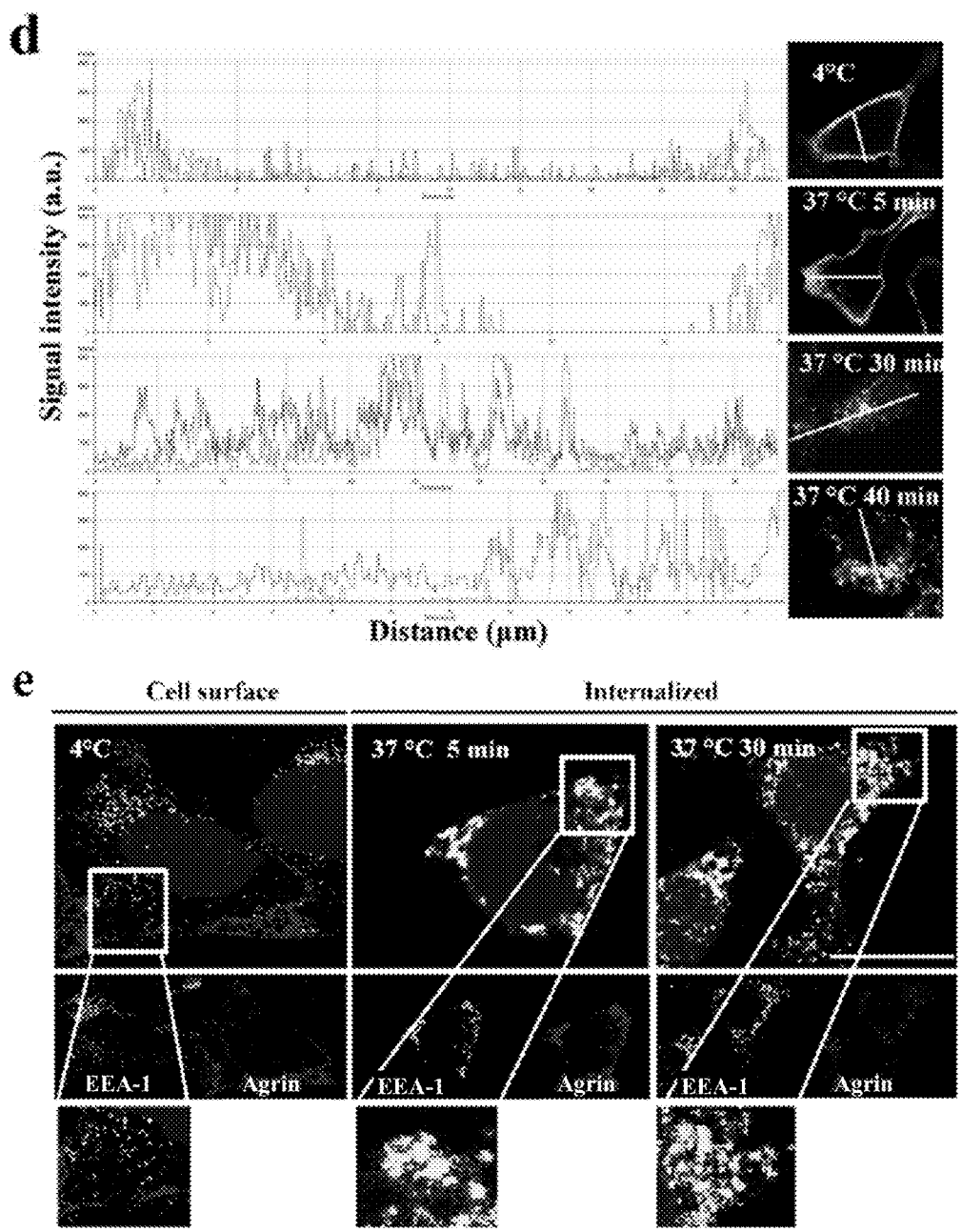
Figure 2:
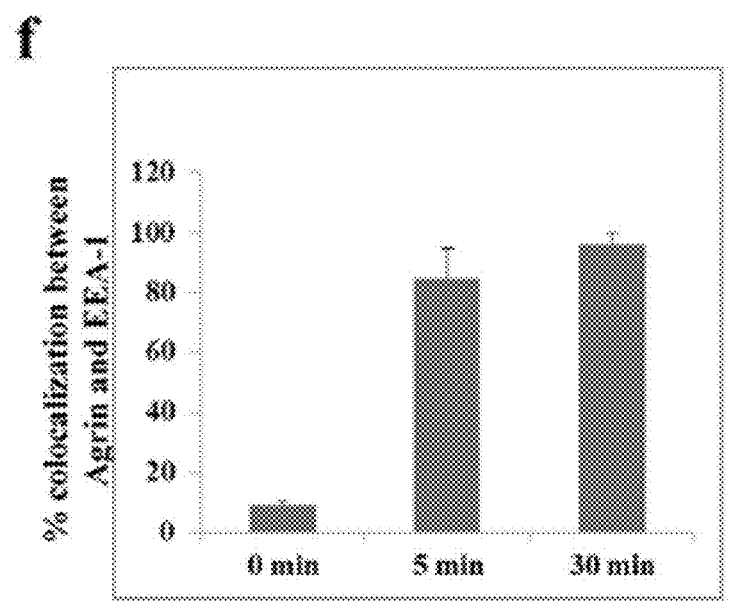

Receptors or ligands preferentially localized in lipid raft membranes are internalized into intracellular compartments resulting in efficient amplification of signaling in cancer. Reported lipid raft localization of neural Agrin at nerve terminals prompted us to examine the exact membrane localization of Agrin in HCC cell lines. Biochemical lipid raft fractionation of Hep3B and MHCC-LM3 cell lines revealed that bulk of cell-associated (representing those bound to the cell surface) Agrin is indeed localized to Caveolin-1 and Flotillin-1 enriched lipid raft membranes (LRM), while a sub-population of it remained associated with endosomal and high density fractions marked by Rab5 and CD-71, respectively (FIG. 2a). Membrane and soluble fractions of MIHA and Hep3B cells also revealed that, in contrast to MIHA cells expressing low amounts of membrane associated Agrin, Hep3B cells exhibited robust Agrin expression in both membrane and soluble fractions of Hep3B cells (FIG. 2b). Integrin β1 and Rho-GDI marked the membrane and soluble fractions, respectively. The soluble Agrin may represent those loosely associated with the endosomal membrane or secreted.

The presence of Agrin in soluble fractions raised the question whether it is constitutively internalized in HCC cell lines similar to many ligands and receptors. An Agrin antibody internalization assay was performed to test this. At 4° C., Agrin antibody was bound to Hep3B cell surfaces and colocalized with Cholera toxin-B subunit (CTxB), known to bind surface GM1 monosialoganglioside in lipid rafts (FIGS. 2c and 2d, first panels). After 5 min of internalization at 37° C., Agrin antibody was observed to be co-internalized with CTxB with coherent signal intensity overlaps projected towards intracellular compartments (FIGS. 2c and 2d, second panel). By 30 and 40 min of internalization, respectively, both Agrin and CTxB were observed in internal organellar compartments, supported by coherent intracellular signal overlaps (FIGS. 2c and 2d, third and fourth panels). This phenomenon is also verified by the presence of internalized Agrin in EEA-1 positive early endosomes from 5 min till the observed 30 min incubation at 37° C. (FIGS. 2e and 2O. Therefore, these observations suggest that lipid raft localized Agrin is actively internalized in HCC cell lines.

Agrin Depletion Inhibits Growth and Proliferation of HCC Cell Lines

Figure 3:
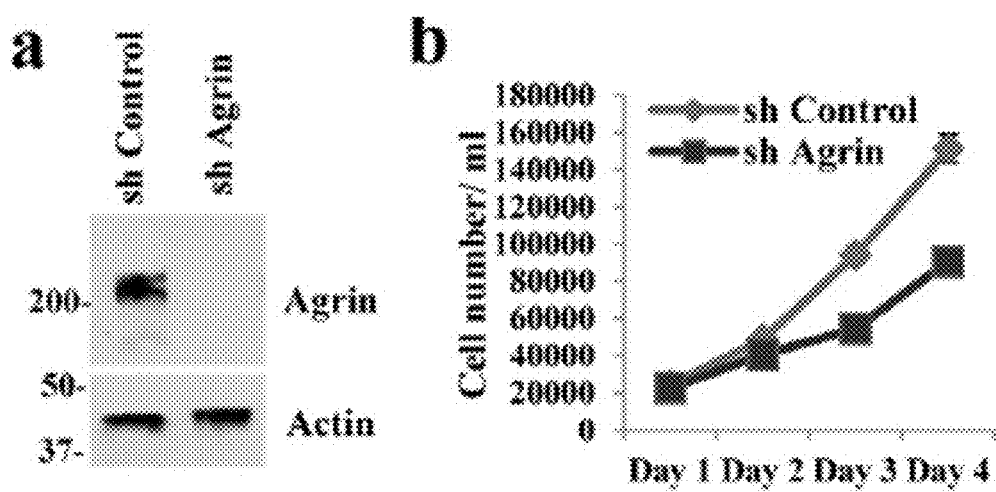
FIG. 3 shows Agrin knockdown effects on cell growth and apoptosis. In particular, (a) shows Western blot validation of the knockdown of Agrin in MHCC-LM3 cells transduced with either control or short hairpin Agrin RNA (i.e. shAgrin or Agrin shRNA) expressing lentiviral particles; (b) shows the proliferation measured by total cell count of Control and Agrin shRNA transduced MHCC-LM3 cells when passaged in the indicated days; (c) shows a representative image of bright field microscopy morphology analysis of Control and Agrin shRNA transduced MHCC-LM3 cells. Scale bar: 10 μm; (d) shows a bar graph representing the results of the proliferation assay of MIHA cells expressing either Agrin GFP or control GFP after 72 h post-transfection. Culture media from the above transfected cells were incubated with MIHA cells for 1 day before analysing cell proliferation by crystal violet staining and measuring absorbance at 590 nm; (e) shows a representative confocal images of control shRNA and shAgrin transduced MHCC-LM3 cells, which were immunostained with Ki67 (nuclear proliferation marker) antibody and counterstained with DAPI. Arrows in the enlarged panel indicate actively proliferating cell nuclei. Scale bar: 10 μm; (f) shows representative images of shControl or shAgrin MHCC-LM3 cells, which were analysed for apoptosis using Annexin-V apoptosis staining kit. Representative images co-stained with DAPI are shown and enlarged area depicts a typical AnnexinV stained apoptotic cell. Quantitative plot depicting the percentage of apoptotic cells in at-least five different microscopic fields are also shown. Scale bar: 10 μm. (P value=0.005); (g) shows Western blot analysis of cleaved Caspase-3 in shControl and shAgrin MHCC-LM3 cells. The blots were stripped and probed for Agrin and β-actin. Immunofluorescence analysis for the expression of cleaved caspase-3 (red) and DAPI (blue) in control and Agrin shRNA transduced MHCC-LM3 cells. Scale bar.
Figure 3:
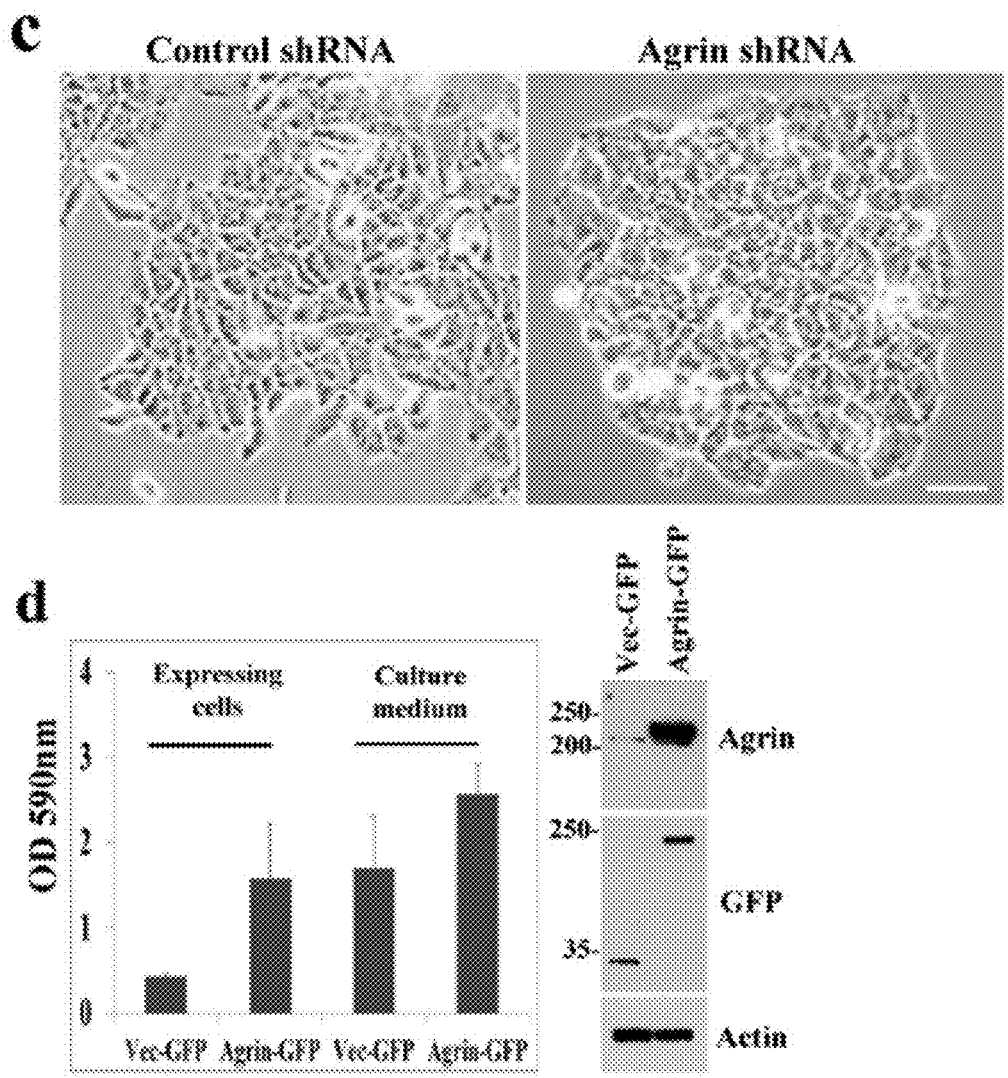
Figure 3:
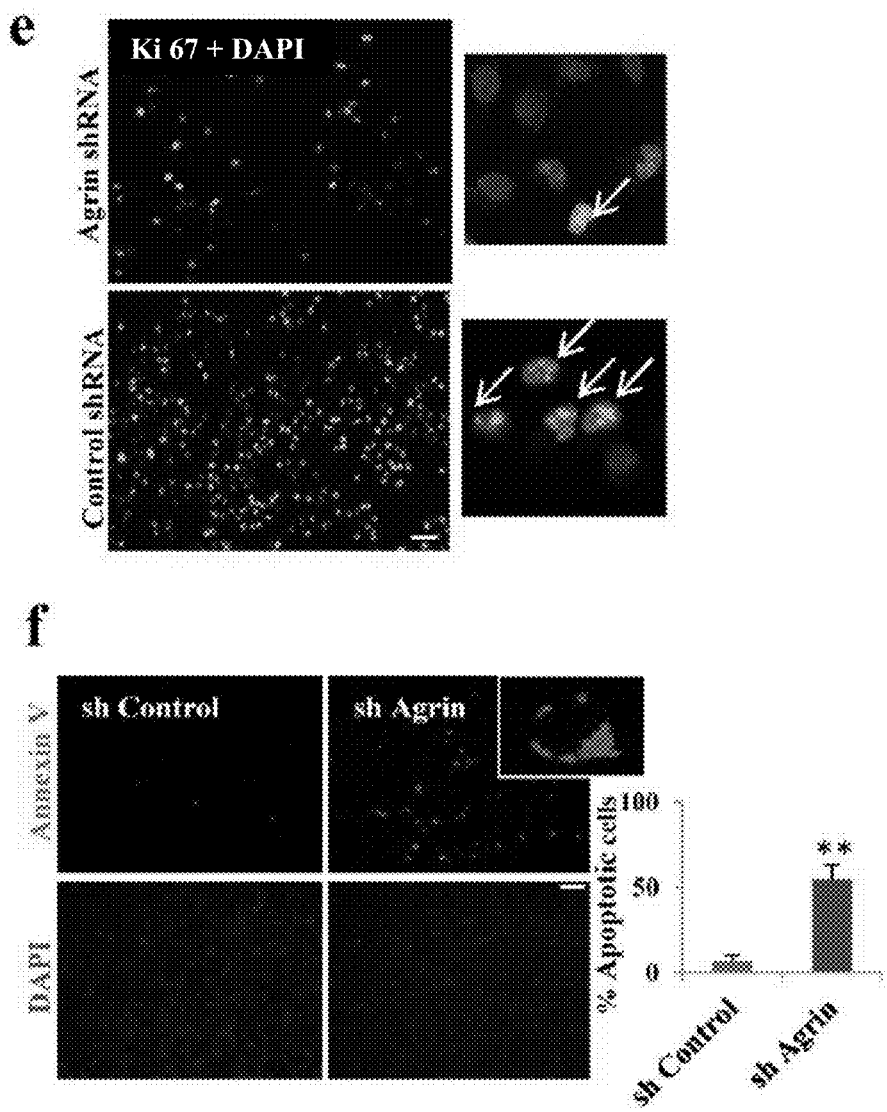
Figure 3:
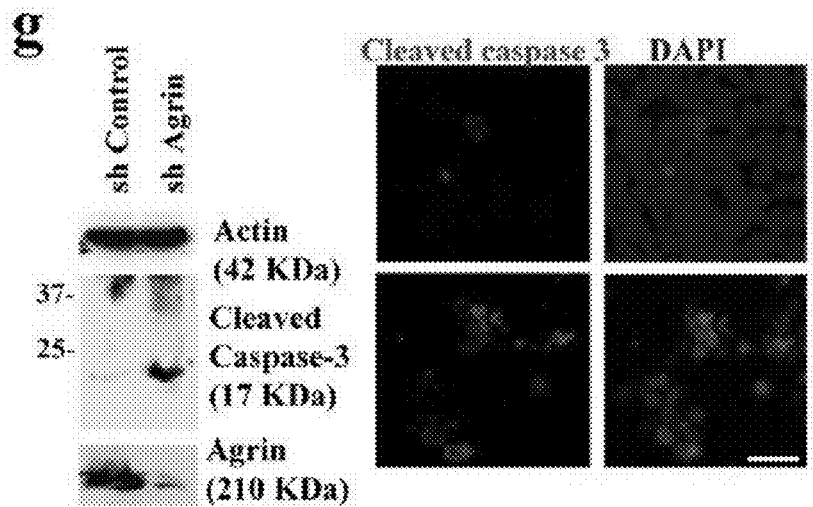
Figure 11:
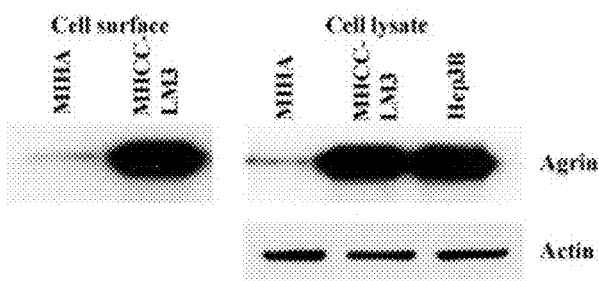
FIG. 11 shows cell surface expression of Agrin in MHCC-LM3 cells. Surface biotinylated or whole cell lysate from indicated cell lines were subjected to a Western blot using Agrin antibody. Actin served as loading control for whole cell lysates.
Figure 12:
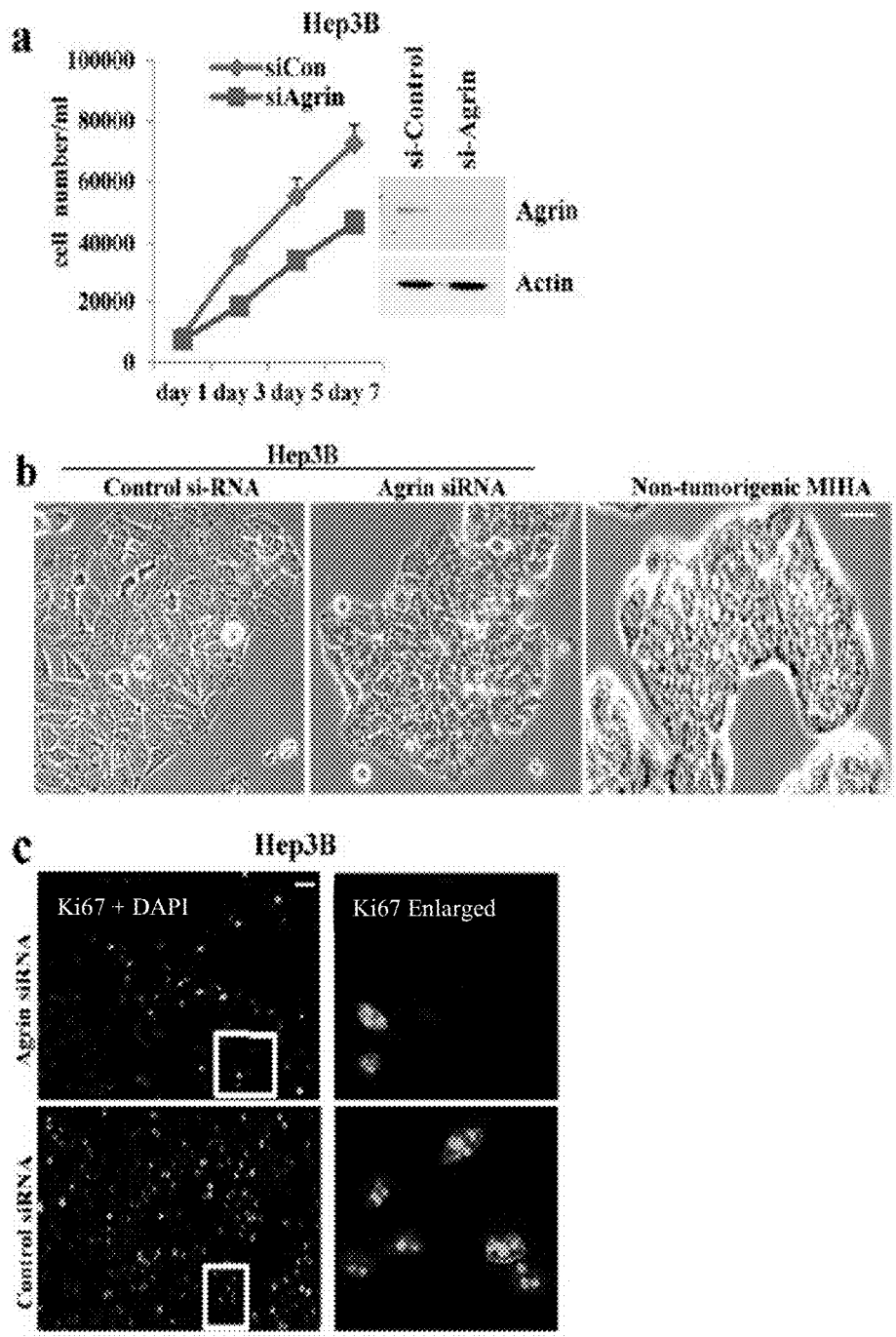
FIG. 12 shows anti-tumourigenic effects of siRNA mediated Agrin knockdown in Hep3B cells. In particular, (a) shows a graph of the result of an assay where Hep3B cells transfected with either control or Agrin siRNA were cultured for the indicated number of days. At each time-point, cells were trypsinized and total cell count was measured by a cell counter apparatus as an index of proliferation. 72 h post-transfection, cell lysates were collected and analysed for Agrin knockdown; (b) shows representative bright field microscope images of the morphology of control and Agrin siRNA transfected Hep3B cells 72 h post-transfection. Scale bar: 10 µm; (c) shows representative images of control or si-Agrin transfected Hep3B cells, which were immunostained with mouse Ki67 antibody followed by anti-mouse secondary antibody conjugated with Alexa fluor 488. Representative images merged with DAPI stain are shown. Boxed region represents the enlarged panel with nuclear Ki67 staining. Scale bar: 10 µm; (d) shows Western blot analysis for cleaved caspase-3 in control and Agrin siRNA transfected Hep3B cells; (e) shows results of an assay where Hep3B cells were transfected with control or Agrin siRNA. 48 h post-transfection, cells were subjected to a modified Boyden chamber matrigel invasion assay. Invasive cells were fixed in 4% PFA after 24 h, stained with 0.1% crystal violet solution in ethanol and visualized in a bright-field microscope under 20× magnification. Images were quantified using the ImageJ software and represented in a graph. Error bar represents mean standard deviation of three biological replicates.
Figure 12:
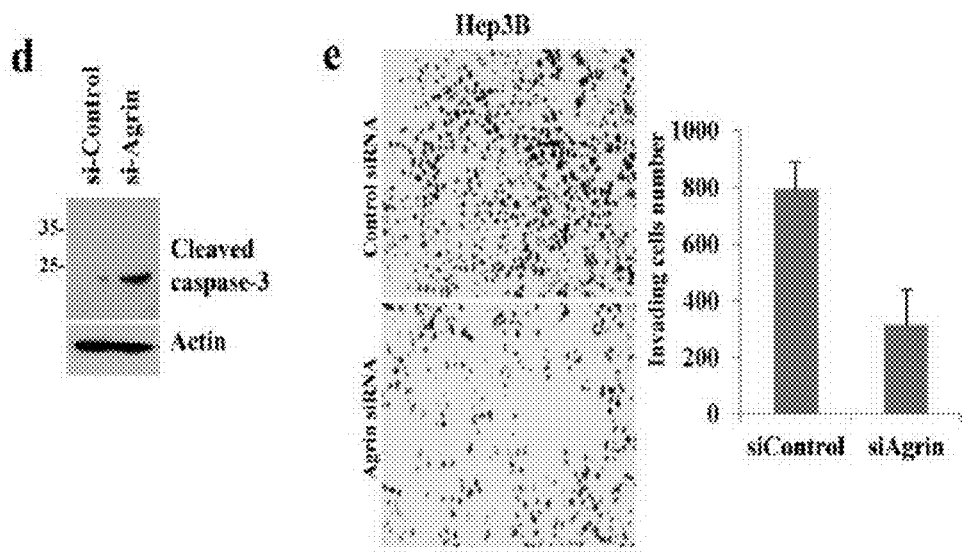

To characterize the functional role of Agrin in HCC, Agrin were knocked down either by stably transducing with Agrin shRNA lentiviruses or transfecting a different siRNA pool targeting Agrin in MHCC-LM3 or Hep3B cells, respectively. MHCC-LM3 was chosen in addition to Hep3B cells as they are highly metastatic and efficient in tumour formation in vivo. Additionally, like Hep3B cells, cell surface expression of Agrin in MHCC-LM3 cells was significantly high compared to MIHA cells (FIG. 11). Agrin knockdown were very efficient in HCC cell lines (FIGS. 3a and 12a). Compared to the control cells, Agrin depletion inhibited cellular proliferation (FIGS. 3b and 12a). Morphologically, Agrin depletion transformed the elongated phenotype of control cells to a cobblestone shape with tighter cell-cell contacts in MHCC-LM3 and Hep3B cell-lines, similar to non-tumourigenic MIHA cells (FIGS. 3c and 12b). Additionally, MIHA cells overexpressing Agrin-GFP showed enhanced proliferation than those having expressing vector alone (FIG. 3d). Interestingly, culture media from Agrin over-expressing but not vector control cells, also promoted growth in naïve MIHA cells (FIG. 3d), suggesting the notion that secreted Agrin is the functional form. Significant reduction of proliferation marker Ki67 labeling in Agrin knockdown cells further suggests a possibility of growth arrest upon Agrin depletion in HCC cell lines (FIGS. 3e and 12c).

The present disclosure examined whether growth arrest due by Agrin depletion is also associated with increased apoptosis in addition to decreased proliferation as evidenced by reduced labelling of Ki67. Compared to control cells, greater than 50% apoptosis were observed in Agrin knockdown cells, as indicated by AnnexinV staining (FIG. 3f). Similarly cleaved caspase-3 (late phase apoptosis marker) was elevated in Agrin depleted MHCC-LM3 and Hep3B cells (FIGS. 3g and 12d). Together, loss-of-functional Agrin reduced cell proliferation and induced apoptosis in HCC cell lines.

Agrin Depletion Affects Cell Migration, Invasiveness and Colony Formation

Figure 4:
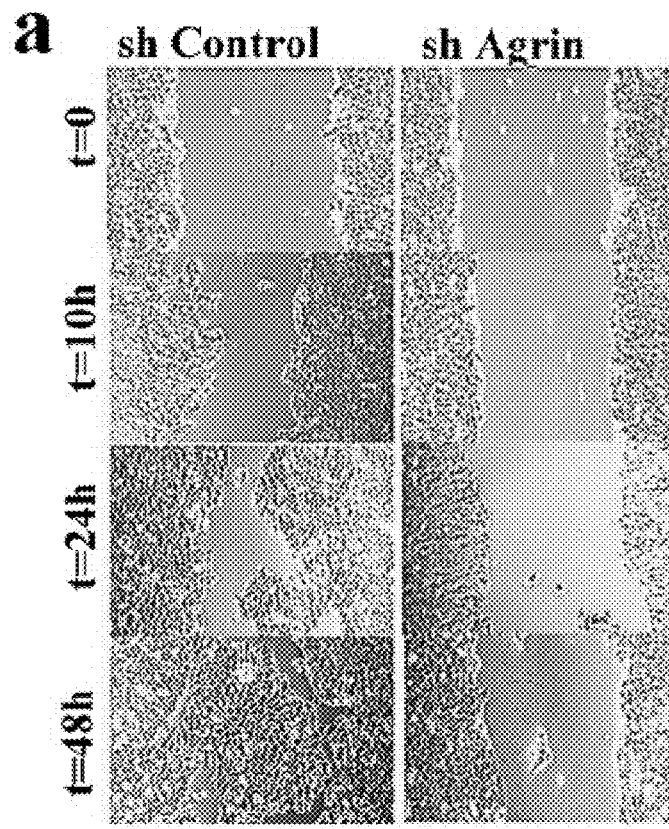
FIG. 4 shows results that demonstrate Agrin regulates cancer cell migration, invasiveness and colony formation. In particular, (a and b) shows representative images of wound scratch assay performed in shControl or shAgrin MHCC-LM3 cells. Representative images are shown at indicated time-points and results are quantitated in (b) using Image J software (Magnification-20×); (c) shows the result of a matrigel Boyden chamber invasion assay of control or Agrin knockdown MHCC-LM3 cells either expressing GFP-vector or Agrin-GFP. Cells invading matrigel are imaged in a bright field microscope under 20× magnification. Results are also quantitated using the ImageJ software. Error bars indicate standard deviation of means of three independent biological replicates (P values=0.005 and 0.001, respectively); (d) shows the results of soft-agar clonogenic assay of control or Agrin knockdown MHCC-LM3 cells. Representative pictures for colony growth are shown. Typical cell colonies observed by bright field microscopy at day 10 of growth in soft agar is also shown. Quantitation of the number of colonies is shown. Error bars indicate standard deviation of the means of three independent biological replicates. (P value=0.004); (e) shows representative live cell time-lapse differential interference contrast (DIC) images of control and Agrin knockdown cells at indicated time-points are shown. Scale bar: 10 μm. Arrows indicate invadopodia; (f) shows Agrin expression as observed using Western blot of MHCC-LM3 cells, which were immunoprecipitated using Arp2/3 antibody or IgG. The blot was stripped and re-probed for Arp2/3. Thirty μg whole cell lysate used as input control; (g) shows Western Blot results of observation of biotinylated surface proteins in control or Agrin shRNA transduced MHCC-LM3 cells. Total cell lysate was also Western blotted for Arp2/3 and β-actin as equal loading control; (h) shows representative confocal images of immunofluorescence analysis performed in control and Agrin knockdown MHCC-LM3 cells 12 h post scratch assay using a goat Arp2/3 antibody and mouse Agrin antibody. Enlarged Z sections were performed at the leading edge of membrane ruffles marked by white arrows. For panel (ii), cells were washed two times with high salt wash buffer (0.5M NaCl) for 10 min at RT prior to fixation and immunostaining. Panels (iii) and (iv) represent images of cells within the wound area and edges of wound, respectively. Scale bar: 10 μm. Thus.
Figure 4:
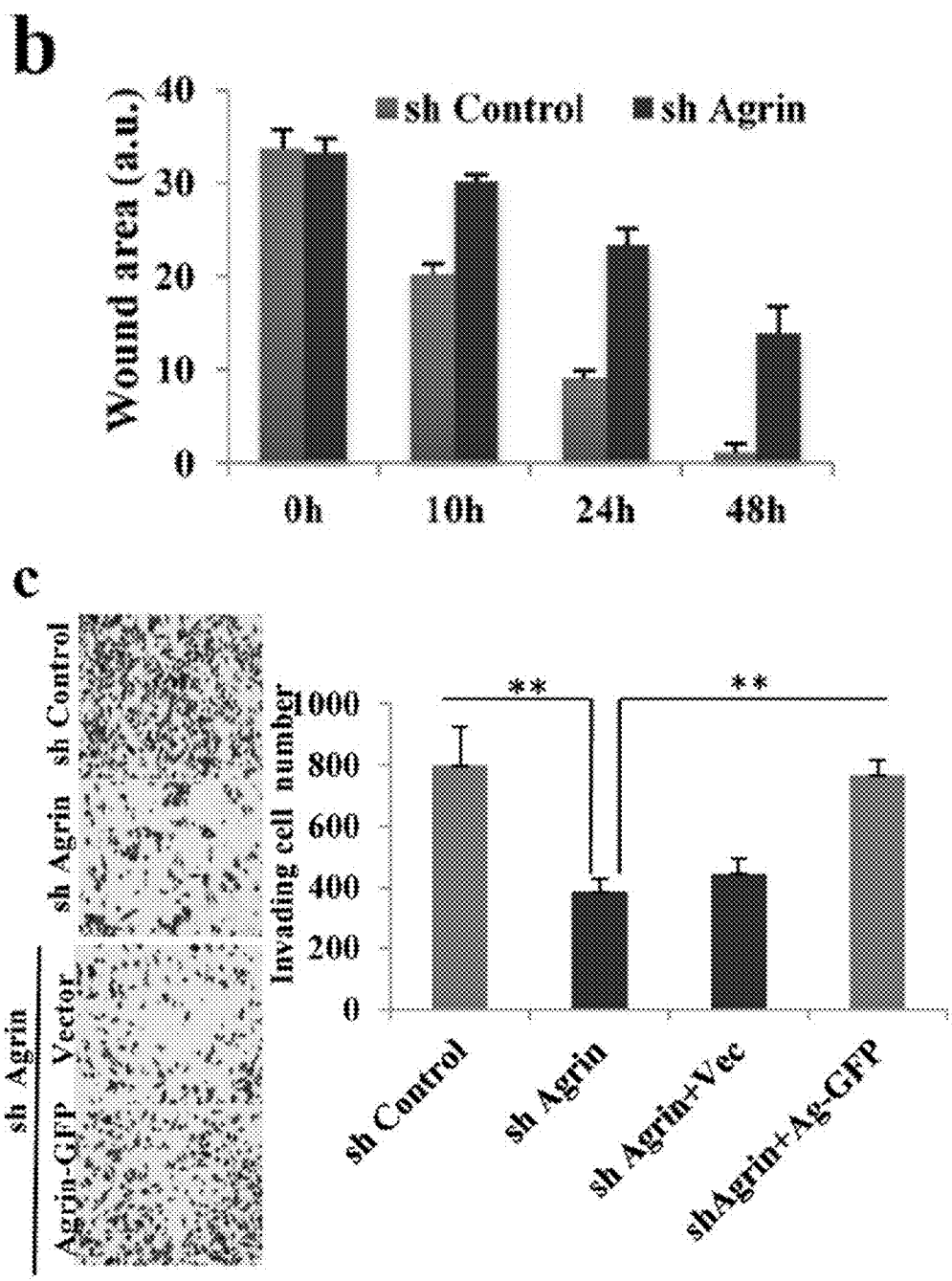
Figure 4:
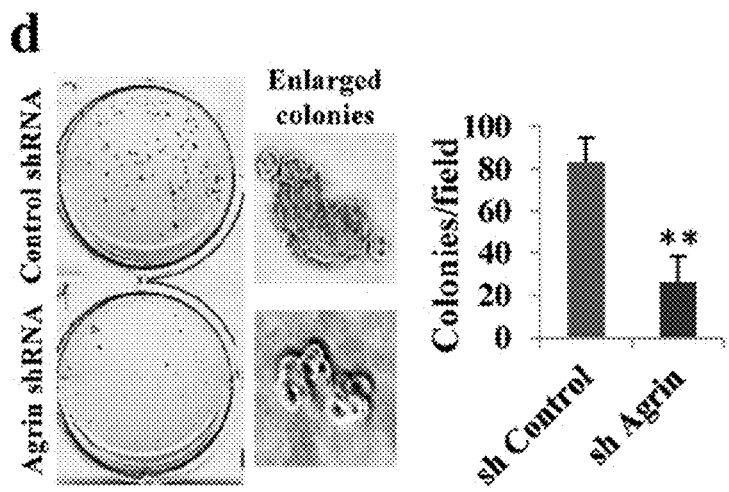
Figure 4:
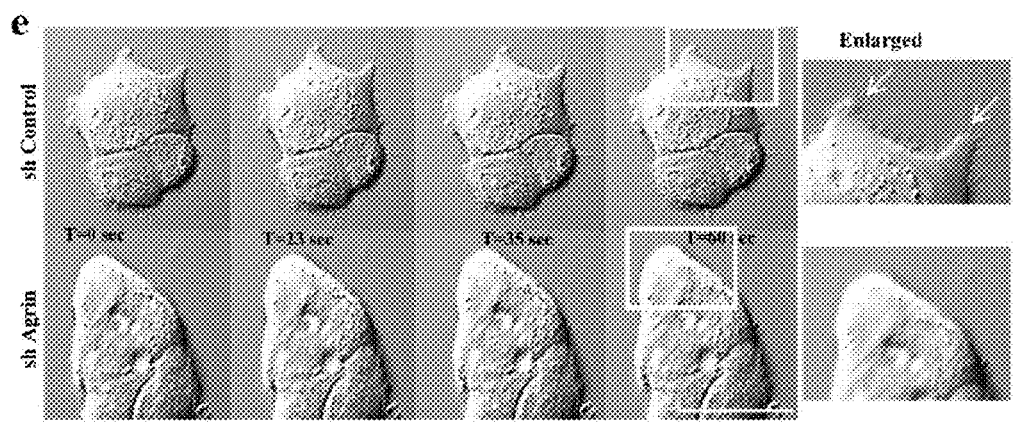
Figure 4:
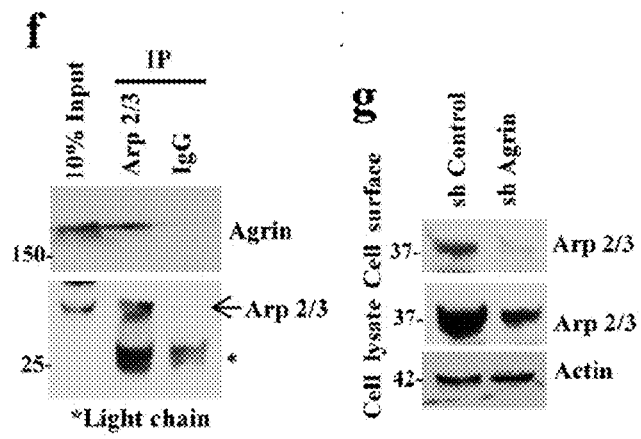
Figure 4:
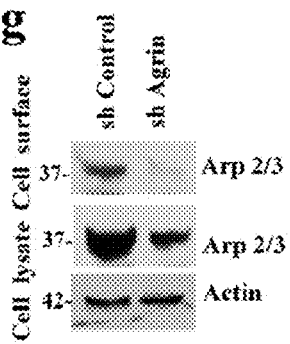
Figure 4:
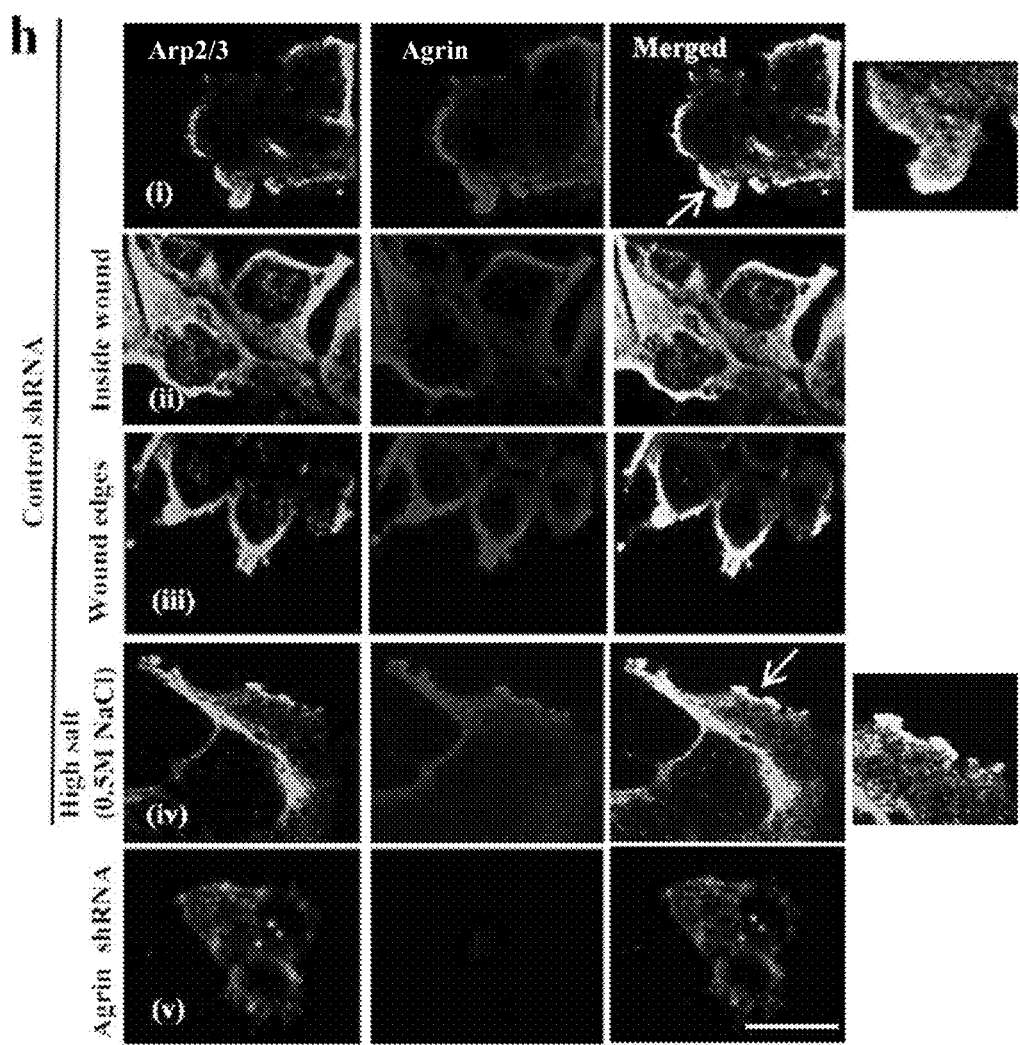

The present disclosure further investigated whether the morphological and proliferative changes in Agrin depleted cells affected migratory and invasive behaviour in vitro. Agrin depletion severely reduced the migration of MHCC-LM3 cells in a wound-healing assay (FIGS. 4a and 4b). While shControl MHCC cells almost recovered the wound area at 48 h post-scratch assay, shAgrin cells had a significant wound area (~15 a.u.) unhealed over the same time-period (FIGS. 4a and 4b). Moreover, Agrin depleted cells also exhibited significantly lower (>50% reduction) infiltration rates through matrigel in a modified Boyden chamber assay than the control cells (FIGS. 4c and S4e). Interestingly, expression of full length Agrin-GFP but not GFP-vector in shAgrin MHCC-LM3 cells significantly rescued the invasive potential through matrigel (FIG. 4c), suggesting the observed phenotype in response to Agrin knockdown is due to reduced Agrin levels. To further demonstrate a role of Agrin in liver tumourigenesis, anchorage-independent growth of Agrin knockdown cells was assessed. As expected, Agrin depleted cells significantly reduced the colony formation by ~65% compared to control cells (FIG. 4d). Compared to well-developed colonies observed in control cells, shAgrin cell colonies were fewer and relatively smaller in size (FIG. 4d, left panel). Therefore, these evidences demonstrate that Agrin is critical for oncogenesis of liver cancer cells.

Agrin Regulates Arp2/3 Dependant Invadopodia Formation

Next the present disclosure determined whether loss of cellular invasion upon Agrin depletion was due to reduction on the ability to form motile membrane protrusions known as Invadopodia or ruffles, a hallmark of invasive cancer cells. Control shRNA transduced MHCC-LM3 cells actively produced invadopodia and/or membrane ruffles throughout the observed 60 sec, while Agrin depleted cells exhibited negligible invadopodia and ruffling movements (FIG. 4e, data not shown). Since invadopodia formation is largely governed by actin related Arp2/3 complex recruitment to the cell surface, the present disclosure deciphered whether Agrin associated with Arp2/3 recruitment to cell surfaces and thereby regulated invadopodia formation. Co-immunoprecipitation with Arp2/3 antibody revealed an interaction of Agrin with Arp2/3 in MHCC-LM3 cells (FIG. 4f). As Arp2/3 and Agrin are distributed on the inside and outside of the plasma membrane, the present disclosure interprets their co-IP as indirect interaction and is likely mediated by transmembrane protein or protein complex. Additionally, there was a sharp decrease in the cell-surface recruitment of Arp2/3 upon Agrin knockdown (FIG. 4g, upper panel). Agrin depletion also reduced the total protein levels of Arp2/3 in MHCC-LM3 cells (FIG. 4g, lower panel). Confocal microscopy analysis revealed that Agrin and Arp2/3 complex colocalized at the leading edge of membrane ruffles in a group of migratory cells 12 h post a wound scratch was performed (FIG. 4h, panel i). Agrin colocalized with Arp2/3 in a similar manner within dense cells and towards the edge of the wound area, ruling out the possibility of wound stress or cell density dependant colocalization between the two proteins (FIG. 4h, panels ii and iii). High salt wash employed to remove peripherally associated proteins, partially affected the colocalization at the leading edge of membrane ruffles (FIG. 4h, panel iv). In contrast, Agrin depleted cells had reduced Arp2/3 at leading edges, consistent with previous observation as described herein (FIG. 4h, panel v). These observations strongly suggest that Arp2/3 recruitment to cell surface and invadopodia formation is Agrin dependant.

Agrin Affects Epithelial Mesenchymal Transition (EMT) Program in HCC Cell Lines

Figure 5:
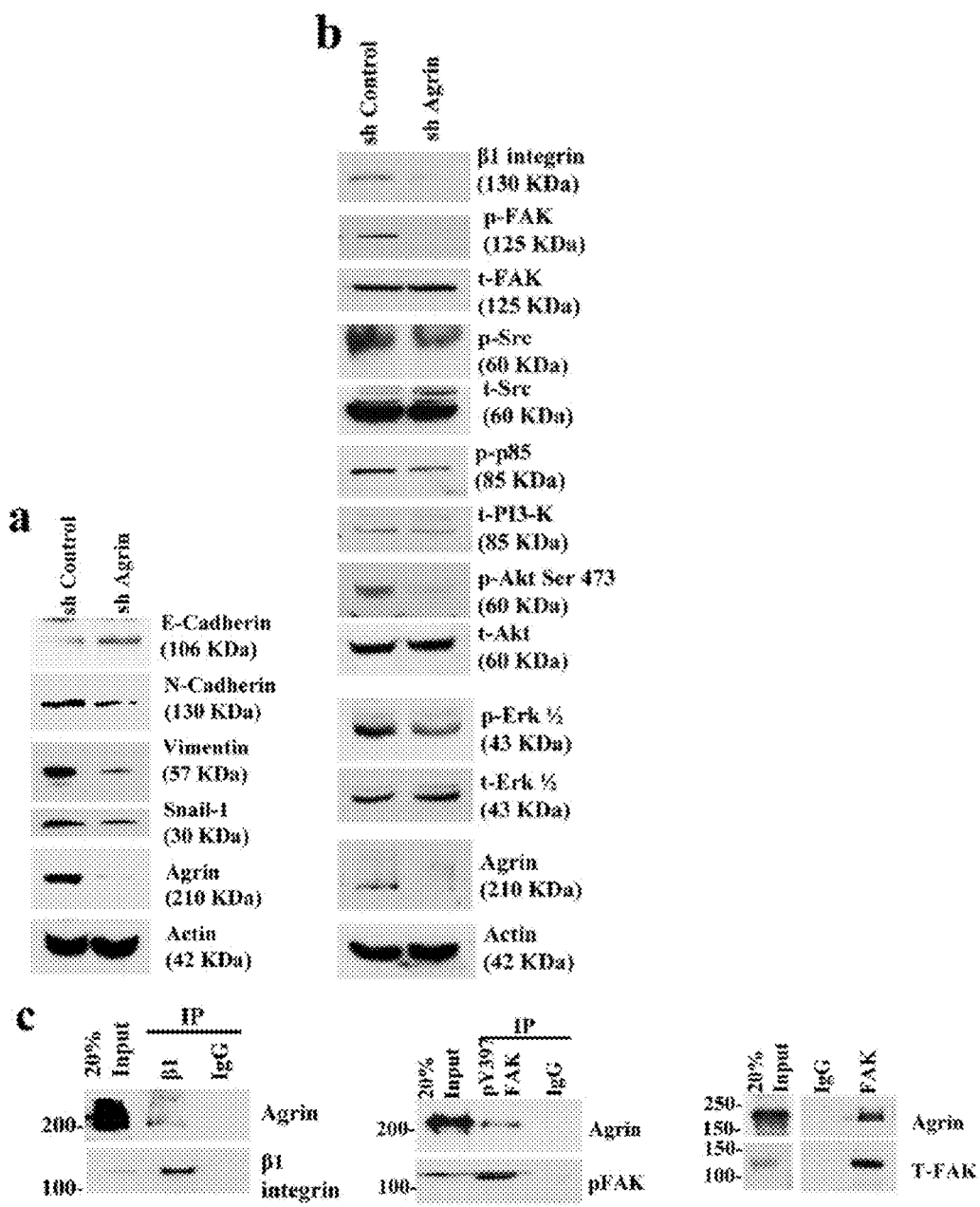
FIG. 5 shows Agrin recruitment of epithelial-mesenchymal transition (EMT) markers and regulation of the integrity of focal adhesion (FA) by acting as an ECM sensor. In particular, (a) shows Western blot results of control or Agrin shRNA transduced MHCC-LM3 cells, which are assayed for indicated EMT marker proteins; (b) shows Western blot results of serum starved control or Agrin shRNA transduced MHCC-LM3 cells, which were analysed for indicated integrin and FA associated signal molecules; (c) shows results of analysis of MHCC-LM3 cells, which were immunoprecipitated with either rabbit IgG or anti-integrin β1 (upper panel), anti-FAK pY397 (middle panel) or anti-Total FAK antibody (lower panel) and Western blotted for Agrin. The blot was stripped and re-probed for integrin β1 (upper panel), pFAK (middle panel) or total FAK (lower panel). Thirty μg whole cell lysate was used as input control; (d) shows representative images of analysis of control or shAgrin transduced MHCC-LM3 cells, which were either mock or pre-treated with 0.5 mM $MnCl_2$ solution in complete media for 30 min at 37° C. to activate FAs, washed and processed for immunofluorescence analysis using rabbit integrin β1 and mouse Agrin antibodies. Representative images co-stained with TO PRO3 are shown. White arrows indicate the enlarged area of cells where Z section was performed. Scale bar: 10 μm; (e) shows representative confocal images of analysis of control or shAgrin transduced MHCC-LM3 cells, which were subjected to immunofluorescence analysis using mouse anti-Agrin and rabbit anti-FAK (pY397) antibodies. Representative confocal images co-stained with TO-PRO3 are shown. Arrows indicate colocalization between Agrin and activated FAK at focal adhesions and boxed areas are represented as enlarged panels. Focal adhesion length was analysed by Image J software and at-least 10 different fields were chosen for analysis; (f) shows representative confocal z-stacks analysis of control or Agrin depleted MHCC-LM3 cells, which were processed for immunofluorescence using rabbit FAK (pY397) and mouse paxillin (pY118) or vinculin antibodies. Representative confocal z-stacks of focal adhesions are shown. Arrows represent elongated focal adhesions. Scale bar: 10 µm; (g) shows representative microscopy images of control or Agrin depleted MHCC-LM3 cells, which were trypsinized and plated on culture dishes pre-coated with 10 µg/ml fibronectin. Morphological changes analysed by time-lapse DIC microscopy live cell imaging at indicated time-points. Scale bar: 10 µm. Thus.
Figure 5:
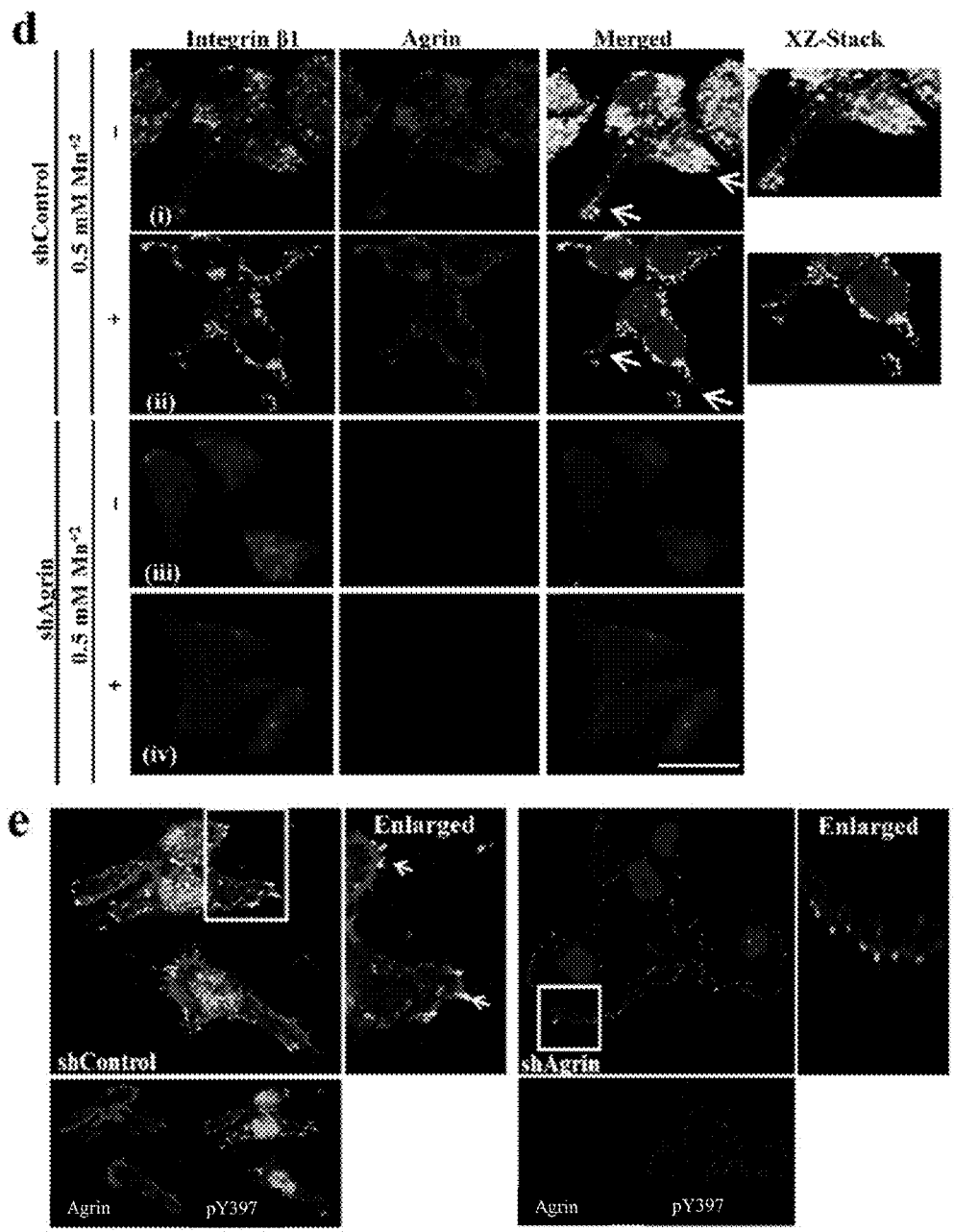
Figure 5:
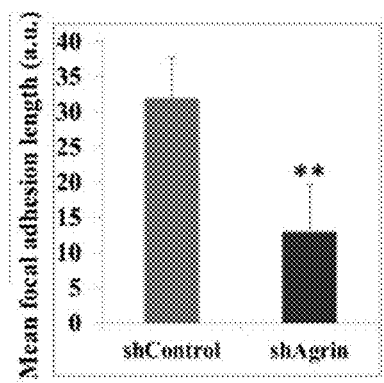
Figure 5:
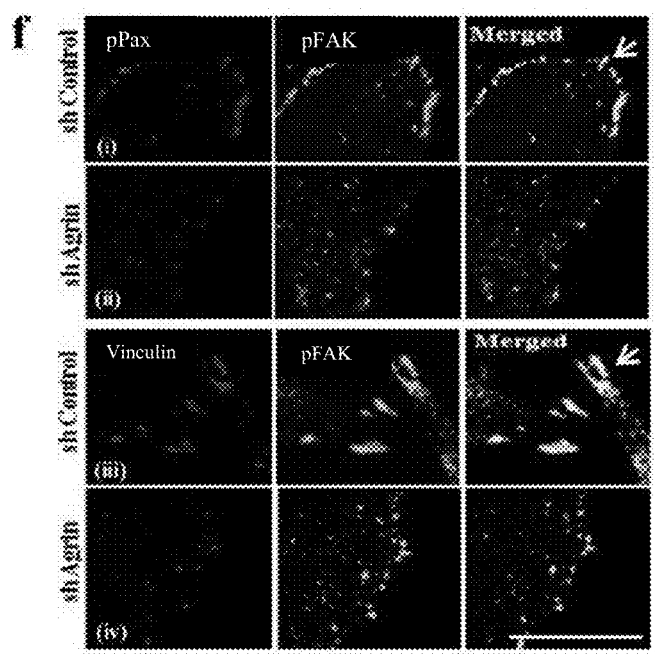
Figure 5:
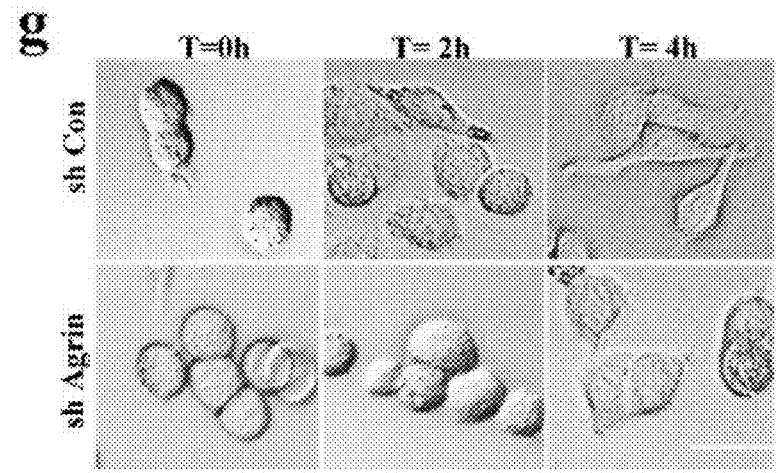
Figure 13:
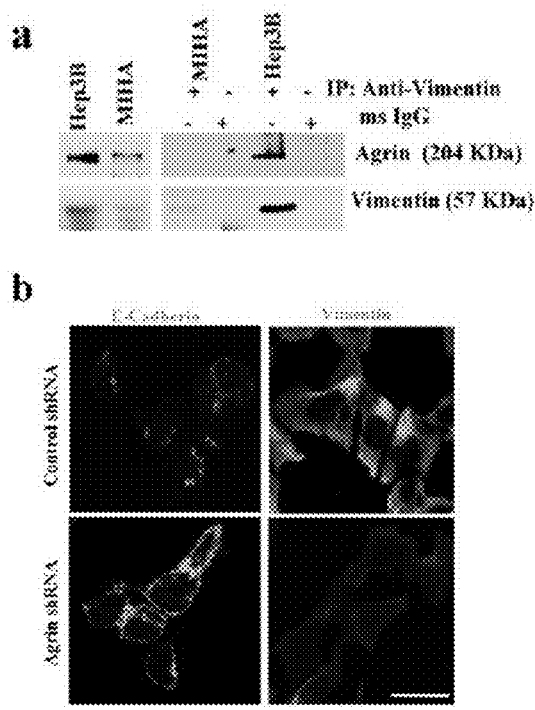
FIG. 13 shows Agrin regulates mesenchymal marker signaling. In particular, (a) shows analysis of three hundred microgram protein from indicated cell lines, which were immunoprecipitated with either mouse IgG or mouse vimentin antibody and analyzed by Western blot probed with an Agrin antibody; (b) shows representative images of confocal microscopy analysis of control or Agrin shRNA transduced MHCC-LM3 cells for E-cadherin and vimentin expression (green) stained by the respective mouse antibodies followed by anti-mouse Alexa 488 secondary antibodies. The cells were co-stained with DAPI (blue). Scale bar: 10 µm; (c) shows Western blot results of control or Agrin shRNA transduced MHCC-LM3 cells, which were surface biotinylated and analyzed using a vimentin specific antibody. Corresponding total cell lysate expression is also shown. β-actin served as loading control; (d) shows Hep3B cells, which were transfected with either control or Agrin specific siRNA. 72 h post transfection, cell lysates were subjected to Western blot analysis for the indicated signaling proteins. β-actin served as loading control. Thus.
Figure 13:
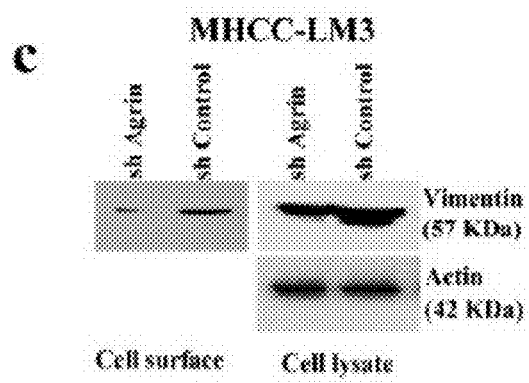
Figure 13:
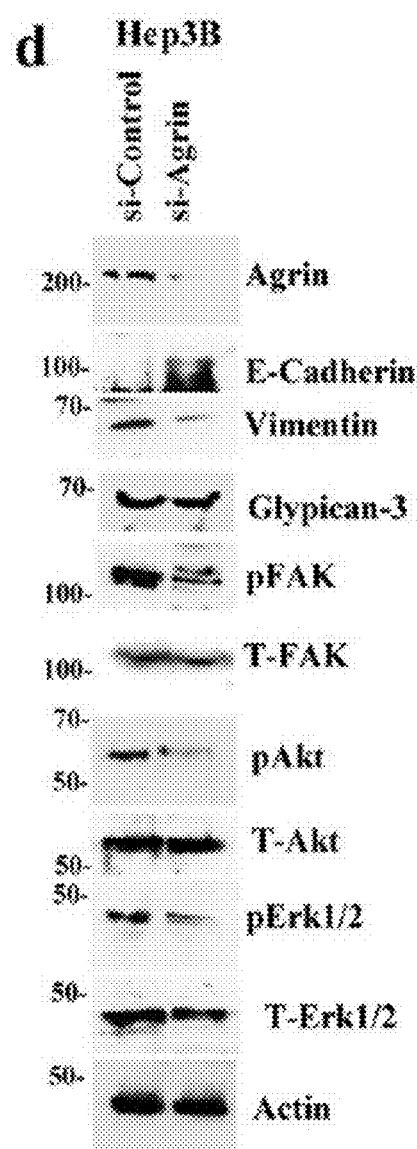

The present disclosure further evaluated whether increased cell-cell contacts observed upon Agrin depletion was due to changes in EMT. Together with this, the present study had also observed the presence of increased levels of Vimentin as one of the cell surface overexpressed proteins likely due to direct association with membrane protein complexes (data not shown). Therefore, the inventors of the present disclosure hypothesised that Agrin might play a role in vimentin and associated mesenchymal marker recruitment to the plasma membrane. As such, vimentin and Agrin associated in Hep3B cells but not in MIHA cells owing to its lesser expression of vimentin and Agrin (FIG. 13a). Agrin depleted cells revealed a significant increase in E-Cadherin with a concomitant reduction in mesenchymal markers including N-Cadherin, Vimentin and Snail-1, respectively (FIG. 5a). Elevated E-cadherin levels coupled with reduced vimentin in Agrin depleted cells further suggest that Agrin alters EMT markers expression and regulates their recruitment to cell surfaces (FIGS. 13b and 13c). Similar results were also observed upon treatment of a siRNA against Agrin in Hep3B cells which depleted Agrin but had no non-specific effects on the expression of another proteoglycan Glypican-3 (FIG. 13d). These lines of evidence are suggestive of anti-mesenchymal characteristics upon Agrin depletion.

Agrin Regulates Signaling of Integrin Associated Focal Adhesion (FA)

Cancer cell invasiveness governed by signaling at invadopodia consisting of integrins and focal adhesion kinases (FAK) is instrumental in recruiting mesenchymal markers to cell surface. To explore a mechanistic role of Agrin in modulating integrin associated signaling and thereby regulating EMT progression and invasiveness, the present study first determined whether Agrin depletion affected integrin signaling pathway. Interestingly, Agrin depleted cells showed marked reduction in integrin β1 and pY397 FAK, two key focal adhesion proteins (FIG. 5b). pSrc and pPI3-K pathways are less affected when compared to focal adhesion complex proteins (FIG. 5b). Notably, Agrin knockdown cells also showed severe reduction in pAkt and pErk1/2 signaling accounting for their poor proliferation (FIGS. 5b and 13d).

As Agrin is known to bind laminin, the present study next evaluated whether it is associated with integrin-focal adhesion components. An interaction between Agrin and integrin β1 was observed in a co-immunoprecipitation analysis (FIG. 5c, upper panel). Similarly, Agrin was also co-immunoprecipitated with activated (pY397) and total FAK in MHCC-LM3 cells (FIG. 5c, middle and lower panel). In addition to significant colocalization observed without stimulation, activation of integrin and focal adhesions (FAs) by Mn+2 led to an increased Agrin clustering in FA regions (FIG. 5d, panels i and ii). In contrast, integrin β1 appeared dispersed and not restricted to FA in Agrin depleted cells (FIG. 5d, panel iii). Even $Mn^{+2}$ stimulation in these cells failed to activate the integrin and adhesion complexes (FIG. 5d, panel iv), suggesting that Agrin depletion grossly affects integrity of focal adhesions.

Figure 14:
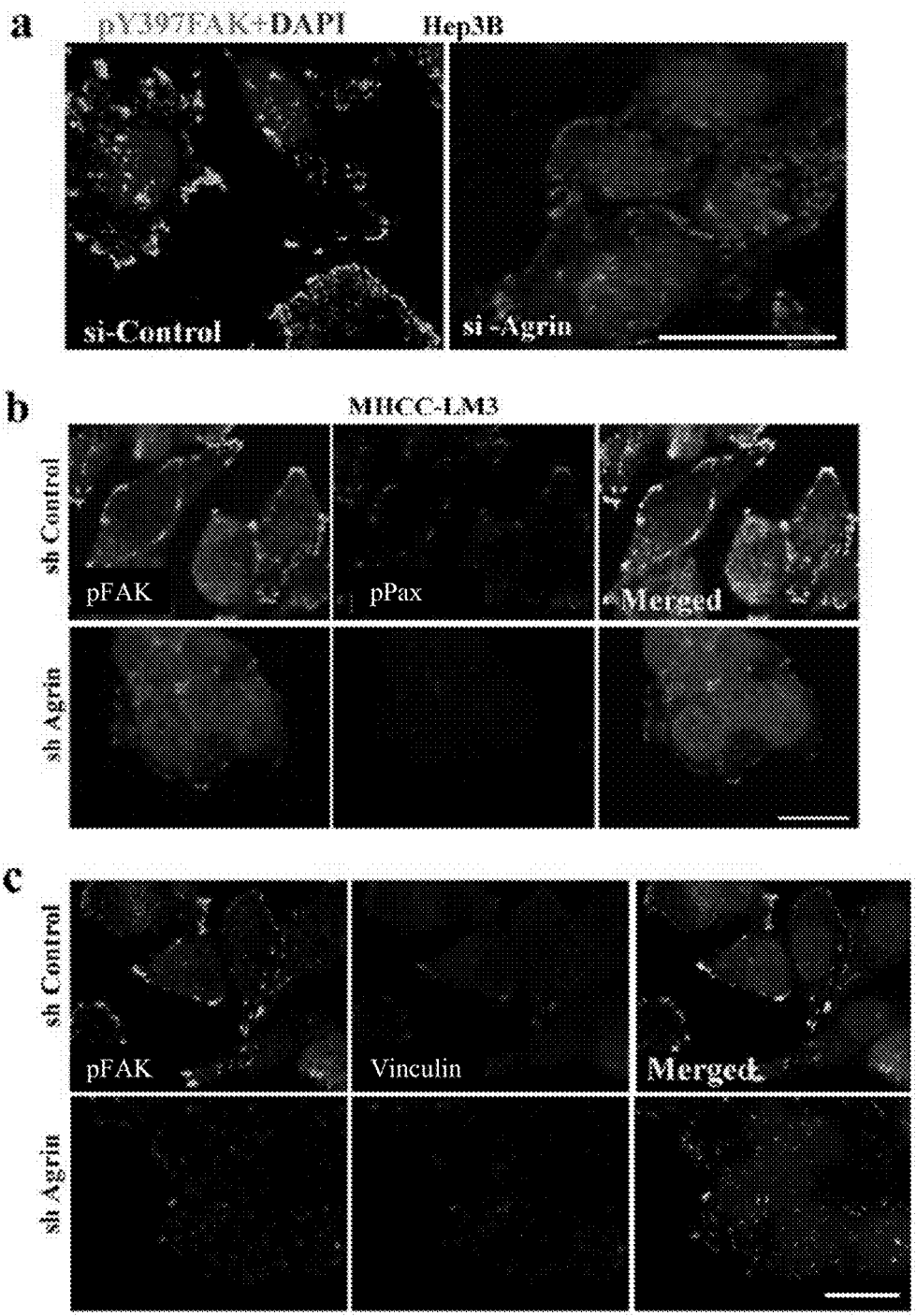
FIG. 14 shows regulation of focal adhesion integrity by Agrin in HCC cell lines. In particular, (a) shows confocal immunofluorescence analysis of focal adhesion in control and Agrin shRNA transduced Hep3B cells, which is visualized by phospho-FAK (pY397) rabbit antibody followed by anti-rabbit secondary antibody conjugated with Alexa fluor 488; (b and c) show representative confocal images of control or Agrin shRNA MHCC-LM3 cells, which were immunostained with rabbit phospho-paxillin (Tyr118) (b) or rabbit vinculin (c) and mouse pFAK antibodies followed by anti-rabbit Alexa fluor 488 and mouse alexa fluor 594 antibodies. Scale bar: 10 µm; (d) shows representative image of serum starved control or Agrin knockdown MHCC-LM3 cells, which were trypsinized and plated on fibronectin coated plates for 2 h. Post fixation, cells were stained with pFAK pY397. Cell elongation ratio calculated by signal intensity measurements for length and width of each cell in at least 5 different microscopic fields containing at least 10 cells each. Scale bar: 10 µm.
Figure 14:
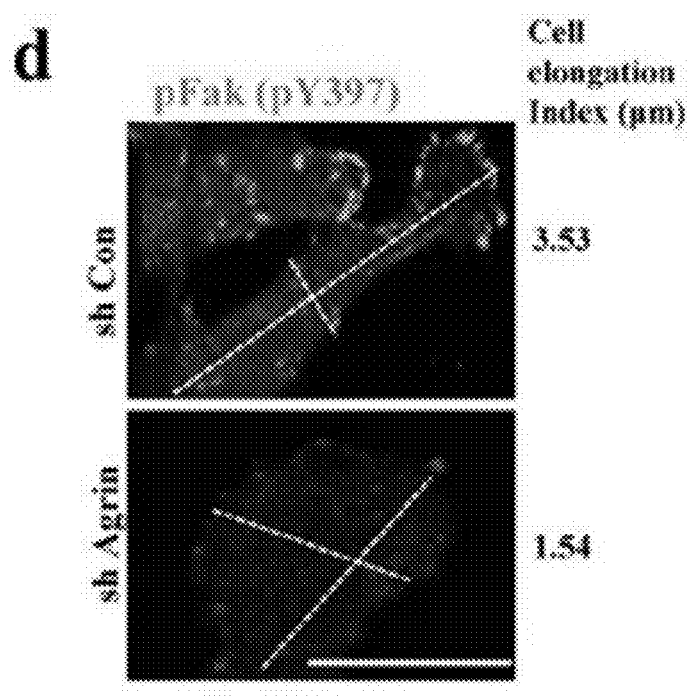

Agrin Acts as an ECM Sensor Regulating Focal Adhesion Based Cell Attachment Dynamics To address whether and how Agrin provides extracellular matrix cues that regulate focal adhesion dynamics, the present study examined whether Agrin depletion directly disrupted FA junctions. Control cells exhibited colocalization between Agrin and pFAK (pY397) in FA regions, while Agrin depleted cells had reduced levels of activated FAK and FA lengths compared to control cells (FIGS. 5e and 14a). These observations are similar to the effects of myosin IIA bleb inhibitor, blebbistatin, and indicate focal adhesion disruptions. Confocal immunofluorescence analysis between activated focal adhesion kinase and its immediate downstream components phospho-paxillin (Tyr118) and vinculin further revealed that control cell pFAK, p-Paxillin (Tyr118) and vinculin typically colocalized at elongated FA junctions symbolizing activated FA (FIGS. 5f-panels i and iii, 14b and 14c). However, Agrin depletion clearly disrupted these FA regions (FIGS. 5f-panels ii, iv, 14b and 14c). Moreover, control cells appeared elongated with distinct FA regions and were strikingly different from circular widespread Agrin depleted cells with fragmented FAs (FIGS. 14b and 14c). Since defect in cell morphology has been previously associated with poor focal adhesion alignment and loss of invasiveness, the present study further investigated whether focal adhesion disruption caused by Agrin depletion affected cell shape and attachment dynamics. Upon plating control and Agrin knockdown cells in fibronectin coated plates, they appeared round (FIG. 5g, T=0 h panel). After 2 h, control MHCC-LM3 cells began elongating, while Agrin depleted cells remained circular and spread-out (FIG. 5g, T=2 h panel). At 4 h post plating, both control and Agrin depleted cells attached; the former appearing typically elongated with aligned focal adhesion activity, while the latter widespread with poor focal adhesion activity (FIG. 5g, T=4 h panel and 14d). The cell elongation ratio (calculated by the length over width per cell) was 3.53 and 1.54 µm for control and Agrin knockdown cells, respectively (FIG. 14d).

Figure 6:
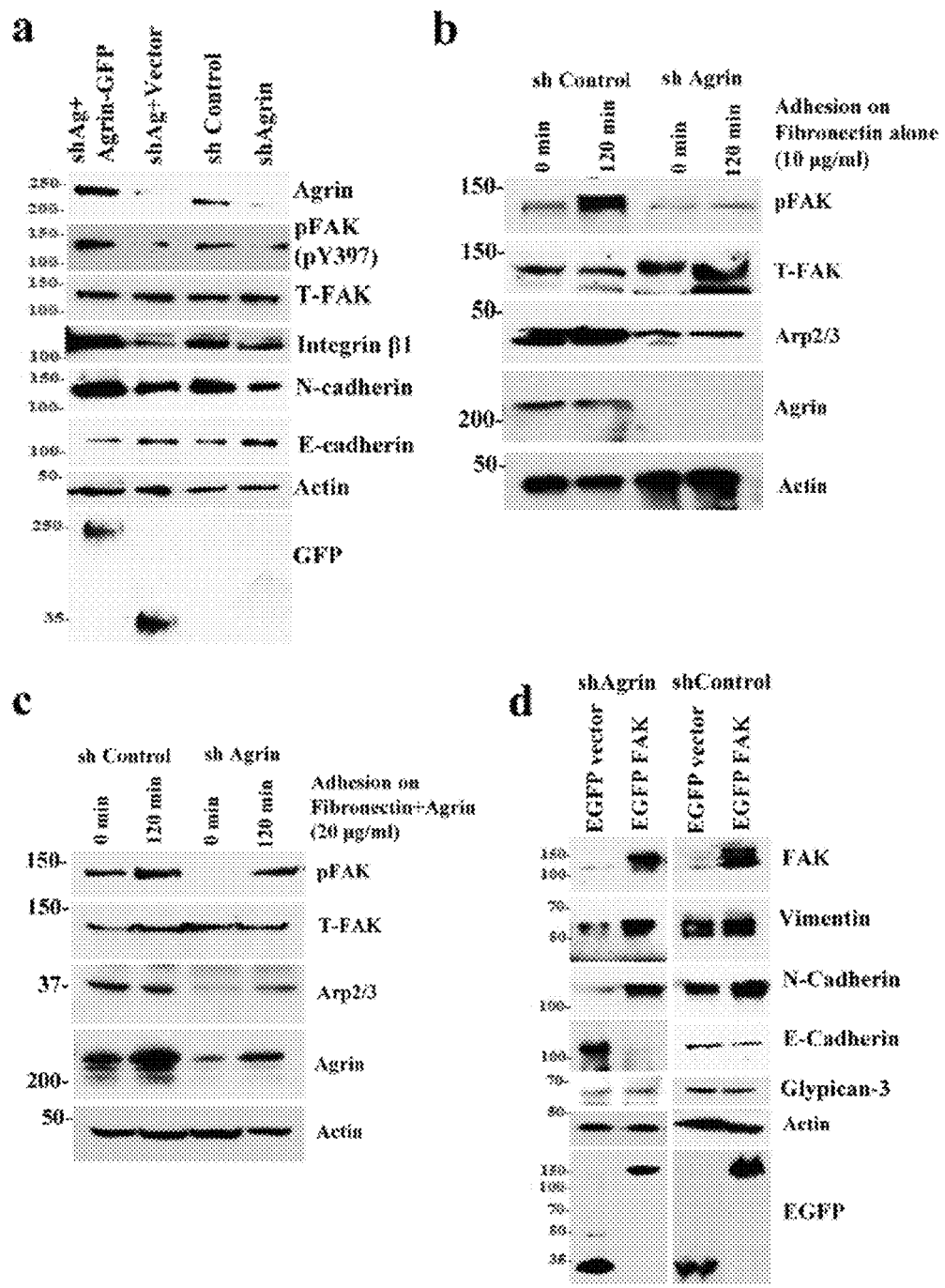
FIG. 6 shows rescue of oncogenic properties by Agrin or FAK reconstitution is dependent on Agrin-MuSK scaffold. In particular, (a) shows Western blot analysis of control or Agrin depleted MHCC-LM3 cells, which were transfected with GFP-vector or full length Agrin-GFP. 72 h post transfections, cell lysates were analysed for indicated proteins; (b and c) show Western blot analysis of control or Agrin depleted MHCC-LM3 cells, which were serum starved overnight, trypsinized and plated on fibronectin or fibronectin supplemented with 20 µg/ml recombinant Agrin coated surface. Lysates were analysed for indicated proteins. β-actin served as loading control; (d) shows Western blot analysis of control or Agrin depleted MHCC-LM3 cells, which were transfected with EGFP-vector or EGFP-FAK. 72 h post transfections, cell lysates were analysed for the indicated proteins; (e) shows analysis of control or Agrin depleted MHCC-LM3 cells, which were immunoprecipitated with MuSK antibody and Western blotted using a tyrosine specific 4G10 monoclonal antibody. The blot was stripped and re-probed for MuSK, Agrin and β-actin as loading control; (f) shows analysis of control or MuSK siRNA transfected MHCC-LM3 cells, which were immunoprecipitated with either rabbit IgG or total FAK antibody and analysed by Western blotting for Agrin. Thirty µg protein lysate was used as input control; (g) shows representative images of control or MuSK knockdown MHCC-LM3 cells, which were subjected to a matrigel invasion assay. Representative images under 20× magnification are shown and results quantitated using Image J software (P value=0.005). Thus, FIG. 6 validates the role of Agrin as an ECM sensor regulating focal adhesion, cell spreading and invasion to affect EMT program in HCC cell lines.
Figure 6:
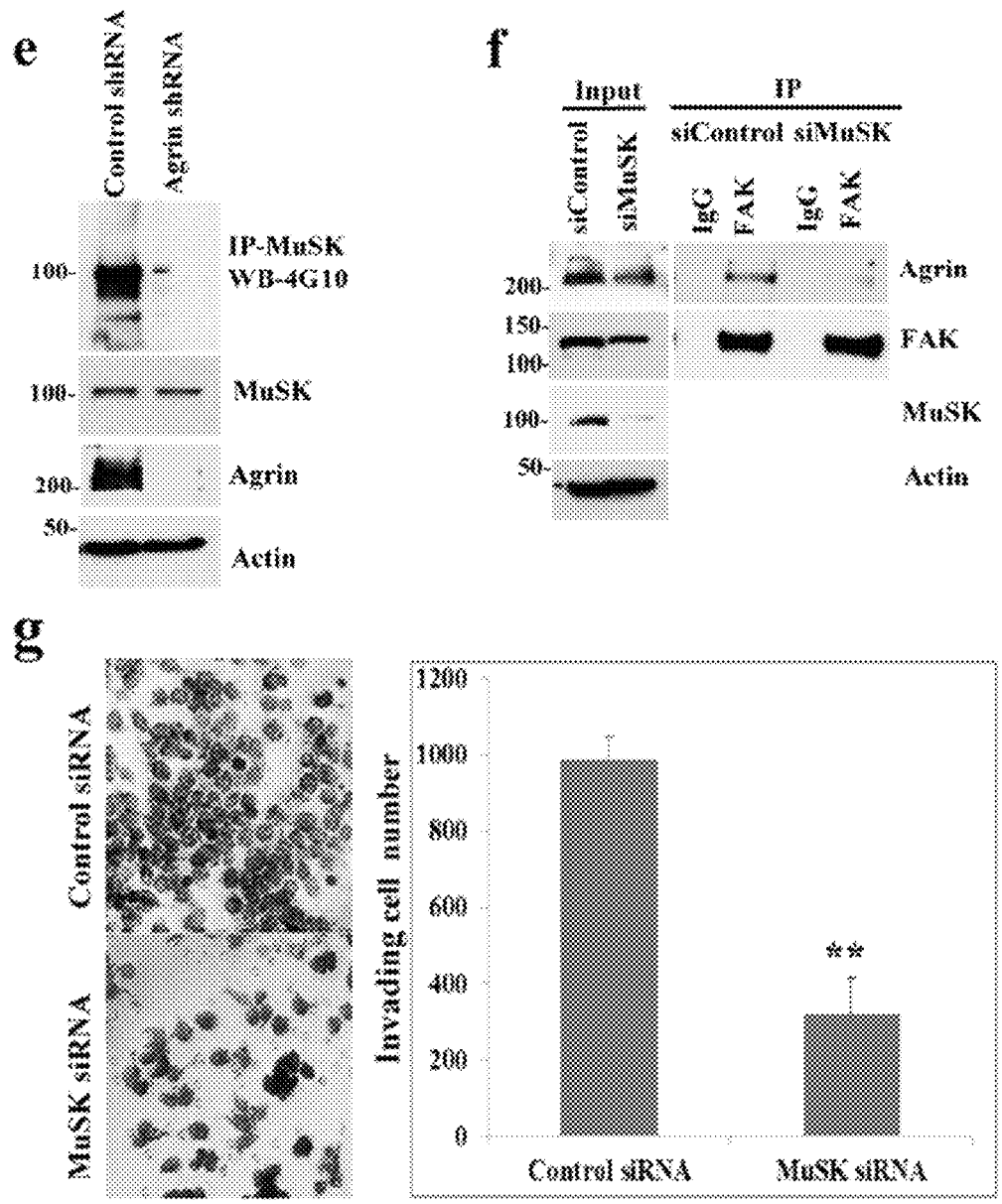

Agrin Restoration Increased Focal Adhesion Activation, Mesenchymal Properties and Attachment Dynamics The inventors of the present disclosure next rationalized that restoring Agrin should rescue the anti-mesenchymal effects and focal adhesion disruption induced by Agrin shRNAs if these phenotypes are attributable to reduced levels of Agrin. Hence, the present study expressed full length Agrin-GFP in Agrin knockdown MHCC-LM3 cells, as depicted by Agrin and GFP Western blots, respectively (FIG. 6a, first panel and last panel). Compared to vector control, Agrin rescued cells exhibited robust increase in activated focal adhesion kinase (pY397) and integrin-β1 levels. In contrast, untransfected control and Agrin depleted MHCC-LM3 cells showed similar reduction in pFAK and integrin as described above (FIG. 6a). Agrin restoration increased mesenchymal marker Ncadherin and reduced epithelial marker E-cadherin (FIG. 6a). Compared to control cells, the inventors of the present disclosure also observed reduced ability of Agrin depleted cells to activate FAK (pY397) and Arp2/3 signalling during attachment on fibronectin coated plates 2 h post-plating (FIG. 6b). Importantly, addition of recombinant Agrin along-with fibronectin as ECM coat substantially increased the activation of focal adhesion kinase and Arp2/3 at 2 h post plating (FIG. 6c). These lines of evidence cumulatively validate the role of Agrin as an ECM sensor regulating focal adhesion, cell spreading and invasion to affect EMT program in HCC cell lines.

Focal Adhesion Kinase Expression Reverses Agrin Depleted Phenotype

Recent studies indicate that FAK is critical for HCC progression. If the key function of Agrin is to maintain and sustain FAK activity, then it should expect that overexpression of FAK alone could bypass, at least in part, the decreased mesenchymal marker recruitment in cell surfaces and invasiveness observed upon Agrin depletion. Interestingly, EGFP15 FAKpY397 expression in Agrin depleted cells restored the mesenchymal marker levels (Vimentin and N-cadherin), while drastically decreasing E-Cadherin (FIG. 6d, shAg panel). Respective FAK and EGFP expression levels are also shown (FIG. 6d). However, FAK expression in Agrin knockdown cells did not affect Glypican-3 expression, suggesting the specificity of FAK to resurrect Agrin mediated effects (FIG. 6d). The present study also did not observe any dramatic effects of FAK overexpression in control shRNA transduced cells (FIG. 6d, shControl panel). Together these observations reveal a synergistic dependence of Agrin on focal adhesion kinase to recruit mesenchymal markers and drive EMT program in HCC and strongly suggest that FAK is a major mediator of Agrin function.

Figure 15:
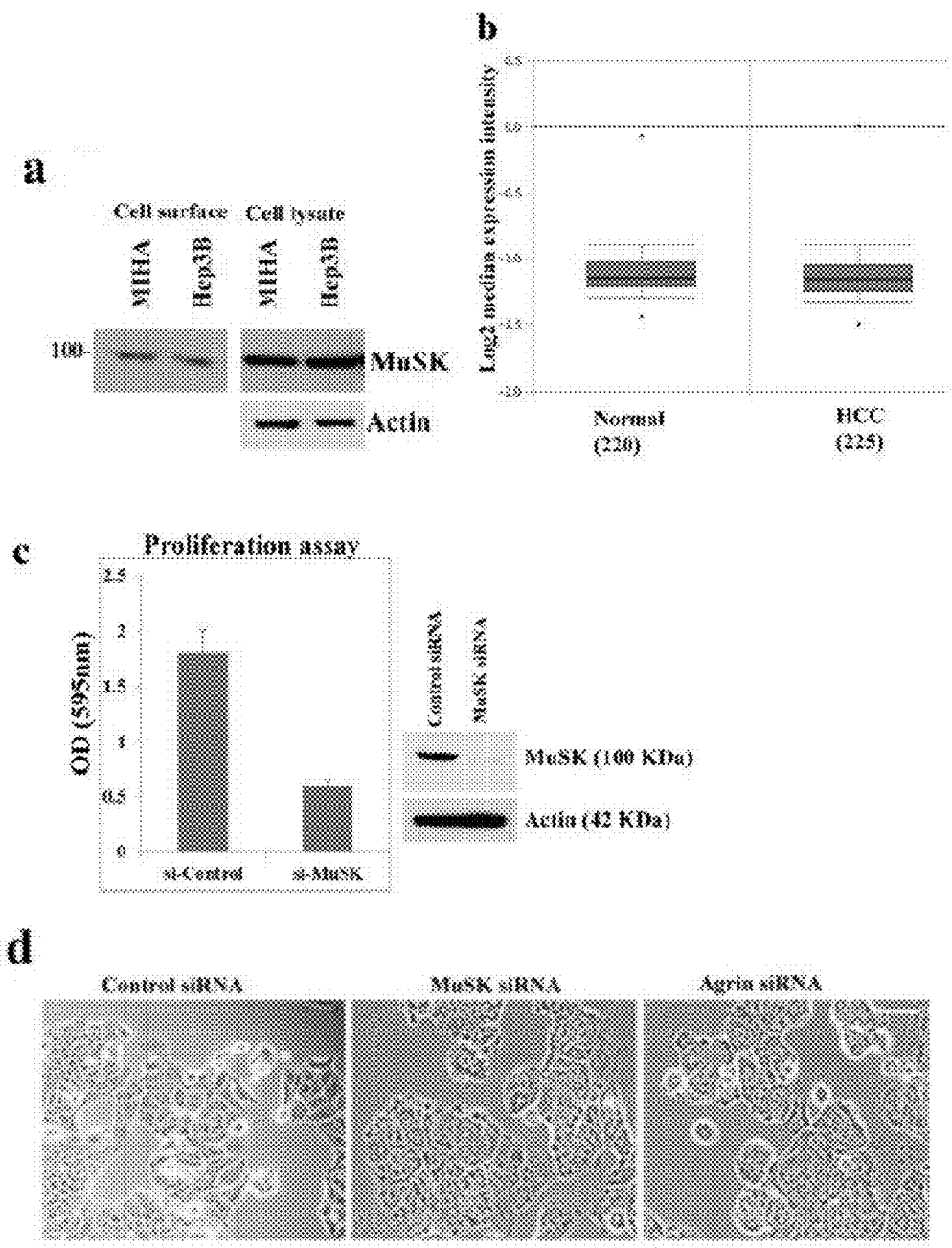
FIG. 15 shows MuSK status and knockdown effects in controlling Agrin related events in HCC. In particular, (a) shows biotinylated cell surface MuSK analyzed by Western blot. Total cell lysate probed with MuSK antibody. β-actin served as loading control; (b) shows mRNA expression profile of MuSK between normal and HCC patient datasets; (c) shows cell proliferation assay measured by crystal violet staining after 3 days post transfection with control or MuSK si-RNA in MHCC-LM3 cells. Western blot in the same transfected cells showing MuSK knockdown. β-actin served as loading control; (d) shows morphology of control, MuSK knockdown and Agrin knockdown cells observed under a bright field microscope under 20× magnification.

Agrin-Muscle Specific Tyrosine Kinase (MuSK) Receptor Scaffolds its Focal Adhesion Association Since Agrin signals through binding and activation of its cognate receptor muscle specific receptor tyrosine kinases (MuSK), it is important to investigate whether the observed roles of Agrin in HCC is mediated through MuSK or occurred independent of this receptor. The present disclosure first checked the phosphorylated-MuSK status upon Agrin depletion. As expected, Agrin depletion strongly reduced tyrosine phosphorylation of MuSK (FIG. 6e). Strikingly, no significant changes in cell surface or total MuSK levels between MIHA and Hep3B cells were observed (FIG. 15a). Also, no change in MuSK mRNA between normal and HCC patient datasets suggests that MuSK by itself is not altered in expression in HCC (FIG. 15b). However, MuSK knockdown in MHCC-LM3 cells severely reduced proliferation and induced morphological changes similar to those observed upon Agrin depletion (FIGS. 15c and 15d). Moreover, MuSK depletion nearly abolished the association of FAK with Agrin and reduced cellular invasion rates by ~70% compared to control cells (FIGS. 6f and 6g). These results clearly suggest that Agrin binding to MuSK forms a critical scaffold for Agrin-mediated signalling focal adhesion and functional outcomes.

Agrin depletion reduces tumour growth in vivo

Having mechanistically deciphered the oncogenic properties of Agrin in vitro, the present disclosure next examined whether loss of Agrin affects tumour development in vivo. Accordingly, athymic nude mice were subcutaneously (s.c.) injected with either control or Agrin shRNA transduced MHCC-LM3 cells ($10^7$ cells/ml). While control cells developed solid tumours greater than 1000 mm$^3$ in volume and weight (at day 36), Agrin depleted xenografts were significantly smaller in volume (~57 mm$^3$) and weight (FIGS. 7a, 7b and 7c). Western blot analysis revealed reduced pY397FAK, pAkt, Vimentin and Ki67 expression in Agrin depleted tumours (FIG. 7d). Concurrently, cleaved caspase-3 markedly increased in Agrin depleted tumours than control tumours (FIG. 7d), strongly supporting the conclusions reached from in vitro studies described above.

Antibodies Targeting Agrin Inhibit Oncogenic Signaling and Tumour Growth

The necessity of Agrin in tumour growth suggests it represents a suitable therapeutic target for HCC. As preliminary evidence, MHCC-LM3 cells were treated with two antibodies targeting Agrin (D2-antibody 1 and MAb5204-antibody 2, respectively). Interestingly, both antibodies inhibited cell migration in a wound-scratch assay as compared to isotype control (FIG. 7e). Similarly, treatment with Agrin antibodies strongly suppressed pY397FAK and pAKT (Ser473) activation without affecting respective total protein levels in MHCC-LM3 cells (FIG. 7f). Agrin antibodies also inhibited N-cadherin and vimentin while up-regulated Ecadherin without affecting Glypican-3 expression (FIG. 7f). Since MAb5204 antibody showed greater in vitro effects, it was selected for deciphering tumour regression effects in vivo. Nude mice injected s.c. with MHCC-LM3 cells were allowed to establish a tumour volume of 100-200 mm$^3$ before administering antibody intra-peritoneally (i.p.). As expected, Agrin antibody treatment significantly suppressed tumour growth when compared to PBS injected mice 17 (FIGS. 7g and 7h). Tumour growth inhibition (TGI) upon Agrin antibody treatment maximized at ~40% at 30 days post initial tumour implantation (FIG. 7i). Furthermore, treated tumours displayed reduced proliferation (Ki67) and increased apoptosis (Cleaved caspase-3) (FIG. 7j), indicating that antibodies targeting Agrin effectively inhibit tumour progression in vivo.

Agrin is Frequently Overexpressed in Hepatocellular Carcinoma Patients

Finally to establish a clinical relevance of Agrin's role in HCC, microarray datasets generated from a cohort of liver cancer patients were analysed. Consistent with the findings described above, a 3.5 and 3.9 fold up-regulation of Agrin (AGRN) mRNA were observed in HCC patients (compared to normal liver tissues) in two independent datasets, with P values of 6.22e-6 and 1.22e-7, respectively (FIG. 8a). Western blot analysis of matched normal (nontumour; N) and HCC (liver-tumour; T) samples of HCC patients revealed a significant upregulation of Agrin in 9 out of 11 HCC patients (FIG. 8b). Similarly compared to normal liver tissues, Agrin overexpression was also observed across various stages of HCC (FIG. 16). Furthermore, circulating levels of plasma Agrin were also majorly increased in HCC patients when compared to normal individuals (FIG. 8c). Taken together, these clinical evidences confirmed that Agrin is overexpressed in HCC and associated with increased levels of circulating Agrin.

Comprehensive lines of evidence presented here identify a unique role of extracellular matrix and cell surface Agrin in providing oncogenic cues that activate focal adhesions to drive liver tumourigenesis. The present disclosure demonstrates Agrin's role in in vitro and in vivo liver tumourigenic potential by manipulating cellular migration and adhesion dynamics. Together with gaining insights into the molecular mechanisms of Agrin function in cellular adhesion and invasion, the present Example section also validated the frequent up-regulation of Agrin in clinical hepatocellular carcinoma (HCC) patient samples. Since cell surface proteins are the best known therapeutic targets in most cancers, the results described above shows that targeting Agrin suppresses liver carcinogenesis through decreased focal adhesion activity, improper adhesion dynamics, loss of cell migration and invasiveness.

Proteomic screens offer robust and unbiased approach to screen candidates in many cancer types. It is known that instances of quantitative screening of cell membrane proteins in liver cancer are rare. Therefore, SILAC screen identifying several differentially expressed cell surface proteins in Hep3B cells compared to MIHA cells was designed accordingly. Apart from the global identification of several unique candidates, some identified proteins are established key players in hepatocellular carcinoma and other cancers. Through the surprising finding of the inventors, Agrin has been demonstrated to be secreted and enriched in lipid rafts from where it can be actively endocytosed. Such endocytosis of over expressed receptors is often associated with signal amplification in many cancers, such as hepatocellular carcinoma, breast cancer and cholangiocarcinoma.

EMT program in cancer is achieved when invading tumour cells breach through the underlying basement membrane and ECM. However, the integrity of basement membrane components regulating EMT in cancers is unknown. Interestingly, Agrin is reported as a basement membrane protein. Evidences including changes in cell morphology, reversal of EMT characteristics (increase of E-cadherin with the concomitant decrease in vimentin) and loss of invasiveness and clonogenicity upon Agrin knockdown are suggestive of Agrin's role in enabling tumour cells to invade through the basement membrane. Conversely, this is further supported by Agrin rescue experiments which increased mesenchymal characteristics and invasiveness.

It was shown herein that Agrin enables tumour cells to invade through basement and ECM. The evidences described above shows that Agrin assists two major steps in promoting invasion of tumour cells. Firstly coupled with engagement of Arp2/3 at the leading edges of tumour cells, Agrin regulates invadopodia formation required for ECM degradation and tumour invasion. Secondly, Agrin signals activate integrins and focal adhesions kinases necessary for sustained focal adhesions integrity. Loss of functional Agrin hampers focal adhesion integrity while Agrin expression restores FA activity and mesenchymal characteristics. FAK is known to recruit mesenchymal characteristics bestowing adhesion and invasiveness in cancer. Therefore, synergistic effects of Agrin with FAK probably drives EMT program in HCC, corroborated by FAK complementation in Agrin deprived cells as evidenced in the present disclosure. As integrins and FAK signaling are critical for directing proliferation for metastatic cancer cells, it can be speculated that Agrin provides necessary stimulatory effects to augment FAK signaling during extravasation into parenchyma. Instances where Agrin depleted cells displayed poor focal adhesion activity correlating with loss of invasiveness shed light to the above hypothesis. Elevated Agrin expression leads to enhanced binding to its cognate receptor tyrosine kinase MuSK, which probably activates focal adhesions. Anti-proliferative effects, loss of focal adhesion interactions and reduced invasion of HCC cells upon MuSK depletion in presence of Agrin strongly support that MuSK-Agrin interaction forms a critical scaffold for Agrin signal transduction and amplification required for focal adhesion activity (FIG. 8d). While Arp2/3 complex derived membrane protrusions promote focal adhesion alignment and cell migration, the molecular partner(s) distributing signaling gradients for directional movements and membrane protrusion formation were unknown. Interestingly, loss of focal adhesion and Arp2/3 activity with changes in cell shape upon Agrin depletion can be significantly reversed by Agrin supplementation in the ECM. Therefore, Agrin appears as the unique link via MuSK between extracellular surface and FAK associated signaling critical for regulating EMT and tumourigenesis (FIG. 8d).

On the clinical perspective, in one example, Agrin expression was higher in cancer patients, such as HCC patients, compared to matched non-tumour tissues in patients. Gene expression analyses in HCC microarray datasets, elevated protein levels in tissues and plasma of HCC patients cumulatively support a strong oncogenic role of Agrin in liver cancer. In vivo, Agrin depletion hampered oncogenic signalling and tumour development. Treatment with well characterized commercial Agrin monoclonal antibodies shows in vitro and in vivo anti-oncogenic effects resulting in significant tumour growth inhibition. The fact that Agrin is poorly expressed in normal livers and Agrin antibodies inhibited pre-established tumour growth in vivo without substantial detrimental effects demonstrates that it is a therapeutic target in hepatocellular carcinoma.

In conclusion, the present disclosure recognizes Agrin as factor that provides cell surface bound gradients necessary to activate and coordinate cellular adhesion, migration, membrane ruffling and invasiveness with hepatocellular carcinoma progression. Therefore, Agrin targeting antibodies will augment additional cancer therapeutic strategies. Moreover, the identification of Agrin's role in monitoring cell adhesion and invasion sheds light on the broad cellular mechanisms as to how proteoglycans may regulate cancer progression, such as HCC.

The invention claimed is:

1. A method of treating a hepatocellular carcinoma in a subject in need thereof comprising
    determining the level of extracellular form of Agrin in an extracellular fluid obtained from the subject,
        wherein an increased level of the extracellular form of Agrin in the extracellular fluid is indicative of a presence or progression of the cancer,
        wherein an increased level is determined by comparison of the level of extracellular form of Agrin in the subject with the extracellular form of Agrin in a non-diseased subject; and
    administering a therapeutically effective amount of an anti-Agrin agent to the subject determined to have the presence or progression of the cancer, wherein the anti-Agrin agent is selected from the group consisting of neutralizing antibody Agrin antibody (D-2) and neutralizing antibody anti-Agrin antibody MAB5204.

2. The method of claim 1, wherein the extracellular Agrin is a splice variant of Agrin that is secreted in extracellular matrix.

3. The method of claim 1, wherein the Agrin comprises the C-terminal fragment portion (C20) 20 KDa protein fragment.

4. The method of claim 1, wherein the extracellular fluid is whole blood.

5. The method of claim 1, wherein the anti-Agrin agent functionally blocks the c-terminally active signaling component of membrane-bound Agrin.

6. The method of claim 1, wherein the anti-Agrin agent binds to or recognizes SEQ ID NO: 1, SEQ ID NO: 2, SEQ ID NO: 3, SEQ ID NO: 4 and/or SEQ ID NO: 5.

7. The method of claim 1, wherein the antibody is provided as a humanized antibody.

8. The method of claim 1, wherein the subject is a human.

* * * * *